(12) United States Patent
Liu et al.

(10) Patent No.: US 9,005,262 B2
(45) Date of Patent: *Apr. 14, 2015

(54) RADIATION-BASED DERMATOLOGICAL DEVICES AND METHODS

(75) Inventors: Harvey I-Heng Liu, Fremont, CA (US);
Tobin C. Island, Oakland, CA (US);
Patrick Reichert, Dublin, CA (US);
Mark V. Weckwerth, Pleasanton, CA (US)

(73) Assignee: Tria Beauty, Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/366,154

(22) Filed: Feb. 3, 2012

(65) Prior Publication Data

US 2012/0232536 A1    Sep. 13, 2012

Related U.S. Application Data

(60) Provisional application No. 61/439,353, filed on Feb. 3, 2011, provisional application No. 61/444,079, filed on Feb. 17, 2011, provisional application No. 61/469,316, filed on Mar. 30, 2011, provisional (Continued)

(51) Int. Cl.
*A61N 5/06*    (2006.01)
*A61B 18/18*    (2006.01)

(Continued)

(52) U.S. Cl.
CPC ............ *A61N 5/0616* (2013.01); *A61B 18/203* (2013.01); *A61B 2017/00154* (2013.01); *A61B 2017/00769* (2013.01); *A61B 2018/00458* (2013.01); *A61B 2018/0047* (2013.01); *A61B 2018/00476* (2013.01);

(Continued)

(58) Field of Classification Search
CPC .................. A61B 18/203; A61B 2017/00154; A61B 2018/00452–2018/00476; A61N 5/0616; A61N 2005/0644
USPC ........................ 606/9, 10–13; 607/88, 89, 100
See application file for complete search history.

(56) References Cited

U.S. PATENT DOCUMENTS

| 4,094,576 | A | 6/1978 | Heiling ............................ 359/18 |
| 4,739,177 | A | 4/1988 | Borden ............................ 250/574 |

(Continued)

FOREIGN PATENT DOCUMENTS

| WO | 2008/124839 A1 | 10/2008 | ............. A61B 18/18 |
| WO | 2011/010239 A1 | 1/2011 | ............. A61B 18/20 |

OTHER PUBLICATIONS

Song et al. "Single-fundamental-mode photonic-crystal vertical-cavity surface-emitting lasers" Applied Physics Letters 80, 3901 (2002), DOI:10.1063/1.1481984.*

(Continued)

*Primary Examiner* — Lynsey Crandall
*Assistant Examiner* — Nathan J Jenness
(74) *Attorney, Agent, or Firm* — King & Spalding L.L.P.

(57) ABSTRACT

A device for providing radiation-based dermatological treatments includes a device body configured to be handheld by a user; a VCSEL laser supported in the device body, the VCSEL laser including multiple spaced-apart VCSEL beam sources configured to generate multiple discrete laser beams for generating multiple discrete treatment spots on the skin; an application end configured to be manually moved across the surface of the skin during a treatment session; and electronics configured to control the multiple VCSEL beam sources to emit the multiple discrete laser beams toward the skin to provide a dermatological treatment.

35 Claims, 36 Drawing Sheets

Related U.S. Application Data application No. 61/533,641, filed on Sep. 12, 2011, provisional application No. 61/533,677, filed on Sep. 12, 2011, provisional application No. 61/533,786, filed on Sep. 12, 2011, provisional application No. 61/545,481, filed on Oct. 10, 2011, provisional application No. 61/563,491, filed on Nov. 23, 2011, provisional application No. 61/594,128, filed on Feb. 2, 2012.

(51) Int. Cl.
*A61B 18/20* (2006.01)
*A61B 17/00* (2006.01)
*A61B 18/00* (2006.01)
*A61B 19/00* (2006.01)
*A61N 5/067* (2006.01)

(52) U.S. Cl.
CPC    *A61B 2018/00732* (2013.01); *A61B 2019/409* (2013.01); *A61B 2019/461* (2013.01); *A61B 2019/465* (2013.01); *A61N 2005/0644* (2013.01); *A61N 2005/067* (2013.01); *A61N 5/0613* (2013.01)

(56) References Cited

U.S. PATENT DOCUMENTS

| | | | |
|---|---|---|---|
| 4,799,164 A | 1/1989 | Hellekson et al. | 235/462.4 |
| 5,070,509 A | 12/1991 | Meyers | 372/45.01 |
| 5,186,184 A | 2/1993 | Aindow et al. | 131/281 |
| 5,445,608 A * | 8/1995 | Chen et al. | 604/20 |
| 5,452,181 A | 9/1995 | Hoover | 361/697 |
| 5,475,452 A | 12/1995 | Kuhn et al. | 351/212 |
| 5,522,813 A | 6/1996 | Trelles | 606/2 |
| 5,646,674 A | 7/1997 | Bacon et al. | 347/257 |
| 5,710,631 A | 1/1998 | Bou-ghannam et al. | 356/495 |
| 5,726,793 A | 3/1998 | Boardman et al. | 359/216.1 |
| 5,758,951 A * | 6/1998 | Haitz | 362/259 |
| 5,790,576 A | 8/1998 | Waarts et al. | 372/50.23 |
| 6,057,871 A | 5/2000 | Peterson | 347/238 |
| 6,106,316 A | 8/2000 | Barringer et al. | 439/263 |
| 6,171,302 B1 | 1/2001 | Talpalriu et al. | 606/9 |
| 6,234,687 B1 * | 5/2001 | Hall et al. | 385/88 |
| 6,243,407 B1 | 6/2001 | Mooradian | 372/92 |
| 6,339,577 B1 | 1/2002 | Hineno | 369/112.24 |
| 6,392,813 B1 | 5/2002 | Reardon et al. | 359/641 |
| 6,527,460 B2 * | 3/2003 | Cohen et al. | 385/94 |
| 6,529,542 B1 | 3/2003 | Karlsen et al. | 372/108 |
| 6,758,845 B1 | 7/2004 | Weckwerth et al. | 606/9 |
| 6,771,686 B1 | 8/2004 | Ullman et al. | 372/92 |
| 7,090,670 B2 | 8/2006 | Sink | 606/9 |
| 7,118,563 B2 | 10/2006 | Weckwerth et al. | 606/9 |
| 7,184,184 B2 | 2/2007 | DeBenedictis et al. | 359/201.1 |
| 7,372,606 B2 | 5/2008 | Broome et al. | 359/216.1 |
| 7,420,996 B2 | 9/2008 | Schulte et al. | 372/36 |
| 7,515,346 B2 | 4/2009 | Govorkov et al. | 359/641 |
| 7,633,486 B2 | 12/2009 | Lai et al. | 345/156 |
| 7,636,186 B2 | 12/2009 | DeBenedictis et al. | 359/205.1 |
| 7,684,660 B2 * | 3/2010 | Braunisch et al. | 385/14 |
| 7,777,173 B2 | 8/2010 | Price et al. | 250/221 |
| 8,523,849 B2 | 9/2013 | Liu et al. | 606/9 |
| 8,679,102 B2 | 3/2014 | Reichert et al. | 606/9 |
| 8,685,008 B2 | 4/2014 | Weckwerth et al. | 606/9 |
| 2002/0128695 A1 | 9/2002 | Harth et al. | 607/88 |
| 2003/0171795 A1 | 9/2003 | Walmsley et al. | 607/88 |
| 2004/0036975 A1 | 2/2004 | Slatkine | 359/584 |
| 2004/0152943 A1 | 8/2004 | Zimmerman et al. | 600/13 |
| 2004/0167501 A1 | 8/2004 | Island et al. | 606/9 |
| 2004/0176754 A1 | 9/2004 | Island et al. | 606/9 |
| 2004/0230260 A1 | 11/2004 | Macfarland et al. | 607/89 |
| 2005/0045189 A1 | 3/2005 | Jay | 128/898 |
| 2005/0141068 A1 | 6/2005 | DeBenedictis et al. | 359/201.1 |
| 2006/0149343 A1 | 7/2006 | Altshuler et al. | 607/90 |
| 2006/0155266 A1 | 7/2006 | Manstein et al. | 606/17 |
| 2006/0200114 A1 | 9/2006 | Ferren et al. | 606/9 |
| 2006/0227836 A1 | 10/2006 | Omori et al. | 372/50.124 |
| 2007/0179481 A1 | 8/2007 | Frangineas et al. | 606/9 |
| 2007/0185553 A1 * | 8/2007 | Kennedy | 607/100 |
| 2007/0198004 A1 | 8/2007 | Altshuler et al. | 606/9 |
| 2007/0213698 A1 | 9/2007 | Altshuler et al. | 606/12 |
| 2007/0260230 A1 | 11/2007 | Youngquist et al. | 606/9 |
| 2008/0058783 A1 | 3/2008 | Altshuler et al. | 606/9 |
| 2008/0077198 A1 * | 3/2008 | Webb et al. | 607/88 |
| 2008/0139901 A1 | 6/2008 | Altshuler et al. | 600/306 |
| 2008/0172047 A1 | 7/2008 | Altshuler et al. | 606/9 |
| 2008/0262484 A1 | 10/2008 | Hawkins et al. | 606/12 |
| 2008/0294150 A1 | 11/2008 | Altshuler et al. | 606/3 |
| 2009/0069741 A1 | 3/2009 | Altshuler et al. | 604/22 |
| 2009/0131922 A1 | 5/2009 | Dewey et al. | 606/9 |
| 2009/0137996 A1 | 5/2009 | DeBenedictis | 606/9 |
| 2010/0021055 A1 | 1/2010 | Socha | 606/9 |
| 2010/0130969 A1 | 5/2010 | Batterson et al. | 606/9 |
| 2010/0152718 A1 | 6/2010 | Fujikawa | 606/9 |
| 2011/0098691 A1 | 4/2011 | Chan et al. | 606/9 |
| 2012/0022510 A1 | 1/2012 | Welches et al. | 606/3 |
| 2012/0050849 A1 | 3/2012 | Schreiber | 359/371 |
| 2012/0197357 A1 | 8/2012 | Dewey et al. | 607/89 |

OTHER PUBLICATIONS

International PCT Search Report and Written Opinion, PCT/US2012/023894, 12 pages, May 3, 2012.
International PCT Search Report and Written Opinion, PCT/US2012/023880, 12 pages, May 3, 2012.
International PCT Search Report and Written Opinion, PCT/US2012/023887, 12 pages, May 3, 2012.
International PCT Search Report and Written Opinion, PCT/US2012/023890, 12 pages, May 3, 2012.
International PCT Search Report and Written Opinion, PCT/US2012/023885, 12 pages, May 3, 2012.
International PCT Search Report and Written Opinion, PCT/US2012/023893, 12 pages, May 3, 2012.

* cited by examiner

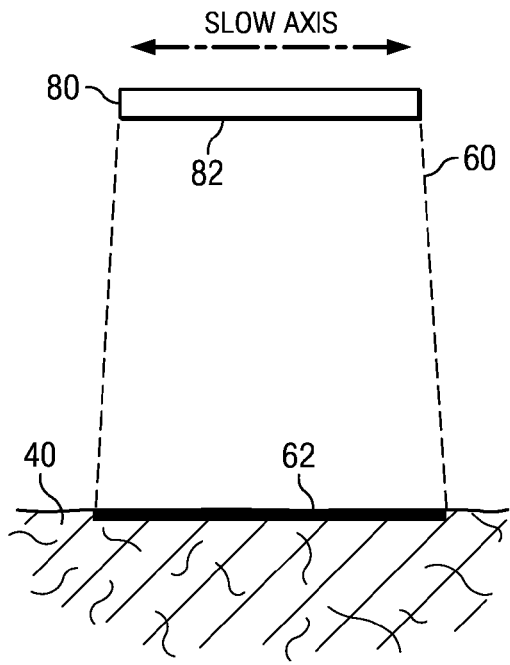 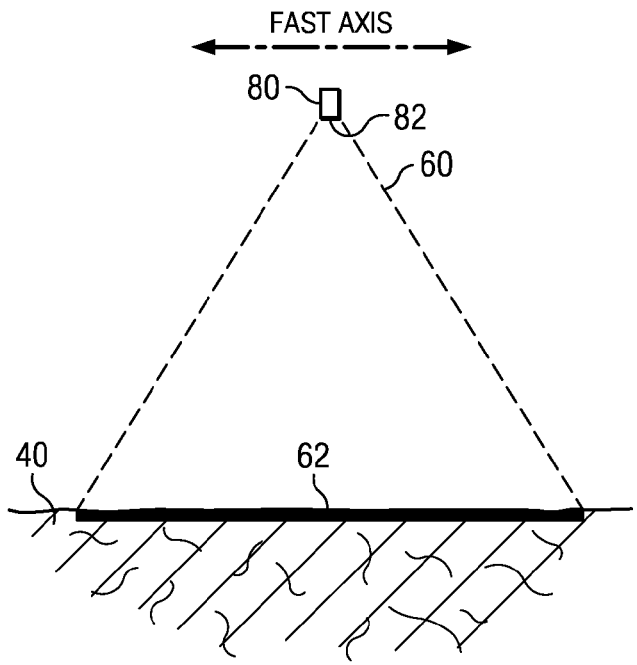
FIG. 18A     FIG. 18B
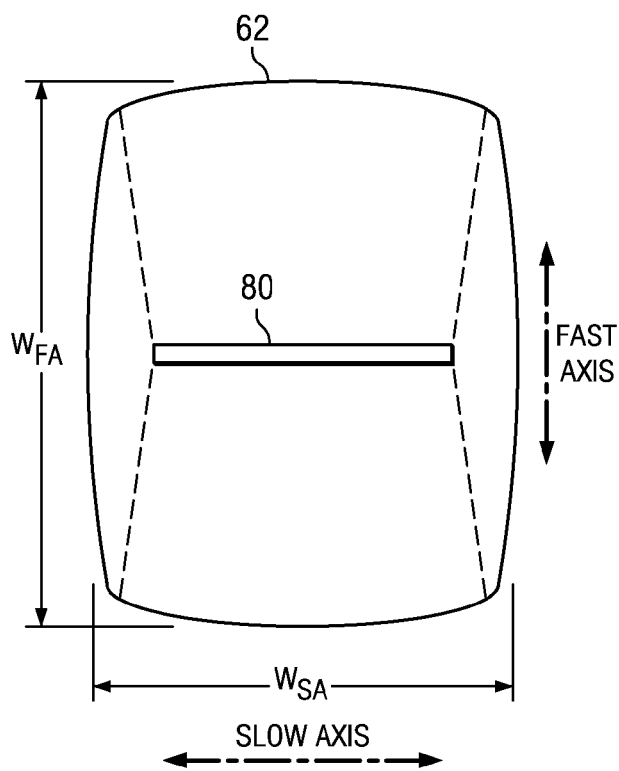
FIG. 18C

PLOT A

RADIATION-BASED DERMATOLOGICAL DEVICES AND METHODS

CROSS-REFERENCE TO RELATED APPLICATIONS

This application claims the benefit of U.S. Provisional Application No. 61/439,353 filed on Feb. 3, 2011; U.S. Provisional Application No. 61/444,079 filed on Feb. 17, 2011; U.S. Provisional Application No. 61/469,316 filed on Mar. 30, 2011; U.S. Provisional Application No. 61/533,641 filed on Sep. 12, 2011; U.S. Provisional Application No. 61/533,677 filed on Sep. 12, 2011; U.S. Provisional Application No. 61/533,786 filed on Sep. 12, 2011; U.S. Provisional Application No. 61/545,481 filed on Oct. 10, 2011; U.S. Provisional Application No. 61/563,491 filed on Nov. 23, 2011; U.S. Provisional Application No. 61/594,128 filed on Feb. 2, 2012; Co-Pending U.S. patent application Ser. No. 13/366,256 filed on Feb. 3, 2012; Co-Pending U.S. patent application Ser. No. 13/366,177 filed on Feb. 3, 2012; Co-Pending U.S. patent application Ser. No. 13/366,202 filed on Feb. 3, 2012; Co-Pending U.S. patent application Ser. No. 13/366,237 filed on Feb. 3, 2012 and Co-Pending U.S. patent application Ser. No. 13/366,246 filed on Feb. 3, 2012; all of which applications are herein incorporated by reference in their entirety.

TECHNICAL FIELD

The present disclosure is related to radiation-based dermatological treatment devices and methods, e.g., laser-based devices for providing fractional treatment, or devices using any other type of radiation source for providing any other suitable type of dermatological treatment.

BACKGROUND

Light-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering light or laser radiation to an area of tissue on a person's body, e.g., the skin or internal tissue, to treat the tissue in a photochemical, photobiological, thermal, or other manner, which can be ablative or non-ablative, among other properties, depending on the particular application.

Light-based treatment devices include various types of light sources, such as lasers, LEDs, flashlamps, etc. For example, diode lasers are particularly suitable for certain light-based treatments and devices for providing such treatments. Diode lasers are compact, as they are typically built on one chip that contains the major necessary components for light generation other than a power source. Further, diode lasers typically provide an efficiency of up to 50% or higher, which enables them to be driven by low electrical power compared to certain other lasers. Diode lasers allow direct excitation with small electric currents, such that conventional transistor based circuits can be used to power the laser.

Other characteristics typical of diode lasers include high temperature sensitivity/tunability, and a highly divergent beam compared to certain other lasers. Diode lasers typically emit a beam having an axis-asymmetric profile in a plane transverse to the optical axis of the laser. In particular, the emitted beam diverges significantly faster in a first axis (referred to as the "fast axis") than in an orthogonal second axis (referred to as the "slow axis"). In contrast, other types of lasers, e.g., fiber lasers, typically emit a beam having an axis-symmetric profile in the transverse plane.

Laser-based treatment devices typically include optics downstream of the laser source to scan, shape, condition, direct, and/or otherwise influence the laser radiation to the target tissue as desired. Such optics may include lenses, mirrors, and other reflective and/or transmissive elements, for controlling optical parameters of the beam, such as the direction, propagation properties or shape (e.g., convergent, divergent, collimated), spot size, angular distribution, temporal and spatial coherence, and/or intensity profile of the beam, for example. Some devices include systems for scanning a laser beam in order to create a pattern of radiated areas (e.g., spots, lines, or other shapes) in the tissue. For some applications, the scanned pattern of radiated areas overlap each other, or substantially abut each other, or are continuous, in order to provide complete coverage of a target area of tissue. For other applications, e.g., certain wrinkle treatments, vascular treatments, pigmentation treatments, anti-inflammatory treatments, and other skin rejuvenation treatments, the scanned radiated areas may be spaced apart from each other by non-irradiated areas such that only a fraction of the overall target area of the tissue is radiated during a treatment session. Thus, in such applications, there are generally regions of untreated tissue between regions of treated tissue. This type of treatment is known as "fractional" treatment (or more specifically, fractional photothermolysis in some cases) because only a fraction of the target area is irradiated during a treatment session.

SUMMARY

The present disclosure is related to radiation-based dermatological treatment devices and methods, e.g., laser-based devices for providing fractional treatment.

In some embodiments, a hand-held compact device is provided for providing radiation-based dermatological treatments, e.g., skin resurfacing, skin rejuvenation, wrinkle treatment, removal or reduction of pigmentation, hair removal, acne treatment, skin tightening, redness, vascular treatments such as telangectasia or port-wine stains, stretch marks, anti-aging, or anti-inflammatory skin treatments such as treating rosacea, acne, or vitiligo. Other embodiments may apply to non-skin tissue treatment, such as eye tissue or internal organs. In particular embodiments, the device is a compact hand-held device for providing laser-based non-ablative fractional treatment by pulsing one or more laser beam sources as the device is moved, or "manually scanned," across the skin, wherein the device omits any optics (e.g., mirrors, powered lenses, etc.) for influencing the laser beams, and wherein the laser beam source(s) along with the laser beam(s) emitted by the laser beam source(s) are attached in a fixed manner (in location and direction) and remain fixed (in location and direction) with respect to the device housing during operation of the device.

The device may include one or more radiation sources that radiate energy to the skin in the form of one or more beams to produce one or more irradiated areas on the skin that provide a dermatological treatment. As used herein, "radiation" may include any radiative energy, including electromagnetic radiation, UV, visible, and IP light, radio frequency, ultrasound, microwave, etc. A radiation source may include any suitable device for radiating one or more coherent or incoherent energy beams, e.g., a laser, LED, flashlamp, ultrasound device, RF device, microwave emitter, etc. Energy beams may be provided in any suitable manner, such as pulsed, continuous wave (CW), or otherwise, depending on the particular embodiment, application, or device setting. In some embodiments, the radiation source is a laser, e.g., an edge emitting laser diode, laser diode bar, HeNe laser, YAG laser, VCSEL laser, or other types of laser, that delivers one or more laser beams to the skin to effect a treatment. It should be understood that references herein to a radiation source or an energy beam in the singular should be interpreted to mean at least one radiation source or at least one energy beam, unless otherwise specified, e.g., references to a single radiation source or a single energy beam, or references to radiation sources or energy beams (or references to multiple radiation sources or multiple energy beams).

In some embodiments, the device provides pulsed energy beams to the skin to provide a fractional dermatological treatment, e.g., skin resurfacing, skin rejuvenation, wrinkle treatment, removal or reduction of pigmentation, treatment of coarse skin caused by photodamage, etc. Each pulsed energy beam forms an irradiated treatment spot (or "treatment spot") on the surface of the skin, and a three-dimensional volume of thermally damaged (or otherwise influenced, such as photochemically) skin extending below the surface of the skin, referred to herein as a micro thermal zone (MTZ). Each MTZ may extend from the skin surface downward into the skin, or may begin at some depth below the skin surface and extend further downward into the skin, depending on the embodiment, device settings, or particular application. The device may be configured to generate an array of MTZs in the skin that are laterally spaced apart from each other by volumes of untreated (i.e., non-irradiated or less irradiated) skin. For example, an application end of the device (also referred to herein as the device "tip") may be manually moved (e.g., in a sliding manner) across the surface of the skin during a treatment session. An energy beam or beams may be pulsed (to generate MTZs in the skin) during the movement of the device across the skin (referred to herein as a "gliding mode" treatment), or between movements of the device across the skin (referred to herein as a "stamping mode" treatment), or a combination of these modes or different modes. The skin's healing response, promoted by the areas of untreated (i.e., non-irradiated) skin between adjacent MTZs, provides fractional treatment benefits in the treatment area (e.g., skin resurfacing or rejuvenation, wrinkle removal or reduction, pigment removal or reduction, etc.). In some embodiments or applications, the compact, hand-held device may yield results similar to professional devices, but leverages a home use model to more gradually deliver the equivalent of a single professional dose over multiple treatments or days (e.g., a 30 day treatment routine or a two treatment sessions per week treatment routine). Skin rejuvenation generally includes at least one or more of treatments for wrinkles, dyschromia, pigmented lesions, actinic kerotosis, melasma, skin texture, redness or erythema, skin tightening, skin laxity, and other treatments.

As used herein, "fractional" treatment means treatment in which individual treatment spots generated on the skin surface are physically separated from each other by areas of non-irradiated (or less irradiated) skin (such that the MTZs corresponding to such treatment spots are generally physically separated from each other). In other words, in a fractional treatment, adjacent treatment spots (and thus their corresponding MTZs) do not touch or overlap each other. In some embodiments in which a radiation source (e.g., laser) is pulsed to generate a successive series of treatment spots on the skin, the pulse rate may be set or selected based on a typical or expected speed at which the device is manually moved or "glided" across the skin, referred to herein as the "manual glide speed" (e.g., in a gliding mode operation of the device). In particular, the pulse rate may be set or selected such that for a range of typical or expected manual (or mechanically-driven) glide speeds, adjacent treatment spots are generally physically separated from each other by areas of non-treated skin (i.e., fractional treatment is provided). In some embodiments, the pulse rate may be set or selected such that for a range of typical or expected manual glide speeds, adjacent treatment spots are physically separated from each other from a predetermined minimum non-zero distance, e.g., 500 μm. For example, in some embodiment, a pulse rate of between 2 and 30 HZ (e.g., about 15 Hz) may be selected for providing a desired fractional treatment for typical or expected manual glide speeds of between 1 and 6 cm/sec.

In some embodiments, the device may be controlled to prevent, limit, or reduce the incidence or likelihood of treatment spot overlap, e.g., based on feedback from one or more sensors (e.g., one or more dwell sensors, motion/speed sensors, and/or displacement sensors). For example, the device may monitor the speed or displacement of the device relative to the skin and control the radiation source accordingly, e.g., by turning off the radiation source, reducing the pulse rate, etc. upon detecting that the device has not been displaced on the skin a minimum threshold distance from a prior treatment location. Further, in some embodiments, the pulse rate may be automatically adjustable by the device and/or manually adjustable by the user, e.g., to accommodate different manual glide speeds and/or different comfort levels or pain tolerance levels of the user.

In some embodiments, the device may be configured to provide 3D fractional treatment, by generating MTZs at various depths in the skin. For example, this may be achieved by providing a plurality of beam sources configured to generate MTZs at different depths, e.g., by using multiple beam sources arranged at different distances from the skin surface, focal depths, wavelengths, pulse energies, pulse durations, or other parameters. Thus, such embodiments may have a solid-state configuration in which the beam sources and the beams propagated from the beam sources remain fixed with respect to the device housing (i.e., no moving parts regarding the beam delivery). As another example, such 3D fractional treatment can be achieved by dynamically moving or adjusting one or more beam sources or output beams, or dynamically adjusting the focal points of one or more beams.

In some embodiments, the device includes a displacement-based control system including a displacement sensor and electronics configured to measure or estimate the lateral displacement of the device across the skin and control one or more aspect of the device (e.g., on/off status or pulse rate of the radiation source) based on the determined displacement of the device. For example, the displacement-based control system may control the delivery of energy beams to provide a desired spacing between treatment spots (for a fractional treatment) and/or to prevent or reduce the incidence or likelihood of treatment spot overlap.

In some embodiments, pulsed energy beams are manually scanned across the skin, rather than using an automated scanning system (e.g., including systems for moving optical elements and/or the laser or other energy source) present in various existing devices. In some embodiments the device does not include any moving optics (or any optics at all, as discussed below). In some embodiments, both the radiation source and energy beam path from the radiation source to the skin are fixed with respect to the outer housing of the device. Omitting an automated scanning system from the device may permit a smaller beam output window or aperture, in particular for embodiment that include only a single beam source, as the emitted energy beam remains fixed relative to the device housing. For example, certain embodiments may include a beam output window or aperture having a maximum width or diameter of less than 1 mm (and in particular embodiments, less than 0.5 mm), as a beam emitted by certain laser sources (e.g., an edge emitting laser diode) typically has a very small diameter (e.g., about 120 microns) and may be fixed such that the beam remains centered in the exit window/aperture. In comparison, certain automated-scanner-based devices have an output window or aperture of greater than one square centimeter in area.

In some embodiments, the device includes a single radiation source, e.g., an edge emitting laser diode, a VCSEL having a single micro-emitter zone, an LED, or a flashlamp. For certain treatments, the single radiation source may be pulsed while the device is glided across the skin to form a generally one-dimensional array (or line) of treatment spots on the skin. A two-dimensional array of treatment spots can thus be created by gliding the device across the skin multiple times in any suitable pattern.

In other embodiments, the device includes multiple radiation sources, e.g., multiple edge emitting laser diodes, an laser diode bar having multiple emitters (or multiple laser diode bars), a VCSEL having multiple micro-emitter zones (or multiple VCSELs), or multiple LEDs. For certain treatments, the multiple radiation sources may be pulsed while the device is operated in a gliding mode or alternatively in a stamping mode or a combination of modes, to form a two-dimensional array of treatment spots on the skin on each glide. Such device may be glided across the skin multiple times to create a larger, more dense, or otherwise different two-dimensional array.

Further, the device may be configured for "direct exposure" or "indirect exposure" radiation, and/or for "close proximity" or "remote proximity" radiation, depending on the particular embodiment and/or configuration of the device. "Direct exposure" embodiments or configurations do not include any optics downstream of the radiation source for affecting or treating the beam(s) generated by the radiation source(s) (the term "optics" is defined below in this document). Some direct exposure devices may include a window (e.g., to protect the radiation source and/or other internal components of the device) that does not substantially affect the beam. A window may be formed from any suitable material, e.g., sapphire, quartz, diamond, or other material transparent at the frequency of the radiation source 14 and preferably also having a good thermal coefficient.

Thus, embodiments of the device may create a desired array of MTZs without using microlenses or other similar optics. Thus, embodiments of the device may provide increased optical efficiency, reduced power requirements, simpler and less expensive manufacturing, increased compactness, and/or enhanced reliability as compared with certain non-ablative fractional treatment devices that use microlenses or other similar optics for creating MTZ arrays. However, it should be understood that certain embodiments of the device may include one or more optics, e.g., for desired beam shaping.

The omission of beam-influencing optics in certain embodiments may result in an overall higher optical efficiency for the device. In any optical system, losses occur due to less than perfect transmission, reflection, or beam "spilling" outside of the diameter of the optical element(s) in the beam path. Thus, embodiments of the device that omit beam-influencing optics may provide increased optical efficiency, and thus allow reduced power to the radiation source(s), as compared with certain conventional devices.

In contrast, "indirect exposure" embodiments or configurations include one or more optics downstream of the radiation source(s) for affecting or treating the beam(s) generated by the radiation source(s). Optics may allow the radiation source(s) to be positioned at any desired distance from the application end of the device that contacts the skin during treatment (and thus at any desired distance from the target surface) or to affect other radiation properties. Certain embodiments that use a laser diode as the radiation source may include one or more fast axis optical elements for capturing and focusing the rapidly diverging fast axis beam profile emitted from the laser diode or a scanner, such as a rotating optic or a microlens array, for suitably delivering/distributing the radiation.

In "close proximity" embodiments or configurations, the emitting surface of each radiation source (e.g., the emitting surface of an edge emitting laser diode) is positioned within 10 mm of the skin-contacting surface of the device (i.e., the leading surface of the device tip), such that the emitting surface of each radiation source is positioned within 10 mm of the skin surface when the device tip is positioned in contact with the skin. As discussed below, this distance is referred to herein as the "proximity gap spacing." In contrast, in "remote proximity" embodiments or configurations, the proximity gap spacing (between the emitting surface of the radiation source(s) and the skin-contacting surface of the device) is greater than 10 mm. Some close proximity embodiments, due to the small proximity gap spacing and thus short travel distance of the beam(s) from the radiation source(s) to the skin, may omit precision-aligned optics (or all optics) that may be needed in similar remote proximity embodiments, thus providing a direct exposure, close proximity configuration. Some particular embodiments discussed below include an edge emitting laser diode configured for direct exposure and close proximity radiation, wherein the emitting surface of the edge emitting laser diode is positioned within 10 mm of the skin surface, with no optics (e.g., only a window, open space, protective coating, or similar feature) between the edge emitting laser diode and the skin. Direct exposure, close proximity embodiments may be particularly compact. Some direct exposure, close proximity embodiments may provide a high optical throughput and may be capable of generating relatively high-power emissions in a compact battery-operated device.

It should be understood that "direct exposure" is not synonymous with "close proximity," and likewise "indirect exposure" is not synonymous with "remote proximity." That is, direct exposure embodiments or configurations may be configured for either close proximity or remote proximity radiation, depending on the particular embodiment or configuration. For example, collimated or quasi-collimated light sources could be located with remote proximity and be direct exposure in that the beam has no optics between the source and the skin. Similarly, indirect exposure embodiments or configurations may be configured for either close proximity or remote proximity radiation, depending on the particular embodiment or configuration. For example, some embodiments may include a very small lens (e.g., a cylindrical or ball lens) downstream of the light source, but wherein the emitting surface of each radiation source is still within 10 mm of the skin surface during treatment.

In some embodiments, the beam generation and delivery components of the device have an all-solid-state construction that excludes any automated or mechanically moving parts for dynamically moving the beam source and direction and location of the propagated beam relative to the device housing, including (a) any motorized or otherwise moving beam-scanning elements, such as motorized or otherwise moving optical elements to scan a beam to multiple different directions or locations relative to the device housing (e.g., galvo-controlled mirrors or rotating multi-faceted scanning elements), and (b) any motorized or other elements for physically moving the beam source and any associated beam delivery elements (e.g., a laser, LED, fiber, waveguide, etc.). Such embodiments may reduces noise, increase the reliability of the device, reduce manufacturing cost and complexity, and/or increase compactness of the finished device with low or minimal component count.

In some embodiments, the device has an all-solid-state construction with no automated moving parts at all, including no any automated or mechanically moving parts for dynamically moving the beam source and direction and location of the propagated beam relative to the device housing (as discussed above), as well as any fans, other motors, or other automated moving parts.

Certain example embodiments are handheld, battery powered, compact skin treatment devices with all solid-state components, configured to provide direct exposure, close-proximity radiation, and for providing skin area coverage via manual scanning of the device across the surface of the skin, in a gliding or stamping mode operation, and using a CW or pulsed radiation source (or multiple CW or pulsed radiation sources).

In some embodiments, the device is fully or substantially self-contained in a compact, hand-held housing. For example, in some battery-powered embodiments of the device, the radiation source(s), user interface(s), control electronics, sensor(s), battery or batteries, fan(s) or other cooling system (if any), and/or any optics (if any), are all contained in a compact, hand-held housing. Similarly, in some wall-outlet-powered embodiments of the device, the radiation source(s), user interface(s), control electronics, sensor(s), battery or batteries, fan(s) or other cooling system (if any), and/or any optics (if any), are all contained in a compact, hand-held housing, with only the power cord extending from the device.

In other embodiments, one or more main components of the device may be separate from the device housing, and connected by any suitable physical or wireless means (e.g., wire, cable, fiber, wireless communications link, etc.)

In some embodiments, the device provides eye safe radiation, e.g., by delivering a substantially divergent energy beam (e.g., using an edge emitting laser diode with no downstream optics), and/or using an eye safety control system including one or more sensors, and/or by any other suitable manner. In some laser-based embodiments or settings, the device meets the Class 1M or better (such as Class 1) eye safety classification per the IEC 60825-1. In other laser-based embodiments or settings, the device falls outside the IEC 60825-1 Class 1M eye safety classification by less than 25% of the difference to the next classification threshold. In still other laser-based embodiments or settings, the device falls outside the IEC 60825-1 Class 1M eye safety classification by less than 50% of the difference to the next classification threshold. In some lamp-based embodiments, the device meets the "Exempt" or "Low Risk" eye safety classification per the IEC 62471.

In some embodiments, the device uses one or more VCSEL (Vertical Cavity Surface Emitting Laser) lasers as the radiation source(s). A VCSEL may be configured to generate a single energy beam or multiple discrete energy beams. For the latter, the VCSEL may include non-active regions that define an array of micro-emitter zones separated from each other by non-active (or less active or masked) regions, with each micro-emitter zone generating a beam, such that a single VCSEL may generate an array (e.g., a 1D or 2D array) of laser beams. In some embodiments, the array of laser beams is delivered to the skin to provide an array of spaced-apart treatment spots on the skin, and thus an array of spaced-apart MTZs, e.g., to provide a fractional treatment via a manual gliding mode or stamping mode operation of the device. In some embodiments, the beam generated from each micro-emitter zone is substantially axially-symmetric (e.g., as opposed to the beam generated by an edge emitting laser diode). In some embodiments, a two-dimensional multi-zone pulsed VCSEL may be configured in direct exposure, close proximity (in effect, placed directly or nearly directly against the skin) to affect a fractional treatment when glided or stamped across the skin. Likewise, a one-dimensional, multi-zone pulsed VCSEL can be configured in direct exposure, close proximity to affect a fractional treatment when glided or stamped across the skin.

In some embodiments, the device is eye safe, hand held, manufacturable without excessive labor costs, requires low power consumption, and effective. In some embodiments, the device eliminates the need for optical scanners, microlenses, or other complex optical and mechanical devices, for creating multiple MTZs in the skin. In particular embodiments, the device is battery powered, with a single, fixed location, repetitively-pulsed edge emitting laser diode for creating an array of MTZs in the skin by manually scanning the device across the skin while the edge emitting laser diode is repetitively pulsed, with each pulse creating a single MTZ in the skin. In other embodiments, multiple beam sources (e.g., multiple edge emitting laser diodes, certain laser diode bars, certain VCSEL configurations) multiple can be used to create multiple MTZs in the skin for each pulse of the multiple beam sources.

In some embodiments, the device may be suitable for providing a fractional treatment using a home-use treatment plan that includes treatment sessions of a few minutes or less, once or twice a day. In some embodiments, a treatment session of two minutes, for example, may allow an effective treatment of about 20-30 cm$^2$ (about 4 in$^2$). Further, certain embodiments permits the use a small battery, and allow for thermal control without any fan(s). For example, in some embodiments, a small cylindrical block of copper can absorb the waste heat from a laser during a treatment session, preventing excessive temperature rise of the diode without the use of a fan. Other embodiments may include at least one fan for increased cooling of the device components.

BRIEF DESCRIPTION OF THE DRAWINGS

Some embodiments of the disclosure may be understood by referring, in part, to the following description and the accompanying drawings wherein:

FIGS. 18A-18C illustrate the asymmetrical divergence of a beam emitted from an edge emitting laser diode, in embodiments with a larger proximity gap spacing.

DETAILED DESCRIPTION OF THE DRAWINGS

Some embodiments of the disclosure may be understood by referring, in part, to the following description and the accompanying drawings, in which like reference numbers refer to the same or like parts.

Figure 1:
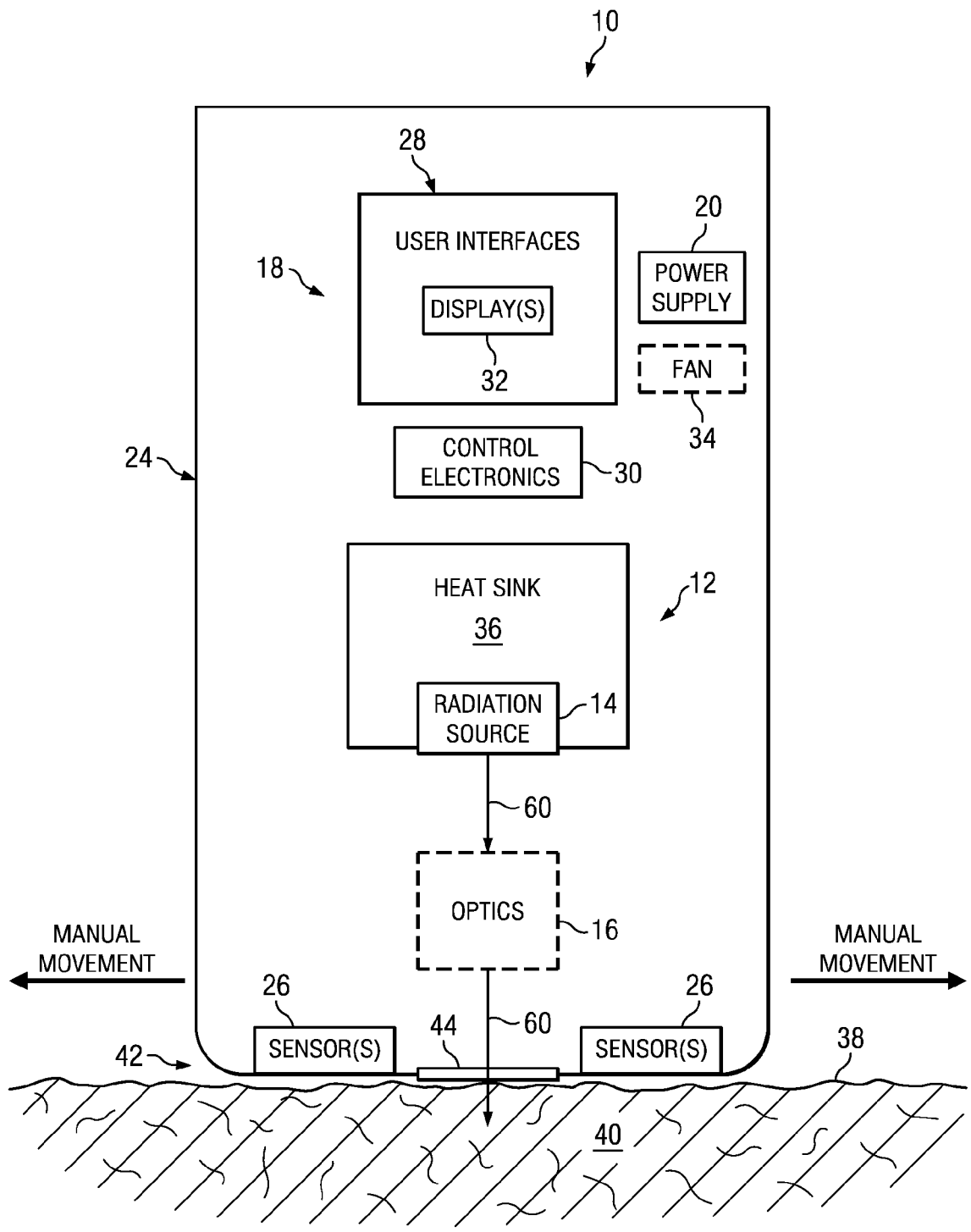
FIG. 1 illustrates components of an example radiation-based treatment device, according to certain embodiments.

FIG. 1 illustrates various components of an example held-held radiation-based treatment device 10, according to certain embodiments. Radiation-based treatment device 10 may include a radiation engine 12 including a radiation source 14 configured to generate an energy beam 60, optics 16 for conditioning and/or delivering the energy beam 60 to a treatment area of skin 40, control systems 18, one or more power supplies 20, and/or one or more fans 34.

As discussed above, "direct exposure" embodiments of device 10 may omit optics 16 such that no significant optics are provided between radiation source 14 and the skin surface, thus providing direct radiation of the skin. Further, as discussed above, in some direct exposure embodiments, the emitting surface of radiation source 14 is located in close proximity (within 10 mm) of the skin-contacting surface of the treatment tip of the device or target tissue 40.

In some embodiments, the main components of device 10 may be substantially self-contained in a held-held structure or outer housing 24. Held-held housing 24 may define an application end (or "treatment tip") 42 configured to be placed in contact with the skin (or other target surface) during treatment of a treatment area of skin 40. Application end 42 may include or house various user interfaces, including the treatment delivery interface for delivering energy beam 60 to the user, as well as one or more sensors 26 for detecting various characteristics of the skin (or other surface) and/or energy delivered by device 10. In some embodiments, application end 42 may include an aperture or window 44 through which the laser beam is delivered to the target surface, or alternatively, an optical element 16 (e.g., a lens) may be located at application end 42 and configured for direct contact or close proximity with the skin during treatment.

Device 10 may include any other components suitable for providing any of the functionality discussed herein or other related functionality known to one of ordinary skill in the art.

Radiation engine 12 may include one or more radiation sources 14, such as one or more lasers, LEDs, and/or flashlamps, ultrasound devices, RF devices, or microwave emitters, for example. Embodiments including lasers as the radiation source 14 may include any type or types of lasers, e.g., one or more edge emitting laser diodes (single emitter edge emitting laser diodes or multiple emitter edge emitting laser diodes), laser diode bars, VCSEL lasers (Vertical Cavity Surface Emitting Lasers), $CO_2$ lasers, Erbium YAG lasers, pulsed dye lasers, fiber lasers, other types of lasers, or any combination thereof.

Radiation source 14 may include one or more beam source, each operable to generating a beam for delivery to the skin. In some embodiments, radiation source 14 is a laser having exactly one beam source for generating a single beam, for example (a) a single-emitter edge emitting laser diode that generates a single beam, (b) a multi-emitter edge emitting laser diode that generates a single collective beam, e.g., as described in co-pending U.S. Provisional Patent Application 61/594,128, the entire contents of which are hereby incorporated by reference, (c) a laser diode bar with high fill factor to generate a single collective beam or single beam with spatial modulation of its energy profile, e.g., as discussed below, or (d) a VCSEL laser having multiple emitters that together act as a single beam source (i.e., a single "micro-emitter zone") to generate a single combined beam. Item (b) "a multi-emitter edge emitting laser diode that generates a single collective beam" refers to an integral or monolithic laser diode structure having multiple emitter junctions formed on a substrate (such as, for example, a "multiple quantum well" (MQW) laser diode), and is thus distinguished from a laser diode bar.

In other embodiments, radiation source 14 is a laser having multiple beam sources for generating multiple discrete beams, for example (a) an laser diode bar having multiple emitters, each generating a single discrete beam, or (b) a VCSEL laser having multiple micro-emitter zones (with one or more emitter per zone), with each micro-emitter zone acting as a discrete beam source to generate a single beam discrete from the others. Such multiple beam sources may be arranged in a row, a two-dimensional array, or otherwise.

In some embodiments, the beam emitted from each beam source diverges in at least one direction. For example, in embodiments including a single-beam source edge emitting laser diode or multi-beam source laser diode bar, the beam emitted from each beam source may diverge in both a fast axis and a slow axis. Thus, in such embodiments, if the device includes no optics downstream of the beam source(s), the energy beam(s) exit the application end of the device, and reach the target surface as an asymmetrically diverging beam. Further, in embodiments including a VCSEL laser, the emitted beam or beams may diverge symmetrically in both axes, e.g., by about 15 degrees.

As discussed below, the divergence of energy beams delivered by such embodiments of device 10 may provide an aspect of eye-safety. In some embodiments, the arrangement of radiation source 14 and/or the divergence of the beam(s) emitted from the light source may provide Class 1M or better eye safety classification per the IEC 60825-1 standard, as discussed below.

In some embodiments, radiation source 14 may be configured for and/or operated at any suitable wavelength to provide the desired dermatological treatment. For example, radiation source 14 may be a laser configured for and/or operated at a wavelength that is absorbed by water in the skin, e.g., between 1400 nm and 2000 nm, e.g., for certain photothermolysis or other treatments. In some embodiments, radiation source 14 may be a laser configured for and/or operated at a wavelength of between 1400 nm and 1550 nm, e.g., for acne treatment or certain fractional non-ablative skin treatments, e.g., skin rejuvenation or resurfacing, wrinkle treatment, or treatment of pigmented legions (e.g., age spots, sun spots, moles, etc.). In other embodiments, radiation source 14 may be a laser configured for and/or operated at a wavelength of between 1700 nm and 1800 nm, e.g., for sebaceous gland related treatment like acne. In still other embodiments, radiation source 14 may be a laser configured for and/or operated at a wavelength of about 1926 nm, e.g., for pigmented lesion treatment like solar lentigo. As another example, radiation source 14 may be a laser configured for and/or operated at a wavelength of about 810 nm for providing hair removal treatment or melanin-based treatments. In some embodiments that include multiple beam sources, different beam sources may emit light at different wavelengths. For example, a device may include one or more first beam sources that emit a wavelength of about 1400 nm-1550 nm and one or more second beam sources that emit a wavelength of about 1926 nm. As another example, the wavelength may be in the UV (e.g., such as to effect DNA or micro-organisms), may be in the visible spectrum (e.g., such as to affect melanin, hemoglobin, oxyhemoglobin, or photosensitive elements like mitochondria or fibroblasts) or in the IR spectrum (e.g., such as to affect melanin, water, lipids). Likewise, the radiation may be in the ultrasound spectrum (e.g., such as to perform focused ultrasound fractional skin rejuvenation or tightening) or in the radio frequency spectrum (e.g., such as to perform fractional or bulk heating).

Radiation source 14 may be configured for or operated at any suitable energy or power level. For example, in some embodiments, radiation source 14 may emit a total energy of between about 2 mJ and about 30 mJ per beam (i.e., per treatment spot). For example, radiation source 14 may emit between about 5 mJ and about 20 mJ per beam. In particular embodiments, radiation source 14 emits about 15 mJ per beam.

Further, radiation source 14 may deliver continuous wave (CW) radiation, pulsed radiation, or in any other manner, depending on the particular embodiment, application, or device setting. For the purposes of this disclosure, pulsed or continuous wave radiation refers to the radiation delivered out of application end 42 of device 10. Thus, radiation may be pulsed either by pulsing the radiation source 14, by intermittently blocking the energy beam emitted by radiation source 14, or otherwise intermittently enabling and disabling the delivery of radiation out of application end 42.

In some embodiments, device 10 controls radiation source 14 to provide CW or quasi-CW radiation, e.g., for bulk heating skin tightening, hair removal, or acne treatment. In other embodiments, device 10 provides pulsed radiation (e.g., by controlling pulsing radiation source 14, by intermittently blocking the energy beam emitted by radiation source 14, or otherwise), e.g., for fractional treatment. For example, in some embodiments, device 10 may be a laser-based device configured to sequentially deliver a series of laser beams to the treatment area 40 to generate treatment spots that are spaced apart from each other by areas of non-irradiated skin between the adjacent treatment spots, to provide a fractional treatment to the skin. Such embodiments may utilize any suitable pulse parameters, e.g., pulse rate or frequency, pulse on time, pulse off time, duty cycle, pulse profile, etc. In some embodiments, radiation source 14 may be pulsed at a rate between 0.5 and 75 Hz. For example, radiation source 14 may be pulsed at a rate between 2 and 30 Hz. In particular embodiments, radiation source 14 may be pulsed at a rate between 10 and 20 Hz, e.g., about 15 Hz. The energy per pulse on a given treatment spot can be achieved by a single pulse or by multiple repetitive pulses.

As used herein, a "pulse" may include both (a) a single, continuous burst of radiation, and (b) one or more higher-frequency pulses at substantially the same location (i.e., with substantially overlapping areas of irradiation at the target plane), sometimes referred to as a modulated pulse, pulse train, or super pulse. If the time interval between the pulses in a pulse train is shorter than the relaxation time of the mechanism of action (e.g., shorter than the thermal relaxation time of a photothermolysis chromophore target), then the pulse train can deliver substantially similar results as a single longer pulse.

As used herein, a "treatment spot" means a contiguous area of skin irradiated by a beam source—during a continuous period of irradiation or during a pulse (as defined above)—to a degree generally sufficient to provide a desired treatment in the skin at that location. For some types of beam source, including laser beam sources for example, the boundaries of the treatment spot are defined by the "$1/e^2$ width," i.e., the treatment spot includes a contiguous area of the skin surface that is irradiated by a radiation intensity equal to at least $1/e^2$ (or 0.135) times the maximum radiation intensity at any point on the skin surface. A treatment spot may include the full extent of the surface (or volume) irradiated. A treatment spot may include the full extent of the tissue being influenced by the irradiation, which may be smaller than the irradiated area or volume, or may be larger (e.g., due to thermal conductivity). Further, reference to a treatment spot "on the skin" or similar language refers to radiation pattern on the skin which generally produces a radiation pattern within the skin, whether or not it produces a treatment effect on the surface of the skin.

A treatment spot includes any increased areas due to smearing, blurring, or other elongation in any one or more direction due to movement of the device across the skin, whether the radiation source is providing pulsed or continuous wave (CW) radiation. Thus, if the device is moved across the skin during CW radiation (e.g., in a gliding mode operation), a treatment spot may be many times larger than the size of the instantaneous irradiated area of skin. If the device is moved across the skin during pulsed radiation (e.g., in a gliding mode operation), a treatment spot may be, for example, 10% to 500% larger than the size of the instantaneous irradiated area of skin, depending on a number of factors.

Certain embodiments of device 10 include one or more optics 16 downstream of radiation source 14 for directing or treating the beam 60 emitted from radiation source 14 before reaching the target surface. Optics 16 may allow for radiation source 14 to be positioned at any desired distance from the application end 42 of the device that contacts the skin during treatment (and thus at any desired distance from the target surface). Embodiments of device 10 that include optics 16 downstream of radiation engine 12 are referred to herein as "indirect exposure" embodiments.

Optics 16 may include any number and types of optical elements, e.g., lenses, mirrors, and other elements, for delivering the light generated by radiation engine 12 to the treatment area 40 and, if desired, for treating the beam, such as adjusting the treatment spot 62 size, intensity, treatment spot location, angular distribution, coherence, etc.

As used herein, an "optic" or "optical element" may mean any element that deflects a light beam, influences the angular distribution profile (e.g., angle of convergence, divergence, or collimation) of a beam in at least one axis, influences the focus of the beam in at least one axis, or otherwise affects a property of the radiation. Thus, optics include mirrors and other reflective surfaces, lenses, prisms, light guides, gratings, filters, etc. For the purposes of this disclosure, optics do not generally include planar or substantially planar transmissive elements such as transmissive windows or films, such as those that serve as transmissive aperture that protect internal components.

Other embodiments of device 10 do not include any optics 16 downstream of radiation source 14 for affecting or treating the beam. Such embodiments are referred to herein as "direct exposure" embodiments. Some direct exposure devices may include a window (e.g., to protect radiation source 14 and/or other internal components of device 10) that does not substantially affect the beam 60. In some embodiments (e.g., certain embodiments including one or more edge emitting laser diodes as the radiation source 14), the radiation source 14 may be positioned very close to the application end 42 of the device that contacts the skin during treatment (and thus very close to the target surface). For example, in some direct exposure devices, the radiation source 14 may be positioned such that the emitting surface of the radiation source 14 is less or equal to 10 mm from the skin when the application end 42 is placed in contact with the skin, referred to herein as close proximity embodiments.

Control systems 18 may be configured to control one or more components of device 10 (e.g., radiation engine 12, fans 34, displays 32, etc.). Control systems 18 may include, for example, any one or more of the following: a radiation source control system for controlling aspects of the generation, treatment, and delivery of energy beams 60 to the user; a displacement-based control system for controlling aspects of device 10 based on the determined displacement of device 10 across to the skin (e.g., as device is glided across the skin during treatment), e.g., relative to a prior treatment position; a temperature control system; an eye safety control system to help prevent exposure of the eyes (e.g., the corneas) to the treatment radiation (an eye safety control system may be omitted in embodiments in which the laser radiation emitted from device 10 is inherently eye-safe, e.g., certain direct exposure embodiments of device 10); and/or a battery/power control system.

Control systems 18 may include one or more sensors 26 and/or user interfaces 28 for facilitating user interaction with device 10, and control electronics 30 for processing data (e.g., from sensors 26 and/or user interfaces 28) and generating control signals for controlling various components of device 10. Control electronics 30 may include one or more processors and memory devices for storing logic instructions or algorithms or other data. Memory devices may include any one or more device for storing electronic data (including logic instructions or algorithms), such as any type of RAM, ROM, Flash memory, or any other suitable volatile and/or non-volatile memory devices. Logic instructions or algorithms may be implemented as software, firmware, or any combination thereof. Processors may include any one or more devices, e.g., one or more microprocessors and/or microcontrollers, for executing logic instructions or algorithms to perform at least the various functions of device 10 discussed herein. Control electronics 30 may include exclusively analog electronics or any combination of analog and digital electronics.

Control systems 18 may control components or aspects of device 10 based on feedback from sensors 26, user input received via user interfaces 28, and/or logic instructions/algorithms. For example, in some embodiments, control systems 18 may control the operation of radiation engine 12 based at least on feedback from a displacement sensor. Thus, for example, control systems 18 may control radiation engine 12 based on signals from a displacement sensor indicating that device 10 or treatment tip 42 has been translated a certain distance across treatment area 40 from a prior treatment position.

Control systems 18 may include, for example, a radiation source control system for controlling aspects of the generation, treatment, and delivery of energy beams 60 to the user; a displacement-based control system for controlling aspects of device 10 based on the determined displacement of device 10 across the skin (e.g., as device is glided across the skin during treatment), e.g., relative to a prior treatment position; a temperature control system; an eye safety control system to help prevent exposure of the eyes (e.g., the cornea) to the treatment radiation; and a battery/power control system. Such control systems 18 are discussed in greater below with reference to FIG. 2 and subsequent figures.

More specifically, control systems 18 may be configured to control one or more operational parameters of device 10. For example, control systems 18 may control the treatment level (e.g., low power level, medium power level, or high power level) or treatment mode (e.g., gliding mode vs. stamping mode; or rapid-pulse mode vs. slow-pulse mode; or initial treatment mode vs. subsequent treatment mode; etc.), the status of radiation source 14 (e.g., on/off, pulse-on time, pulse-off time, pulse duty cycle, pulse frequency, temporal pulse pattern, etc.), parameters of the radiation (e.g., radiation wavelength, intensity, power, fluence, etc.), the configuration or operation of one or more optical elements (in certain indirect exposure embodiments), and/or any other aspects of device 10.

Sensors 26 may include any one or more sensors or sensor systems for sensing or detecting data regarding device 10, the user, the operating environment, or any other relevant parameters. For example, as discussed in greater detail below with respect to FIG. 2, sensors 26 may include one or more of the following types of sensors: (a) one or more displacement sensor for determining the displacement of device 10 relative to the skin, (b) one or more motion/speed sensor for determining the speed, rate, or velocity of device 10 moving ("gliding") across the skin, (c) one or more skin-contact sensor for detecting proper contact between device 10 and the skin, (d) one or more pressure sensor for detecting the pressure of device 10 pressed against the skin, (e) one or more temperature sensor for detecting the temperature of the skin, a region of the skin, and/or components of device 10, (f) one or more radiation sensor for detecting one or more parameters of radiation (e.g., intensity, fluence, wavelength, etc.) delivered or indicative of delivered to the skin, (g) one or more color/pigment sensor for detecting the color or level of pigmentation in the skin, (h) one or more eye safety sensor for preventing unwanted eye exposure to light from radiation source 14, (i) one or more dwell sensor for detecting if the device is stationary or essentially stationary with respect to the skin, (j) one or more roller-type sensors for detecting the displacement and/or glide speed of the device, and/or any (k) other suitable types of sensors.

User interfaces 28 may include any systems for facilitating user interaction with device 10. For example, user interfaces 28 may include buttons, switches, knobs, sliders, touch screens, keypads, devices for providing vibrations or other tactile feedback, speakers for providing audible instructions, beeps, or other audible tones; or any other methods for receiving commands, settings, or other input from a user and providing information or output to the user. User interfaces 28 may also include one or more displays 32, one or more of which may be touch screens for receiving user input. One or more user interfaces 28 or portions thereof may be included in a separate housing from the treatment device, such as in a smart charging dock or a personal computer, and the treatment device may communicate with the separate housing via hardwire (such as a cable or jack), wireless methods (such as infrared signals, radio signals, or Bluetooth), or other suitable communication methods.

Power supplies 20 may include any one or more types and instances of power supplies or power sources for generating, conditioning, or supplying power to the various components of device 10. For example, power supplies 20 may comprise one or more rechargeable or non-rechargeable batteries, capacitors, super-capacitors, DC/DC adapters, AC/DC adapters, and/or connections for receiving power from an outlet (e.g., 110V wall outlet). In some embodiments, power supplies 20 include one or more rechargeable or non-rechargeable batteries, e.g., one or more Li containing cells or one or more A, AA, AAA, C, D, prismatic, or 9V rechargeable or non-rechargeable cells.

Control Systems

Figure 2:
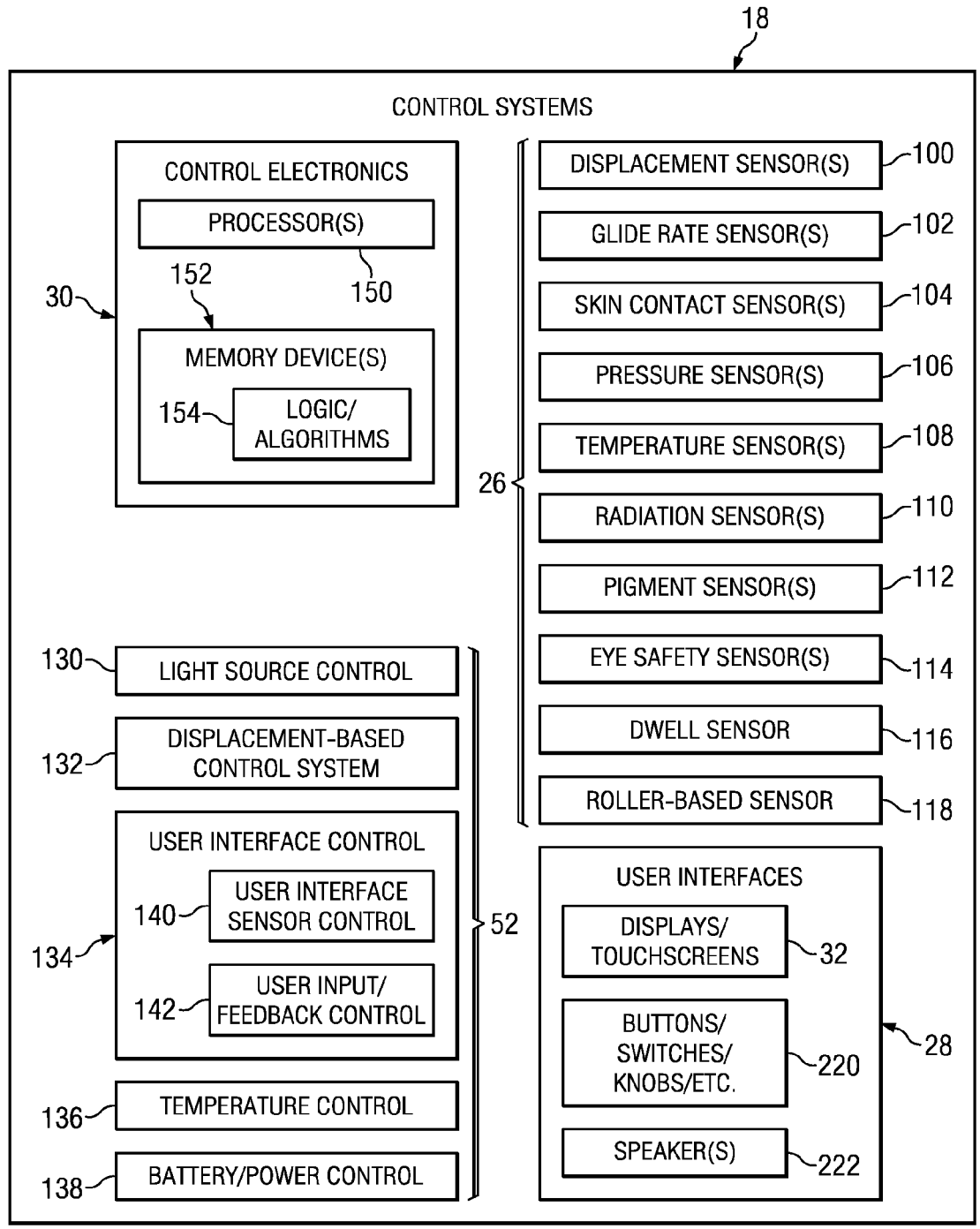
FIG. 2 illustrates an example control system for a radiation-based treatment device, according to example embodiments.

FIG. 2 illustrates example components of control systems 18 for controlling aspects of device 10, according to certain embodiments. Control systems 18 may include control electronics 30, sensors 26, user interfaces 28, and a number of control subsystems 52. Control subsystems 52 are configured to control one or more components of device 10 (e.g., radiation engine 12, fans 34, displays 32, etc.). In some embodiments, control subsystems 52 may include a radiation source control system 130, a displacement-based control system 132, a user interface control system 134, a temperature control system 136, a battery/power control system 138, and/or any other suitable control systems for controlling any of the functionality disclosed herein. User interface control system 134 may include a user interface sensor control system 140 and a user input/display/feedback control system 142.

Each control subsystem 52 may utilize any suitable control electronics 30, sensors 26, user interfaces 28, and/or any other components, inputs, feedback, or signals related to device 10. Further, any two or more control systems may be at least partially integrated. For example, the functionality of control systems 130-138 may be at least partially integrated, e.g., such that certain algorithms or processes may provide certain functionality related to multiple or all control systems 130-138.

Each control subsystem 52 (e.g., subsystems 130-138) may be configured to utilize any suitable control electronics 30, sensors 26, and user interfaces 28. In some embodiments, control electronics 30 may be shared by more than one, or all, control subsystems 52. In other embodiments, dedicated control electronics 30 may be provided by individual control subsystems 52.

Control electronics 30 may include one or more processors 150 and memory device 152 for storing logic instructions or algorithms 154 or other data. Memory devices 152 may include any one or more device for storing electronic data (including logic instructions or algorithms 154), such as any type of RAM, ROM, Flash memory, or any other suitable volatile and/or non-volatile memory devices. Logic instructions or algorithms 154 may be implemented as hardware, software, firmware, or any combination thereof. Processors 150 may include any one or more devices, e.g., one or more microprocessors and/or microcontrollers, for executing logic instructions or algorithms 154 to perform at least the various functions of device 10 discussed herein. Control electronics 30 may include exclusively analog electronics or any combination of analog and digital electronics.

Sensors 26 may include any one or more sensors or sensor systems for sensing or detecting data regarding device 10, the user, the operating environment, or any other relevant parameters. For example, sensors 26 may include one or more of the following types of sensors:

(a) At least one displacement sensor 100 for detecting, measuring, and/or calculating the displacement of device 10 relative to the skin 40, or for generating signals from which the displacement is determined. In some embodiments, e.g., as discussed below with reference to FIGS. 37-43, displacement sensor 100 may be a single-pixel sensor configured to determine a displacement of device 10 by identifying and counting intrinsic skin features in the skin. In other embodiments, e.g., as discussed below with reference to FIGS. 44-45, displacement sensor 100 may be a multiple-pixel sensor, such as a mouse-type optical imaging sensor utilizing a two-dimensional array of pixels.

In other embodiments, e.g., as discussed below with reference to FIGS. 46A-46F, displacement sensor 100 may be a roller-type sensor 118 in which the amount of roller rotation indicates the linear displacement of the device. For example, a roller-type sensor displacement sensor 100 may include a mechanical roller having one or more indicia, a detection device (e.g., an optical or other scanner) for identifying such indicia as they roll past the detection device, and processing electronics for determining the displacement of device 10 based on the detection of such indicia. In some embodiment, the roller may also be actively driven by a motor to facilitate a gliding treatment.

In still other embodiments, displacement sensor 100 may comprise a capacitive sensor, as described below. Displacement sensor 100 may use any number of other devices or techniques to calculate, measure, and/or calculate the displacement of device 10.

Displacement sensor 100 may be used for (i) detecting, measuring, and/or calculating linear displacements of device 10 in one or more directions, (ii) detecting, measuring, and/or calculating the degree of rotation travelled by device 10 in one or more rotational directions, or (iii) any combination thereof.

(b) At least one motion/speed sensor 102 for detecting, measuring, and/or calculating the rate, speed, or velocity of device 10 moving across the treatment area 40 (the "manual glide speed"), or for generating signals from which the manual glide speed is determined;

(c) At least one skin-contact sensor 104 for detecting contact between device 10 and the skin or treatment area 40. For example, device 10 may include one or more capacitive contact sensors 104 for detecting contact with the user's skin.

(d) At least one pressure (or force) sensor 106 for detecting the pressure (or force) of device 10 against the skin or treatment area 40.

(e) At least one temperature sensor 108 for detecting the temperature of the treatment area 40, a region of the treatment area 40 (such as the treatment spot 62 before, during, and/or after treatment), components of device 10, or other object.

(f) At least one radiation sensor 110 for detecting levels or other parameters of radiation delivered to the treatment area 40 or indicative of the radiation delivered to the treatment area 40 (e.g., per light pulse, per individual beam/treatment spot, per delivered array of scanned beams/treatment spots 62, per a specific number of individual delivered beams/treatment spots 62 or scanned arrays of beams/treatment spots 62, or per a specific time period). For example, device 10 may include a photodiode to measure the pulse duration of the treatment beam.

(g) At least one color/pigment sensor 112 for detecting the color or level of pigmentation in the treatment area 40.

(h) At least one eye safety sensor 114 for helping to prevent unwanted eye exposure to light from the treatment radiation source 14. Example eye safety sensors 114 are discussed below with reference to FIGS. 48-51.

(i) At least one dwell sensor 116 for detecting whether device 10 is stationary or essentially stationary with respect to the skin.

(j) At least one roller-based sensor 118 that may be used as a displacement sensor 100, a motion/speed sensor 102, a dwell sensor 116 or all, for detecting signals indicative of the displacement of device 10, the manual glide speed of device 10, or stationary status of device 10, or both.

(k) any other type of sensors.

User interfaces 28 may include any systems for facilitating user interaction with device 10, e.g., displaying data or providing feedback to a user visually and/or audibly, and/or palpably (e.g., via vibration), and receiving commands, selections, or other input from the user. For example, user interfaces 28 may include one or more displays 32 (one or more of which may be interactive touch screens), one or more manual devices 160 (e.g., buttons, switches, knobs, sliders, touch screens, keypads, etc.), one or more speakers 162, and/or any other devices for providing data, information, or feedback to a user or receiving input or information from a user.

Control subsystems 52 may be configured to control one or more controllable operational parameters of device 10, based on feedback from sensors 26, user input received via user interfaces 28, and/or execution of logic instructions/algorithms 154. As used herein, "controllable operational parameters" may include any aspects or parameters of device 10 that may be controlled by any of control subsystem 52.

For example, one or more control subsystems 52 may control any aspects of the operation of radiation source 14, such as for example:

(a) selecting and/or switching the treatment mode (discussed below), (b) controlling the on/off status of radiation engine 12 (which may involve controlling individual light sources separately or as a group), and the timing of such on/off status: e.g., pulse-on time (pulse width), pulse-off time, pulse duty cycle, pulse frequency, temporal pulse pattern, etc., (c) controlling one or more parameters of the radiation: e.g., wavelength, intensity, power, fluence, etc. (e.g., by controlling the power supplied to radiation engine 12), and/or (d) controlling any other aspect of radiation source 14.

Control subsystems 52 (e.g., control systems 130-138) may control components or aspects of device 10 based on feedback from sensors 26, user input received via user interfaces 28, and/or logic instructions/algorithms 154. For example, in some embodiments, control system 130 may control the operation of radiation source 14 based on feedback from a displacement sensor 100 and skin contact sensor(s) 104. As another example, control system 130 may control the operation of radiation source 14 based on feedback from a displacement sensor 100, skin contact sensors 104, and an eye safety sensor 114. In other embodiments, control system 130 may control the operation of radiation source 14 based on feedback from a glide rate sensor 102 and skin contact sensor (s) 104. In other embodiments, control system 130 may control the operation of radiation source 14 based on feedback from a dwell sensor 116 and skin contact sensor(s) 104. In other embodiments, control system 130 may control the operation of radiation source 14 based on feedback from both a displacement sensor 100 or dwell sensor 116 and a glide rate sensor 102, in addition to one or more other sensors 104-116.

Figure 3:
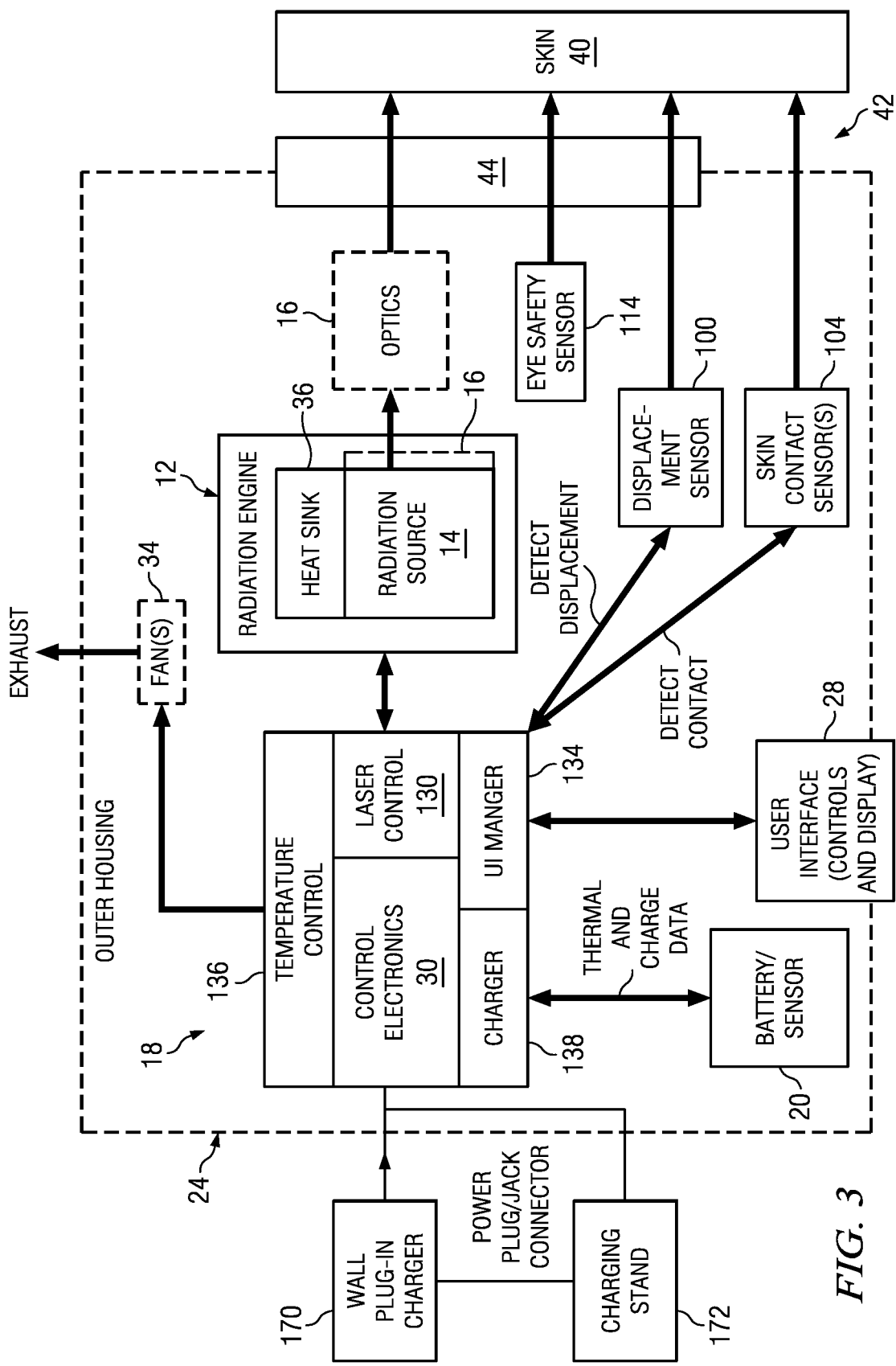
FIG. 3 illustrates a schematic layout of various components of a radiation-based treatment device, according to example embodiments.

FIG. 3 illustrates a functional block diagram of an example device 10, according to certain example embodiments. Device 10 may include various components contained in a housing 24, including a radiation engine 12, optics 16 (omitted in certain embodiments, as discussed herein), control systems 18, displays 32, a power source (in this example, a battery) 22, various sensors 26, and a cooling fan 34 (omitted in certain fully-solid-state embodiments, as discussed herein).

Radiation engine 12 may include one or more radiation sources 14 (e.g., one or more lasers), a heat sink or other cooling system 36, and in some embodiments, optics 16 (e.g., a fast-axis cylindrical lens coupled to a laser package and positioned immediately downstream of an edge emitting laser diode).

As discussed above, optics 16 (which are excluded in direct exposure embodiments, as discussed herein) may include any number and types of optical elements, e.g., lenses, mirrors, and other elements, for delivering (e.g., directing and/or routing) an energy beam 60 from radiation engine 12 to the treatment area 40 and/or for treating the beam 60, such as adjusting the treatment spot size, intensity, treatment spot location, angular distribution, coherence, etc.

In the illustrated embodiment, device 10 may include a displacement sensor 100, skin contact sensor(s) 104, and/or an eye safety sensor 114 (and/or other sensors discussed herein). Displacement sensor 100 may monitor the lateral displacement of device 10 relative to the skin, e.g., as device 10 is moved across the skin in a gliding mode or stamping mode of operation. Skin contact sensors 104 may determine whether device 10, in particular an application end (or "treatment tip") 42, is in contact with or sufficiently close to the skin for providing treatment to the user. Eye safety sensor 114 may determine whether the application end 42 of device 10, e.g., a treatment window 44 or output aperture, is positioned over the skin or the cornea, such that device 10 be controlled (e.g., radiation source 14 turned off) when the cornea is detected, in order to prevent unintended exposure of the cornea.

As discussed above, control systems 18 may include any suitable subsystems for controlling the various components and aspects of device 10. In this example, control systems 18 include a radiation source control system 130, a displacement-based control system 132, a user interface control system 134, a temperature control system 136, and a battery/charger control system 138. Each control subsystem 130-138 may utilize or interact with control electronics 30, sensors 26 (e.g., sensors 100, 104, and/or 114), and user interfaces 28.

Radiation source control system 130 may monitor and control various aspects of radiation source 14. For example, system 130 may turn radiation source 14 on and off, and monitor and control the intensity of generated light or other radiation (e.g., by controlling the current to radiation source 14). As another example, in embodiments or configurations in which radiation source 14 is pulsed, system 130 may monitor and/or control the pulse frequency, pulse on time, pulse off time, pulse duration, pulse wave profile, duty cycle, or any other parameters of the pulsed delivery. As another example, system 130 may monitor the temperature of laser radiation source 14, which data may be used by temperature control system 136, e.g., for controlling fan 34. In addition, system 130 may turn radiation source 14 off, or reduce power to radiation source 14 based on the monitored temperature of laser radiation source 14 (e.g., to prevent overheating). Radiation source control system 130 may utilize data or signals from any other control subsystems (e.g., user interface control system 134, temperature control system 136, and/or battery/charger control system 138) for controlling aspects of laser radiation source 14.

User interface control system 134 may include a user interface sensor control system 140 for monitoring and controlling displacement sensor 100, skin contact sensors 104, and/or eye safety sensor 114. For example, system 134 may receive signals detected by each sensor, and send control signals to each sensor. User interface control system 134 may include a user input/display/feedback control system 142 for monitoring and controlling user interfaces 28 and displays 32. For example, system 134 may receive user input data from various user interfaces 28, and control information communicated to the user via displays 32 (e.g., visually, audibly, and/or palpably). User interface control system 134 may communicate data or signals with, or otherwise cooperate with, other control subsystems, e.g., radiation source control system 130, temperature control system 136, and/or battery/charger control system 138.

Temperature control system 136 may be configured to monitor and control the temperature of one or more components of device 10, e.g., radiation source 14, battery 20, etc. Thus, temperature control system 136 may receive data from one or more temperature sensors 108, and control one or more fans 34 based on such data. In addition to controlling fan(s) 34, temperature control system 136 may generate control signals for controlling radiation source 14, motor 120, etc. based on temperature data. For example, temperature control system 136 may communicate signals to radiation source control system 130 to turn off or otherwise control radiation source 14 to avoid overheating (or in response to a detected overheating) of such component(s), to maintain such components within predefined performance parameters, or for any other purpose. Temperature control system 136 may communicate data or signals with, or otherwise cooperate with, radiation source control system 130, user interface control system 134, and/or battery/charger control system 138.

Battery/charger control system 138 may be configured to monitor and control the charging of battery 20. In some embodiments, multiple batteries 20 are included in device 10. In some embodiments, battery 20 may be removable from device 10, e.g., for replacement or as a consumable element (e.g., with optionally a unique hardware design or electronic encryption or other means to make proprietary). As shown in FIG. 3, device 10 may be configured for connection to a wall plug-in charger 170 and/or a charging stand 172 via control electronics 30, for charging battery 20. System 138 may monitor the current charge and/or temperature of battery 20, and regulate the charging of battery 20 accordingly. Battery/charger control system 138 may communicate data or signals with, or otherwise cooperate with, other control subsystems, e.g., user interface control system 134, temperature control system 136, and/or battery/charger control system 138. In other embodiments, e.g., where power supply comprises one or more cells (e.g., size A, AA, AAA, C, D, prismatic, or 9V cells), battery/charger control system 138, wall plug-in charger 170, and charging stand 172 may be omitted. Other embodiments may include a power cord connected to mains supply, an electronic power supply, or other sources of power. Such embodiments may still be substantially hand-held.

Device 10 may include a delivery end, referred to herein as application end 42, configured to be placed against the skin, in particular treatment area 40. Application end 42 may include or house various user interfaces, including the treatment delivery interface for delivering beams 60 to the user, as well as one or more sensors 26 for detecting various characteristics of the target surface and/or treatment delivered by device 10. For example, in the illustrated embodiment, application end 42 provides an interfaces for displacement sensor 100, skin contact sensors 104, and/or eye safety sensor 114, allowing these sensors to interface with the user's or patient's skin or tissue. In some embodiments, application end 42 provides a window 44 through which beams 60 are delivered.

Operation of Device 10

As discussed above, device 10 is configured to deliver one or more energy beams 60 to a treatment area 40 to provide a desired dermatological treatment. Device 10 may deliver beam(s) 60 to generate various treatment patterns in the treatment area 40. For example, various treatment patterns may be generated by any combination of the following: operating device 10 in a manual gliding mode, operating device 10 in a stamping mode, providing continuous wave (CW) radiation, providing pulsed radiation, providing direct exposure radiation, providing indirect exposure radiation, providing close proximity radiation, providing remote proximity radiation, any other modes, or any combination thereof.

Each energy beam 60 from device 10 may form an irradiated treatment spot ("treatment spot") 62 on the surface of the skin, and (in certain embodiments) a three-dimensional volume of thermally damaged skin extending below the surface of the skin, referred to herein as a micro thermal zone (MTZ) 64. Each MTZ may extend from the skin surface downward into the skin, or may begin at some depth below the skin surface and extend further downward into the skin, depending on the embodiment, device settings, or particular application. In embodiments or situations in which the irradiated area on the skin moves across the skin during delivery of the radiation, referred to as "blurring" or "smearing" of the irradiated area (e.g., as caused by movement of the device during a gliding mode operation of device 10, wherein the delivered beam 60 remains stationary with respect to the device housing 24), the treatment spot 62 is defined as the collective area swept by the moving irradiated area throughout a continuous (i.e., uninterrupted) period of radiation delivery to the skin at that location. Some embodiments may compensate for blur by tracking device motion across the skin and dynamically adjusting the location or direction of the delivered beam 60 with respect to the device housing 24, or by the configuration of light sources or scanning modes, or in other ways.

In some applications, such as hair removal treatment, beams 60 may generate treatment spots 62 to cause thermal injury of hair follicles. In other applications, such as fractional treatment for example, beams 60 (e.g., laser beams) may generate treatment spots 62 to cause thermal injury to the skin, e.g., ablative or non-ablative lesions.

In some embodiments, device 10 is configured to be used in a "gliding mode" in which the device is manually dragged or glided across the skin while delivering continuous wave (CW) radiation or pulsed radiation to the treatment area 40, e.g., to create continuous elongated treatment spots 62 in the direction of gliding, or alternatively to create rows or arrays of discrete treatment spots 62 (spaced apart, touching, or overlapping) in the direction of gliding.

In other embodiments, device 10 is configured to be used in a "stamping mode" in which device 10 is held relatively stationary at different locations on the skin. At each location on the skin, device 10 may deliver one or more beams 60 to generate one or more corresponding treatment spots 62 on the skin. Thus, device 10 may be positioned at a first location, one or more treatment spots 62 may then be delivered to the skin while device 10 is held relatively stationary, device 10 may then be moved—e.g., by lifting and repositioning device 10, or by gliding device 10 across the surface of the skin—to a new location on the skin, and one or more treatment spots 62 may then be generated at that location (e.g., by automated or manual pulsing of the radiation sources(s) 14), and so on, in order to cover a treatment area 40 as desired.

In some embodiments, device 10 may be configured to generate an array of MTZs 62 in the skin that are laterally spaced apart from each other by volumes of untreated (i.e., non-irradiated or less irradiated) skin, e.g., to provide a fractional treatment. For example, the application end 42 of device 10 may be manually moved across the surface of the skin during a treatment session. Energy beams 60 may be pulsed during the movement of device 10 across the skin (in a gliding mode operation), or between intermittent movements of device 10 across the skin (in a stamping mode operation). The skin's healing response, promoted by the areas of untreated skin between adjacent MTZs 64, may provide benefit in the treatment area (e.g., skin resurfacing or rejuvenation, wrinkle removal or reduction, etc.).

Direct Exposure and/or Close Proximity

As discussed above, some embodiments of device 10 are "direct exposure devices" that do not include any optics 16 downstream of radiation source(s) 14 for delivering or treating beam(s) 60. However, some direct exposure devices may include a planar or substantially planar window 44 (e.g., a thin sapphire or BK-7 like glass window or a thin film or equivalent) downstream of radiation source(s) 14, e.g., to protect the radiation source(s) and/or other internal components of the device.

In embodiments that use a relatively rapidly divergent beam source (e.g., edge emitting laser diodes, laser diode bars, and certain VCSELs), due to the rapid divergence of beam(s) 60 emitted from the radiation source(s) 14, the radiation source(s) 14 may be positioned very close to the application end 42 of the device that contacts the skin during treatment (and thus very close to the skin surface). For example, in some direct exposure devices, the radiation source(s) 14 may be positioned such that the emitting surface(s) of the radiation source(s) 14 are arranged at less than or equal to 10 mm of the skin during treatment, referred to herein as a close proximity configuration. In some embodiments, the emitting surface(s) of the radiation source(s) 14 are arranged at a distance of less than or equal to 5 mm, 2 mm, 1 mm, 500 µm, 200 µm, or even 100 µm from the surface of the skin when the application end 42 is placed in contact with the skin.

Some direct exposure embodiments of device 10 may be configured to provide CW radiation in a gliding mode. For example, as discussed below with respect to FIGS. 24A and 24B, direct exposure embodiments of device 10 including a high fill-factor laser diode bar 14C may be operated in a CW mode while the device is manually glided across the skin in a direction generally perpendicular to the elongated direction of the laser diode bar, to generate a continuous elongated treatment spot 62 in the manual glide direction, having a width generally corresponding to the width of the laser diode bar. The device may be glided multiple times across the skin at adjacent locations to cover a desired treatment area 40, e.g., to provide a hair removal treatment.

Other direct exposure embodiments of device 10 may be configured to provide pulsed radiation in a gliding mode, e.g., to provide a fractional treatment. For example, as discussed below, direct exposure embodiments of device 10 including one or more edge emitting laser diodes, laser diode bars, or VCSELs may be operated in a pulsed manner while the device is manually glided across the skin to generate a generally one-dimensional or two-dimensional array of treatment spots 62 for each glide of the device 10 across the skin. The device may be glided multiple times across the skin at adjacent locations and over the same area to cover a desired treatment area 40, e.g., to provide a fractional treatment.

Example Embodiment of Device 10

Figure 4:
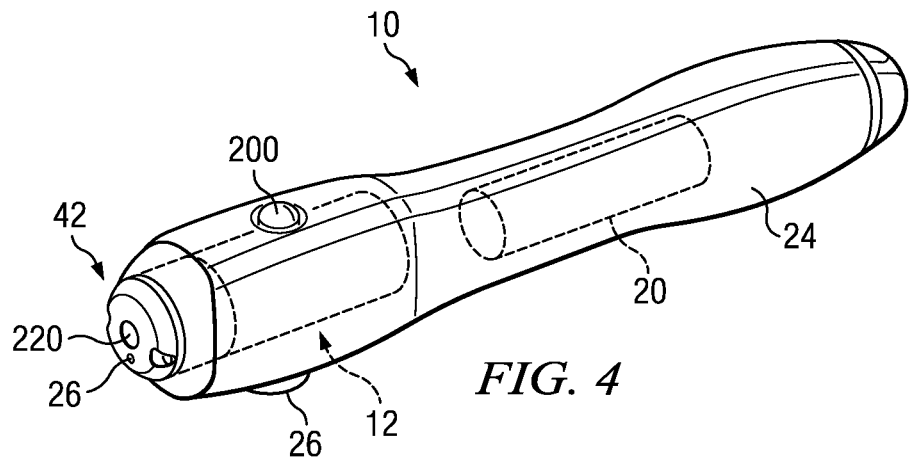
FIG. 4 illustrates an example radiation-based treatment device configured as a direct exposure device for providing fractional treatment, according to certain embodiments of the present disclosure.

FIGS. 4-7 illustrate an example embodiment of device 10 configured as a direct exposure device for providing fractional treatment. As shown in FIG. 4, the example device 10 may include a laser engine 12 including one or more lasers (e.g., one or more edge emitting laser diodes, laser diode bars, or VCSELs) configured to emit one or more pulsed laser beams 60, and one or more batteries 20, both housed in a device housing 24. In some embodiments, laser engine 12 includes a single beam source configured to emit a single pulsed beam 60, e.g., an edge emitting laser diode or a VCSEL configured to emit a single beam 60. In other embodiments, laser engine 12 includes multiple beam sources configured to emit multiple discrete pulsed beams 60, e.g., multiple edge emitting laser diodes, an laser diode bar, multiple laser diode bars, multiple VCSELs, or a VCSEL configured to emit multiple discrete beams 60 (e.g., as discussed below with reference to FIGS. 30-34), for example.

Battery or batteries 20 may include any number and type of batteries, e.g., A-sized or smaller batteries, or rechargeable or non-rechargeable cells (e.g., Li ion, lithium ferro phosphate, NiMH, NiCAD, or other cells), or any other type of battery.

Device 10 has an application end 42 configured to contact the user's skin as device 10 is moved across the skin during a treatment session. In this embodiment, application end 42 is defined by a leading end of laser engine 12, which projects from device housing 24. The application end 42 may include a laser treatment aperture 220 through which one or more laser beam(s) 60 generated by the laser engine 12 are delivered to the skin 40.

In addition, device 10 may include one or more sensors 26, e.g., any one or more of the various types of sensors 26 disclosed herein. For example, device 10 may include one or more skin contact sensors 104, a displacement sensor 100, a motion/speed sensor 102, a dwell sensor 116, and/or an eye safety sensor 114. The one or more sensors 26 may be located at any suitable location(s) on deice 10, e.g., at or near application end 42. In some embodiments, device 10 includes a skin contact sensor 104 and a displacement sensor 100 configured to avoid unintentional exposure and/or overexposure of the skin (e.g., by preventing stacking or overlapping of treatment spots 62). The skin contact sensor 104 and displacement sensor 100 may be provided by a single combined contact/displacement sensor, or may be provided as separate sensors. Such sensor(s) may be optical or capacitance-based or use any other suitable means. Contact with the skin may be detected by analyzing an amplitude of an optical reflectance or capacitance signal generated by the sensor. Further, dwelling of device 10 on the skin may be detected by analyzing signal in the optical reflectance or capacitance signal associated with application end 42 of device 10 moving across the skin or by other suitable means. Because skin surface is not perfectly smooth and the manual moving of a device cannot achieve perfect steady motion, stiction (static friction) between device 10 and skin and/or other physical principles result in micro-displacement (non-lateral) between the sensor and the skin surface. For example, a capacitive sensor's signal is inversely proportional to the relative distance between the sensor and the test surface. Any micro-displacement due to natural stick-and-slip movement across the skin will result in a translational signal on top of the nominal steady-state sensor signal. This signal may be analyzed to determine whether device 10 is moving across the skin, or dwelling at the same location. Such analysis may include any suitable algorithms, e.g., comparing the signal to one or more threshold values.

In the example shown in FIG. 4, device 10 includes a manual power button 200. Device 10 enables the delivery of beams to the skin in a pulsed manner while power button 200 remains depressed by the user, and the sensor(s) 26 detect that device 10 is in proper contact with the skin and has translated, is moving with a certain velocity range, and/or is not dwelling. In other embodiments, the power button may be a simple on/off switch and the light pulsing is controlled only, for example, by one or more sensors and not the manual power button.

The specific user interface scheme, and the shape and size of the device housing 24 may be configured as desired. In some embodiments, the shape and size of device housing 24 is easy to grip and includes a simple, conveniently located power button 200 and/or other user interfaces 28. In addition, the shape of device 10 may be ergonomic, and/or be configured to provide good visibility of the treatment area 40. Example shapes are pencil-like, pen-like, lipstick-like, organic shapes like pebbles, cigarette lighter-like, and numerous other shapes.

Figure 5A:
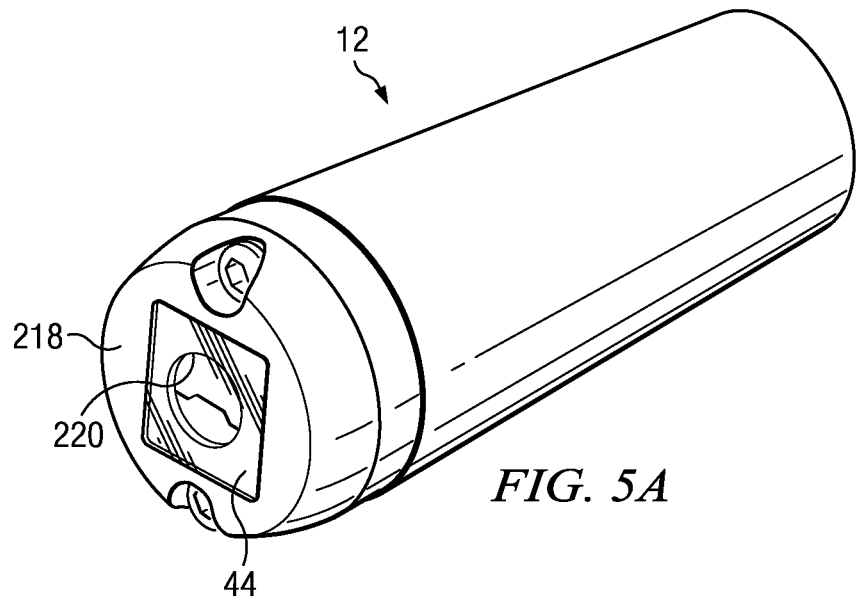
FIGS. 5A and 5B illustrate a 3-D side view and an end tip view, respectively, of an example radiation engine for use in the direct exposure laser treatment device shown in FIG. 4, according to an example embodiment.
Figure 5B:
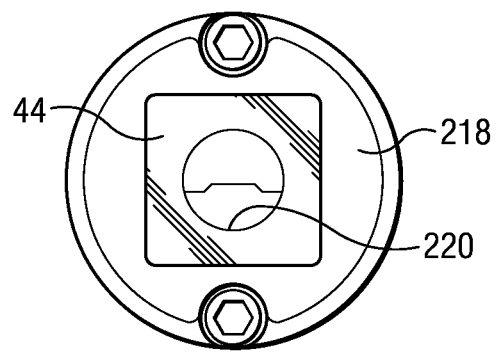
Figure 6:
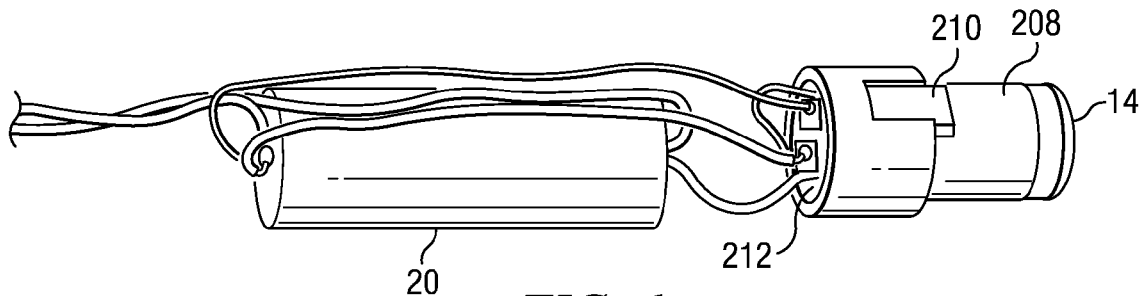
FIG. 6 illustrates an exploded view of the example laser treatment device shown in FIG. 5.

FIGS. 5A, 5B, and 6 illustrate details of an example laser engine assembly 12 for use in the example direct exposure fractional treatment device of FIG. 4, according to certain embodiments. In particular, FIGS. 5A and 5B illustrate an assembled view of the example laser engine 12, while FIG. 6 illustrates an exploded view of the various components of device 10.

In some embodiments, the laser engine 12 may include an edge emitting laser diode 14 directly mounted to a thermal reservoir heat sink 36 via any suitable manner (e.g., via soldering, clamping, or adhesive) or mounted to one or more subcarriers (e.g., a ceramic, plated ceramic, copper block, etc) to provide electrical isolation and/or thermal conduction, for example. Electrical connection to the edge emitting laser diode 14 may be made by wire bonding, soldering, clamping, or other suitable means between the edge emitting laser diode 14 and the subcarrier(s), to the heat sink 36, or to other electrical connection point(s) (e.g., a printed circuit board) in device 10. In some embodiments, the laser engine assembly 12 may include an edge emitting laser diode chip mounted on a heat spreader, which is in turn mounted to heat sink 36.

In some embodiments, the heat sink 36 may also be an internal chassis for supporting other components of laser engine 12. In some embodiments, the light output (power and wavelength) of the edge emitting laser diode 14 may be sensitive to temperature and should be held to a predetermined maximum temperature rise (e.g., about 25° C.). Thus, the heat sink 36 may include a temperature feedback system to automatically disable the laser if the maximum temperature is exceeded.

The edge emitting laser diode may be powered by one or more batteries 20, by way of a momentary switch 210 (activated by power button 200 shown in FIG. 4) and pulsing electronics 212, which control the pulsing of the edge emitting laser diode 14. The components shown in FIG. 6 may be contained in a laser engine housing 24, which may include housing sections held together by any suitable fasteners. As discussed above, other light sources, e.g., an laser diode bar or VCSEL (or multiple edge emitting laser diodes, laser diode bars or VCSELs), may be used instead of a single edge emitting laser diode. Furthermore, other power supply sources 20 may be used, such as a rechargeable battery (e.g., L-ion battery), mains electricity, or a super-capacitor, for example.

FIGS. 5A and 5B also show an example configuration of the application end 42 of the laser engine assembly 12, which may include a window 44 covering an aperture 220 through which the laser beam 60 is delivered from the edge emitting laser diode 14 to the skin. In this embodiment, window 44 comprises a transparent layer or pane (e.g., sapphire, glass, or plastic) positioned over aperture 220 to protect the internal components of laser engine 12. In other embodiments, aperture 220 may be open or laser engine 12 may be protected by a transparent (to edge emitting laser diode 14) encapsulant, such as suitable epoxy or spun-on-glass, rather than window 44. Aperture 220 may have any suitable size and shape. Laser engine assembly 12 may act as application end 42 of device 10, and thus contact the skin directly. Application end 42 may also form part of one or more of the sensors 26, such as providing a capacitive antenna for a skin contact sensor. Window 44 may project beyond an outer surface 218 of application end 42, may be arranged flush with outer surface 218 of application end 42, or may be recessed from outer surface 218 of application end 42.

In some embodiments, device 10 shown in FIGS. 4-7 is configured as a direct exposure, close proximity device, as such terms are defined herein. As discussed above, a non-optically-powered transparent layer or pane, or encapsulant, may be positioned between the edge emitting laser diode 14 and the target surface, or there may be nothing but an air gap between the edge emitting laser diode 14 and the target surface.

In some embodiments, the emitting surface of edge emitting laser diode 14 is configured to be located within 5 mm of the target skin surface. In certain embodiments, the emitting surface 82 of edge emitting laser diode 14 is configured to be located within 2 mm of the target skin surface, to provide a desired beam spot size and intensity at the target surface. In some embodiments, the emitting surface 82 of edge emitting laser diode 14 is configured to be located within 1 mm of the target skin surface, to provide a desired beam spot size and intensity at the target surface. In particular embodiments, the emitting surface 82 of edge emitting laser diode 14 is configured to be located within 500 µm, 200 µm, or even 100 µm of the target skin surface during use. Due to the very small distance between the edge emitting laser diode 14 and the target skin surface, as well as lack of optics, the edge emitting laser diode 14 need not be aligned with high precision.

In some embodiments, various aspects of device 10 (e.g., the type of edge emitting laser diode 14, the distance between edge emitting laser diode 14 and the skin surface, etc.) are configured to produce treatment spots 62 on the skin having a diameter of less than 2,000 µm in the largest dimension. In particular embodiments, the beam spot size on the target surface has a diameter of less than 700 µm in the largest dimension, which may be suitable for certain treatments, e.g., treatment of solar lentigo (age spots), wrinkles, and/or fine lines. In specific embodiments, the beam spot size on the target surface has a diameter of between about 75 µm and about 350 µm in the largest dimension, which may be suitable for certain treatments, e.g., treatment of wrinkle and/or fine lines. The diameters listed above do not account for any "blurring" or "smearing" of the treatment spots 62 caused by movement of device 10 across the skin during the particular beam pulse. The actual diameter of particular treatment spots 62 (in the direction of device 10 movement across the skin) may thus be larger than the nominal diameters listed herein, due to such blurring or smearing of spots 62.

In some embodiments, device 10 is configured to produce treatment spots 62 having an area of less than 1.0 mm². In particular embodiments, device 10 is configured to produce treatment spots 62 having an area of less than 0.4 mm$^2$, which may be suitable for certain treatments, e.g., treatment of solar lentigo (age spots), wrinkles, and/or fine lines. In specific embodiments, device 10 is configured to produce treatment spots 62 having an area of less than 0.1 mm$^2$, which may be suitable for certain treatments, e.g., treatment of wrinkle and/or fine lines or pigmentation. Finally, in some embodiments, device 10 is configured to produce treatment spots 62 having an area of less than 0.05 mm$^2$, which may also be suitable for certain fractional treatments. The treatment size areas listed above do not account for any "blurring" or "smearing" of the treatment spots 62 caused by movement of device 10 across the skin during the particular beam pulse. Thus, the actual area of individual treatment spots 62 may be larger than the areas listed above, due to such blurring or smearing of spots 62.

In one example embodiment, device 10 is configured such that the emitting surface of edge emitting laser diode 14 is less than 1 mm from the target skin surface, and edge emitting laser diode 14 has a nominal laser emitter area of about 100 μm (in the slow axis direction) by 5 μm (in the fast axis direction). This configuration may yield treatment spots 62 having an equivalent nominal diameter of between about 150 μm and about 350 μm.

Figure 7:
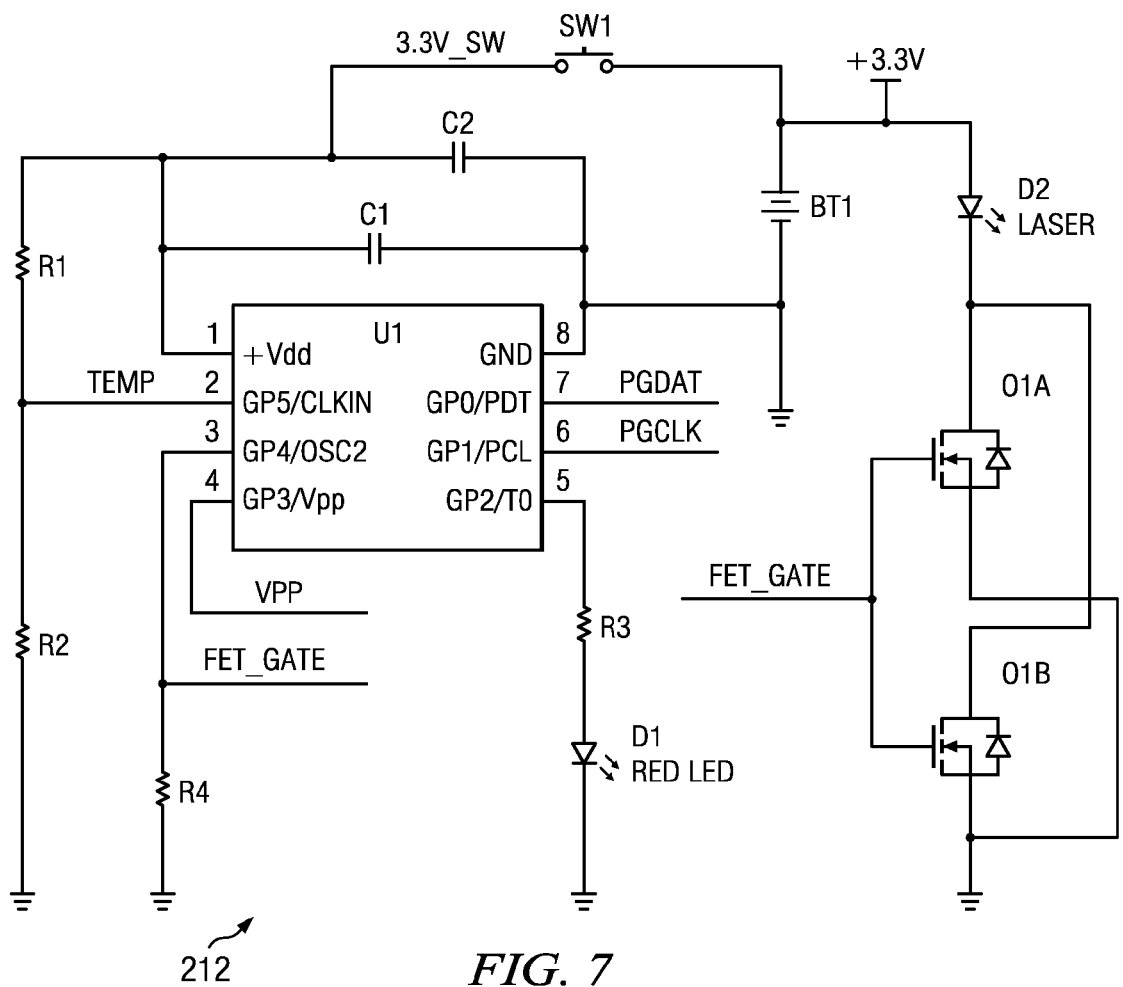
FIG. 7 illustrates an example electrical schematic of laser pulsing electronics for controlling the pulsing of the edge emitting laser diode of the example direct exposure laser treatment device shown in FIGS. 5-7.

FIG. 7 illustrates portions of an example electrical schematic of the laser pulsing electronics 212 for controlling the pulsing the edge emitting laser diode 14 of the example embodiment shown in FIGS. 4-6, according to one embodiment. In this embodiment, the laser pulsing electronics 212 generate current pulses through the edge emitting laser diode 14 at a fixed rate as long as the signals from the appropriate sensor(s) 26 are valid and the manual power button 200 is activated. The pulse energy may be controlled via the pulse duration. A single-cell AA-sized Li battery may be used to provide a drive current of about 7 Amps through the edge emitting laser diode, to provide a laser output power of about 3 Watts, sufficient to produce a desired tissue response for particular applications or treatments, e.g., certain fractional treatments.

As discussed above, the pulse rate may be set or selected based on a typical or expected manual glide speed of device 10 is across the skin. In particular, the pulse rate may be set or selected such that for a range of typical or expected manual glide speeds (e.g., between 2 cm/s and 6 cm/s), adjacent treatment spots 62 are physically separated from each other by areas of non-treated skin, i.e., fractional treatment is provided. In some embodiments, the pulse rate may be set or selected such that for a range of typical or expected manual glide speeds (e.g., between 2 cm/s and 6 cm/s), adjacent treatment spots 62 are physically separated from each other from a predetermined minimum non-zero distance, e.g., 500 μm.

In some embodiments, device 10 may provide a pulse repetition frequency ("PRF") between 1 and 50 Hz. For example, device 10 may provide a PRF of between 5 and 25 Hz. In particular embodiments, device 10 may provide a PRF of about 15 Hz.

In some embodiments, device 10 may be controlled to prevent, limit, or reduce the incidence or likelihood of treatment spot overlap, e.g., based on feedback from one or more sensors 26 (e.g., a displacement sensor 100, speed/motion sensor 102, and/or a dwell sensor 116). In some embodiments, the pulse rate may be automatically adjustable by device 10 and/or manually adjustable by the user, e.g., to accommodate different manual movement speeds and/or different comfort levels or pain tolerance levels of the user.

Figure 8A:
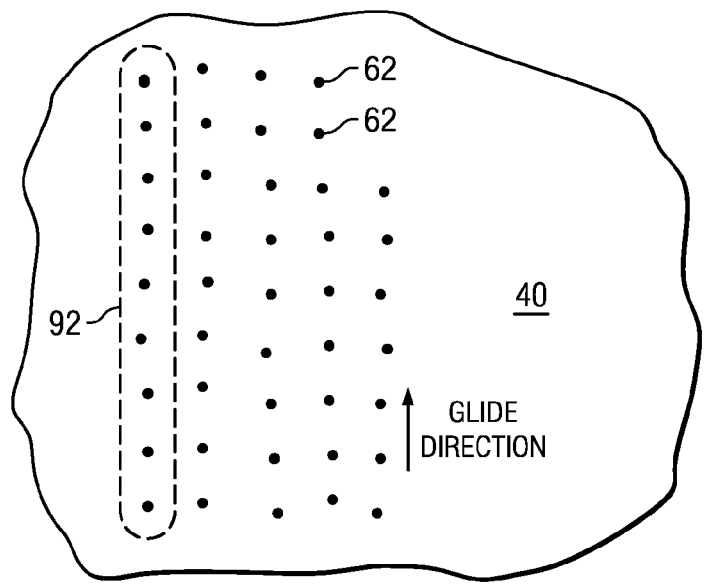
FIGS. 8A-8J illustrates example patterns of treatment spots and example glide directions and patterns for use with the device of the present disclosure, according to certain embodiments.

FIG. 8A illustrates an example of a manually scanned pattern of treatment spots 62 generated in a treatment area of skin 40 by an embodiment of device 10 including a single beam source configured to emit a single pulsed beam 60, e.g., a single edge emitting laser diode or a single VCSEL configured to emit a single beam 60. Device 10 is glided across the skin while the single beam source is pulsed to create a pattern of spaced-apart treatment spots 62. Each glide of the device in a particular direction creates a generally linear array of treatment spots 62. A first array produced by a first glide, or "manual scan," of device 10 across the skin is indicated at 92. five linear arrays of spots 62 corresponding to five manual scans 92 of device 10 are shown in FIG. 8A. Device 10 may be manually scanned across the skin any number of times and in any direction or directions to effectively cover a particular treatment area 40. The treatment spot pattern may therefore be random or quasi-random, unlike certain mechanically scanned systems, which may have benefit, such as to be less cosmetically detectable to the eye than a more regular grid.

Figure 8B:
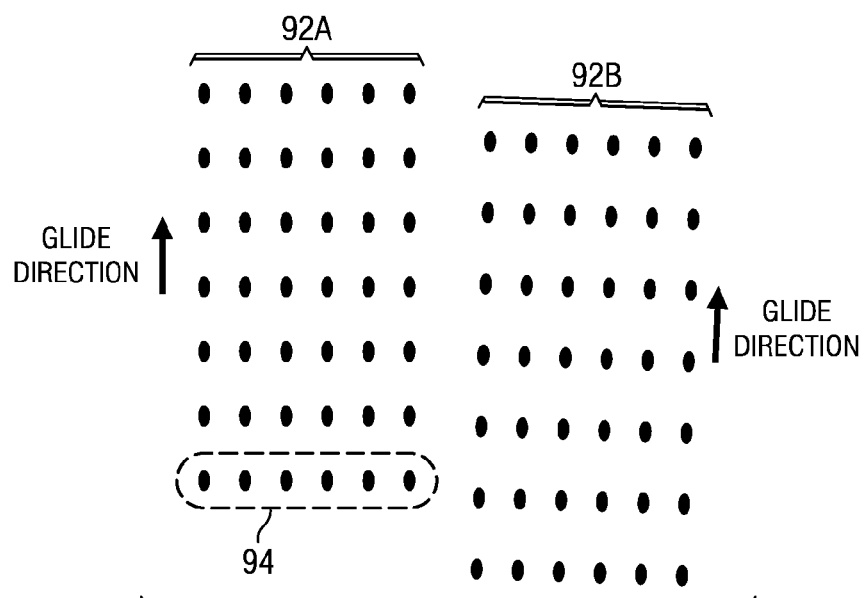
Figure 8C:
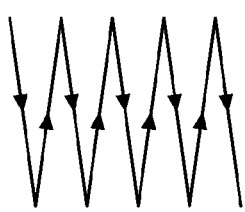
Figure 8D:
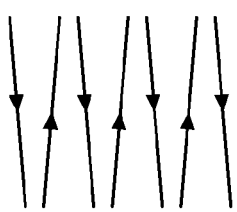
Figure 8E:
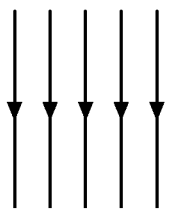
Figure 8F:
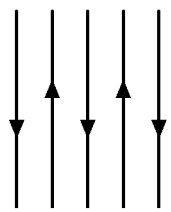
Figure 8G:
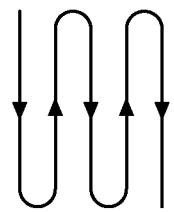

FIG. 8B illustrates an example of a manually scanned pattern of treatment spots 62 generated in a treatment area of skin 40 by an embodiment of device 10 including multiple beam sources configured to emit multiple discrete pulsed beams 60, e.g., multiple edge emitting laser diodes, an laser diode bar, multiple laser diode bars, multiple VCSELs, or a VCSEL configured to emit multiple discrete beams 60 (e.g., as discussed below with reference to FIGS. 30-34), for example. Device 10 is glided across the skin while the multiple beam sources of device 10 are pulsed (simultaneously, sequentially among the individual beam sources, randomly, or otherwise, depending on the particular type of beam sources and configuration of device 10) to create a pattern of spaced-apart treatment spots 62. Each pulse of the multiple beam sources generates a corresponding array of multiple treatment spots 62, indicated at 94 in FIG. 8B (in this example, 6 spots, such as might be generated by a laser diode bar with 6 spaced emitters). Thus, each manual glide of the device in a particular direction creates a generally two-dimensional array of treatment spots 62. Two manual glides, or "manual scans," of device 10 across the skin are indicated at 92A and 92B. Device 10 may be manually scanned across the skin any number of times and in any direction or directions to effectively cover a particular treatment area 40. In this example, treatment spots are elongated in the glide direction, which could occur from "smearing" if compensation is not included, or from the beam properties itself having a non-symmetric energy profile.

Figure 8H:
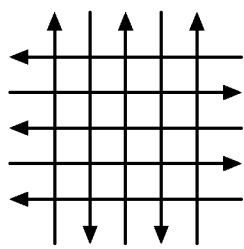
Figure 8I:
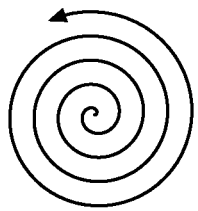
Figure 8J:
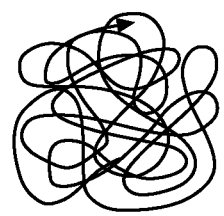

FIGS. 8C-8J illustrate example manual glide, or "manual scan," patterns for covering a particular treatment area 40 using device 10. FIGS. 8C-8G illustrate example patterns in which device 10 is manually scanned in the same general direction (e.g., back and forth along parallel or near-parallel directions). In some treatments or applications, device 10 may be scanned in two or more different directions, e.g., to form a criss-cross pattern, such as shown in FIG. 8H, for example. This may yield a more uniform coverage pattern. Other example manual scan patterns include a generally spiral pattern, as shown in FIG. 8I, or a random pattern, as shown in FIG. 8J. Certain treatment patterns may be preferred or specified or configured, such as a series of one-dimensional treatment lines that radiate outward from the eyebrow to achieve a skin tightening effect analogous to a surgical eyebrow lift), for any suitable benefit. Areas may also be treated in multiple passes, e.g., to increase treatment spot density, increase randomness, or other reason. Any other suitable manual scan patterns may be used as appropriate.

Figure 9:
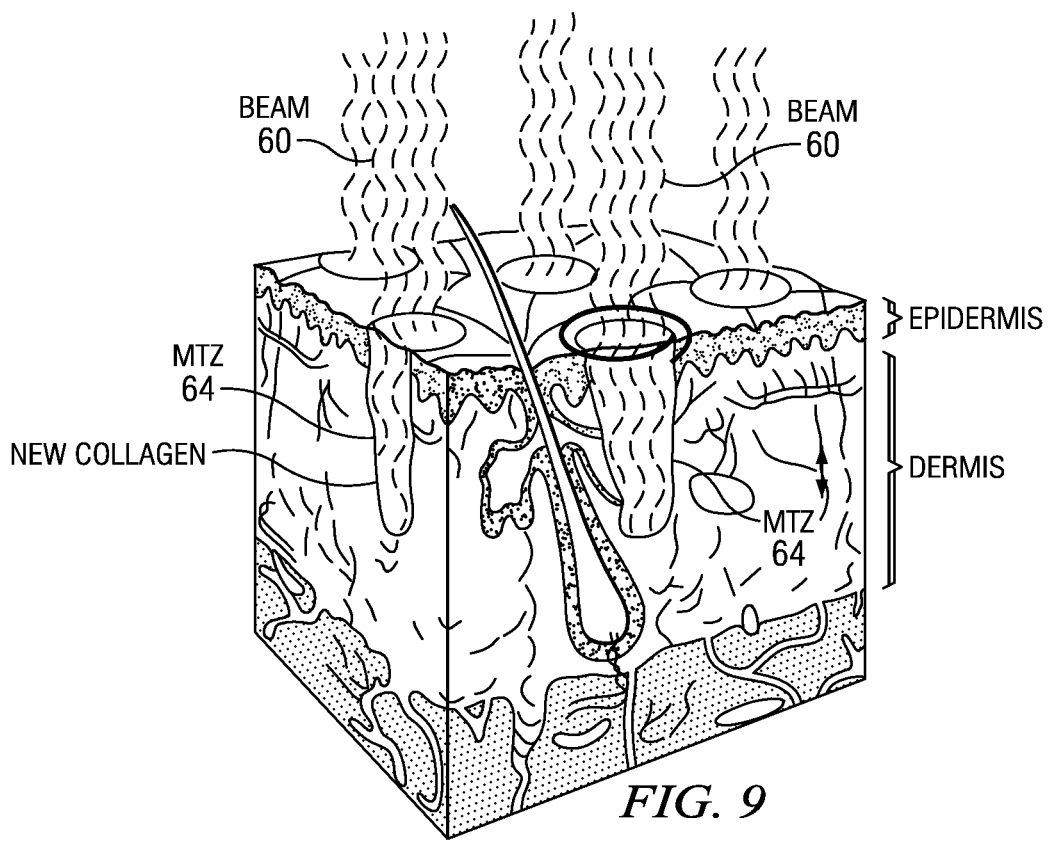
FIG. 9 shows a three-dimensional cross-section of a volume of skin for illustrating the process of a non-ablative fractional treatment.

FIG. 9 shows a three-dimensional cross-section of a volume of skin for illustrating the process of a non-ablative fractional treatment consisting of an array of MTZs in the skin 64. Each MTZ 64 is a small volume of denatured (or otherwise influenced, such as photochemical or photobiological) epidermis and dermis generally shaped as a column or elongated bowl and extending downward from the skin surface or subsurface in a direction substantially orthogonal to the skin surface. The damaged skin of the MTZ 64 is surrounded by untreated (and thus not denatured, in this example) skin. Because of the proximity of healthy skin cells, the damaged skin of the MTZ 64 heals relatively quickly (as compared to traditional non-fractional treatments, such as CO2 laser resurfacing) and reduces wrinkles, scarring, and/or uneven pigmentation as part of the healing process. During the healing process, MENDS (microscopic epidermal necrotic debris) may be formed. Since the MTZs typically cover only a fraction (e.g., less than 1% to about 70% of the skin surface, side effects may be substantially reduced as compared to traditional non-fractional treatments, such as CO2 laser resurfacing. In some home-use embodiments of this disclosure, coverage fraction may be between 0.25% and 5% of the skin per treatment. In some embodiments, device 10 is configured such that the size and shape (e.g., height and width and depth) of the MTZs 64 spare many of the stem cells and melanocytes in the papillary dermis.

Prevention of Treatment Spot Overlap

As discussed above, in some embodiments, device 10 may be configured to prevent, limit, or reduce the incidence or likelihood of treatment spot overlap, e.g., based on feedback from one or more sensors 26 (e.g., a displacement sensor 100, speed/motion sensor 102, and/or a dwell sensor 116). For example, in some embodiments, the pulse rate may be automatically adjustable by device 10 and/or manually adjustable by the user, e.g., to accommodate different manual movement speeds and/or different comfort levels or pain tolerance levels of the user.

Some embodiments include other devices or techniques that individually or in combination provide over-treatment protection, e.g., to prevent pulse stacking, firing on the same area, an excessive treatment spot 62 density, or other non-desirable treatment conditions. For example, in some embodiments, device 10 ceases to operate (e.g., generate or deliver beams) when stationary condition of device 10 is detected. A stationary condition may be determined using one or more sensors, e.g., any one or more motion sensors, speed sensors, dwell sensors, vibration and tilt sensors, accelerometers, and/or displacement sensors. Such sensors may generate signals based on capacitance, optical reflection, remittance, scattering variation, acoustical reflection variation, acoustical impedance, galvanic potential, potential difference, dielectric constant variation, or any other parameter.

In some embodiments, device 10 uses local pyrometry (alone or in combination with other techniques mentioned above) to detect a stationary condition. The treatment beam area may be optically measured by local thermal imaging of the skin, and a stationary condition may be detected where local heating of the skin exceeds a threshold temperature or other parameter value.

In some embodiments, device 10 fires an "encouragement pulse" when a stationary condition is detected. For example, a single non-damaging but higher than normal energy pulse (causing discomfort but not damage) or a brief pulse train may be emitted if a stationary condition is detected, to encourage the user to move device 10.

A stationary condition may further be measured by bulk heating measurement, for example. If the tip of the treatment delivery device or the sensed skin temperature or region of skin temperature begins to heat above a threshold, loss of motion is detected, or excessive treatment in the area is detected.

As another example, device 10 may deliver heat or cold to the skin to encourage motion, as dwelling in one location may become uncomfortable. As another example, mechanical rollers may be used to detect a non-motion condition. Alternatively, motorized rollers may drive motion of device 10 across the skin, thus physically avoiding a non-motion condition.

In some embodiments, physiological feedback based on beam characteristics may be exploited, e.g., by designing the output for treatment efficacy as well as perception of the presence of treatment. For example, discomfort may be exploited such that overtreatment is discouraged by pain feedback that increases with excessive treatment.

In some embodiments, photobleaching may be used with indigenous or exogenous substances. For example, the skin may be treated with a dye that is photobleached by the treatment beam or by a separate bleaching beam used to bleach the treated area and potentially its surrounding areas. In this example, device 10 may be configured to detect the presence of the unbleached dye and would allow treatment only on areas with unbleached dye, thus preventing repetitive treatment on the same area (since that would be photobleached).

Any of the over-treatment protection systems or techniques described above (expect those directly concerned with pulse parameters) may be similarly incorporated in any CW radiation embodiment, e.g., for a hair removal device.

Pulse Rate Frequency (PRF)

In embodiments that include a pulsed radiation source 14 (e.g., with one or more pulsed beam sources), the pulse rate frequency (PRF) may be functionally interrelated with one or more other configurational or operational parameters of device 10, including (a) the manual glide speed, (b) spacing between treatment spots generated by consecutive pulses, referred to herein as "consecutive spot spacing," and (c) the amount of "smearing" or "blurring" of individual treatment spots. The amount of "smearing" or "blurring" of a treatment spot may be quantified by a "blur factor," defined as the ratio of the area of the blurred treatment spot 62 (with blurring caused by movement of device 10) to the area of the instantaneous treatment spot size. Thus, to illustrate, a blur factor of 1.0 indicates no blurring, a blur factor of 2.0 indicates a doubling of the treatment spot size area, and a blur factor of 3.0 indicates a tripling of the treatment spot size area.

Further, in at least some embodiments, the consecutive spot spacing and the blur factor for any particular operation of device 10 are defined as a function of (a) the manual glide speed, (b) the instantaneous spot size (i.e., the spot size at any particular instant, thus ignoring any burring affects), and (c) any set of parameters that defines the timing of a pulse sequence (referred to herein as "pulse timing parameters," e.g., selected from pulse duration (i.e., pulse on-time), delay between pulses (i.e., pulse off-time), pulse rate frequency (PRF), duty cycle, etc.

In some embodiments, the pulse rate frequency (PRF) and/or one or more other pulse timing parameters are controlled to provide (a) a predefined or selected minimum consecutive spot spacing, and/or (b) a predefined or selected maximum amount of spot blurring (e.g., a predefined or selected maximum blur factor), and/or (c) any other target parameter(s). "Controlling" the PRF and/or pulse timing parameter(s) may include:

(a) device 10 selecting or setting the PRF and/or at least one other pulse timing parameter, e.g.:

(i) automatically selecting a PRF and/or at least one other pulse timing parameter based on a user-selected operational mode, treatment level, or other user input, or (ii) automatically selecting a PRF and/or at least one other pulse timing parameter independent of user input (e.g., based on a device-selected operational mode, treatment level, or other level, or based on a detected glide speed during a portion of a treatment or a pre-treatment period of operation (e.g., using a motion/speed sensor 102), based on a glide speed detected and stored from a previously performed treatment (e.g., using a motion/speed sensor 102), based on one or more parameters detected by sensor(s) 26 in real time or otherwise (e.g., as skin temperature detected by temperature sensor(s) 106, or skin color detected by pigment sensor(s) 110, for example), or based on any other any other data or signals collected in real time or otherwise; and/or (b) device 10 dynamically adjusting the PRF and/or at least one other pulse timing parameter during a treatment session (e.g., in real time or substantially in real time), e.g., (i) based on feedback from one or more sensors 26, e.g., device displacement detected by displacement sensor(s) 100, glide speed detected by motion/speed sensor(s) 102, skin contact sensor(s) 104, skin temperature detected by temperature sensor(s) 106, delivered radiation detected by radiation sensor(s) 108, skin color detected by pigment sensor(s) 110, signals from eye safety sensor(s) 114, dwell status detected by dwell sensor(s) 116, and/or device displacement and/or glide speed detected by roller-based sensor(s) 118, and/or (ii) based on based on any other any other data or signals collected in real time or otherwise.

As discussed above, in some embodiments, the PRF and/or at least one other pulse timing parameter are controlled to provide (a) a predefined or selected minimum consecutive spot spacing and/or (b) a predefined or selected maximum amount of spot blurring (e.g., a predefined or selected maximum blur factor).

For example, in some embodiments, the PRF and/or at least one other pulse timing parameter are controlled to provide a minimum consecutive spot spacing of 1 mm. Assuming a glide speed of between 2 cm/s and 6 cm/s, and a spot size of between 200 μm and 600 μm, a PRF of 15 Hz, pulse duration of 3 ms, and duty cycle of 4.5% may be selected to provide such spot spacing. At these operational parameters, the resulting blur factor is about 130 to 190% Dora spot size of 200 μm, and about 110 to 130% for a spot size of 600 μm.

As another example, in some embodiments, the PRF and/or at least one other pulse timing parameter are controlled to provide a minimum consecutive spot spacing of 0.5 mm. Assuming a glide speed of between 2 cm/s and 6 cm/s, and a spot size of between 300 μm and 600 μm, a PRF of 30 Hz, pulse duration of 5 ms, and duty cycle of 15% may be selected to provide such spot spacing. At these operational parameters, the resulting blur factor is about 133 to 200% for a spot size of 300 μm, and about 117 to 150% for a spot size of 600 μm.

In some embodiments, a PRF of between 1 and 50 Hz is selected. For example, device 10 may provide a PRF of between 5 and 25 Hz. In particular embodiments, device 10 may provide a PRF of about 15 Hz.

In some embodiments, the device 10 is controlled to provide a minimum consecutive spot spacing of 1 mm. For example, the device 10 may controlled to provide a minimum consecutive spot spacing of 0.5 mm. In particular embodiments, the device 10 may controlled to provide a minimum consecutive spot spacing of 0.25

In some embodiments, a pulse duration of between 1 ms and 10 ms may be selected. In certain embodiments, a pulse duration of between 2 ms and 8 ms [smaller range] may be selected. In particular embodiments, a pulse duration of between 3 ms and 6 ms may be selected.

Some Example Embodiments and Example Operation Parameters

Any of the various features and configurations discussed herein may be combined in any suitable manner, for providing a variety of different treatments. Some example configurations with example parameter values are provided below. It should be understood that these are examples only.

Table 1 below shows example values and parameters for one example embodiment of device 10 similar to the device shown in FIGS. 4-7. In this example, to achieve 250 treatment spots/cm$^2$ and a fractional coverage ratio of 2.5% with 8 mJ/treatment spot, and the stated minimum coverage rate and duty factor, a 1.73 W light source is pulsed at 30 Hz and the application end or "tip" moved with a speed of 3.43 cm/s. The calculated blur factor caused by the movement of the treatment tip 42 across the skin and other parameters are also indicated.

TABLE 1

| Pameter | Example Target Value |
| --- | --- |
| MTZ per cm2 | 250 |
| treated skin (%) | 2.5 |
| area treated per MTZ (sq microns) | 10000 |
| spot dia, no motion (microns) | 113 |
| energy per mtz (mJ) | 8 |
| fluence, no motion (J/cm2) | 80 |
| min cov rate (cm2/min) | 13 |
| min cov rate (cm2/s) | 0.22 |
| min prf (hz) | 30 |
| max period (s) | 0.0185 |
| duty factor (%) | 25 |
| on time (s) | 0.0046 |
| tip speed (cm/s) | 3.43 |
| actual area treated (microns) | 27841 |
| blur factor | 2.8 |
| actual fluence (J/cm2) | 29 |
| power (w) | 1.73 |

Table 2 below shows example parameters and values for another example embodiment of device 10 similar to the device shown in FIGS. 4-7. A device with substantially these parameters has been clinically tested on human subjects and animal models and shown to produce desirable tissue response and clinical benefit, such as texture improvement and reduction in pigmented lesions.

TABLE 2

| Parameter | Example Value |
| --- | --- |
| Mechanical | |
| Size (Length × Diameter) | about 12 cm × about 1.7 cm (4.7 in. × 0.7 in.) |
| Weight | 46 gr. |
| Electrical: | |
| Battery (AA) | LiFePO4 |
| Batterty Life between recharges | about 2 hrs |
| Drive Current | 7.6 A |
| Laser Diode Voltage | 2.1 V |
| Optical: | |
| Pulse Energy | 14 mJ |
| Pulse Repetition Rate | 10 Hz |
| Pulse Width | 3.3 ms |

TABLE 2-continued

| Parameter | Example Value |
|---|---|
| Peak Power | 4.24 W |
| Average Power | 0.14 W |
| Wavelength | 1450 nm |
| E/O efficiency | 26.6% |

Table 3 below shows example values and parameters for three example configurations of an example device 10 similar to the device shown in FIGS. 4-7. The table shows, for each of the three example configurations, different optical power, pulse-on and pulse-off times, treatment spot diameters, treatment tip dimensions, and scan speeds. Resulting pulse rates, energy per pulse, minimum scan speed for full coverage, illuminated area, blur effect, fluency, and other parameters are also shown. Also shown are calculations related to overtreatment protection where, in this particular example, photobleaching is used to differentiate treated and untreated areas. The treatment spot sizes and energies can be obtained by direct-coupled edge emitting laser diode emission (e.g., from one or more single-beam edge emitting laser diode in close proximity to the skin with no intervening optics 16 (although a protective window may be provided) or by a fiber delivered beam or by other suitable optical means. For example, an edge emitting laser diode beam source of 500 micron chip size and 100 micron beam source size may be used to obtain the parameters shown if placed in very close proximity to the skin.

TABLE 3

| Parameter | Example Config. 1 | Example Config. 2 | Example Config. 3 |
|---|---|---|---|
| optical power (W) | 4 | 7 | 7 |
| on time of pulse (ms) | 10 | 10 | 8 |
| off-time of pulse (ms) | 30 | 30 | 8 |
| PRF (hz) | 25 | 25 | 63 |
| energy per pulse (mJ) | 40 | 70 | 56 |
| spot diameter (microns) | 150 | 220 | 150 |
| square tip dimension (microns) | 625 | 625 | 625 |
| min scan speed for full coverage (cm/s) | 1.56 | 1.56 | 3.91 |
| scan speed (cm/s) | 0.50 | 2.00 | 3.91 |
| illuminated area per MTZ (mm2) | 0.0252 | 0.0820 | 0.0646 |
| blur (illum area/spot size) | 1.4 | 2.2 | 3.7 |
| Fluence per MTZ (J/cm2) | 159 | 85 | 87 |
| area treated per second (mmw2) | 0.63 | 2.05 | 4.04 |
| area bleached per pulse (sq mm) | 0.39 | 0.39 | 0.39 |
| area bleached per second (mm2) | 9.77 | 9.77 | 24.41 |
| (area treated)/(area bleached) | 6% | 21% | 17% |
| area bleached per minute (cm2) | 5.86 | 5.86 | 14.65 |
| area bleached per minute (in2) | 0.91 | 0.91 | 2.27 |

Table 4 below shows example parameter values for a direct exposure embodiment using a low fill-factor laser diode bar as the radiation source 14B, operating in a gliding mode in which the device is glided perpendicular to the elongated direction of the laser diode bar 14B, with pulsed radiation for fractional treatment. Each pulse of the laser diode bar 14B generates a linear array of discrete, spaced-apart treatment spots 62, each corresponding to one emitter 80 of the laser diode bar 14B, e.g., as discussed with respect to FIGS. 22A and 22B.

TABLE 4

| Parameter | Example value | Specific example |
|---|---|---|
| Radiation source = laser diode bar | | |
| Total optical efficiency (laser diode bar to target) | 70%-90% | about 80% |
| Proximity gap spacing | 1 mm-10 mm | about 1.5-2.5 mm |
| Power emitted | | |
| per emitter | 1.3-9 W | 2.4 W |
| total emitted by diode bar | 50-80 W | 70 W |
| Pulse characteristics | | |
| pulse on-time | 2-20 ms | 6 ms |
| duty cycle | 10-60% | 50% |
| Length of instantaneous irradiated area on target from single beam source (perpendicular to elongated direction of diode bar) | 0.1-0.6 mm | 0.2 mm |
| Width of instantaneous irradiated area on target from single beam source (parallel to elongated direction of diode bar) | 0.1-0.6 mm | 0.3 mm |
| Manual glide speed | 2-6 cm/s | 4 cm/s |
| Total width of treatment spot 62 pattern (parallel to elongated direction of diode bar) | 0.5-2 cm | 1 cm |
| Length of individual treatment spot 62 (perpendicular to elongated direction of diode bar) | 0.1-1 mm | 0.3 mm |
| Area of individual treatment spot | 0.04-0.6 mm$^2$ | 0.09 mm$^2$ |
| Width of non-irradiated areas between individual treatment spots 62 (parallel to elongated direction of diode bar) | 150-800 µm | 300 µm |
| Energy delivered per individual treatment spot | 2-100 mJ | 12 mJ |
| Length of non-irradiated areas between successive treatment spot 62 patterns (perpendicular to elongated direction of diode bar) | 0.1-1.2 mm | 0.25 mm |

Single-Beam Edge Emitting Laser Diodes

As discussed above, in some embodiments, radiation source 14 is an edge emitting laser diode (or multiple edge emitting laser diodes) including a single emitter (i.e., a single beam source) that generates a single laser beam. In a typical edge emitting laser diode, the emitted beam has a beam divergence of nearly 45° in the fast axis direction and about 10° in the slow axis.

Due to the rapid divergence in the fast axis direction, the laser diode bar provides a significant beam spread in this fast axis direction, in the absence of optical elements provided downstream of the laser diode bar. Therefore, in order to capture a desired portion of the beam energy (and/or maintain a desired beam intensity), certain embodiments are configured as "close proximity" devices in which the "proximity gap spacing" is less than or equal to 10 mm. As used herein, the "proximity gap spacing" or "PGS" is defined as the distance between the emitting surface of the radiation source (in this case, the edge emitting laser diode) and the skin-contacting surface of device 10, i.e., the distance between the emitting surface of the radiation source and the skin during a treatment position of device 10 on the skin.

In some embodiments, the proximity gap spacing is less than or equal to 5 mm, 2 mm, or even 1 mm. In particular embodiments, the proximity gap spacing is less than 500 µm, less than 200 µm, or even less than 100 µm. The proximity gap spacing may be selected based on one or more parameters, e.g., the desired size and/or intensity of treatment spots 62 delivered to the skin, and/or manufacturing constraints or costs.

FIGS. 10-14 illustrate example direct exposure configurations, which may further be configured for "close proximity" radiation, depending on the proximity gap spacing or "PGS" of the particular embodiment. Thus, in certain embodiments, device 10 configured as shown in any of FIGS. 10-14 may have a proximity gap spacing of less than or equal to 10 mm, 5 mm, 2 mm, 1 mm, 500 µm, 200 µm, or even 100 µm in particular configurations.

Figure 10:
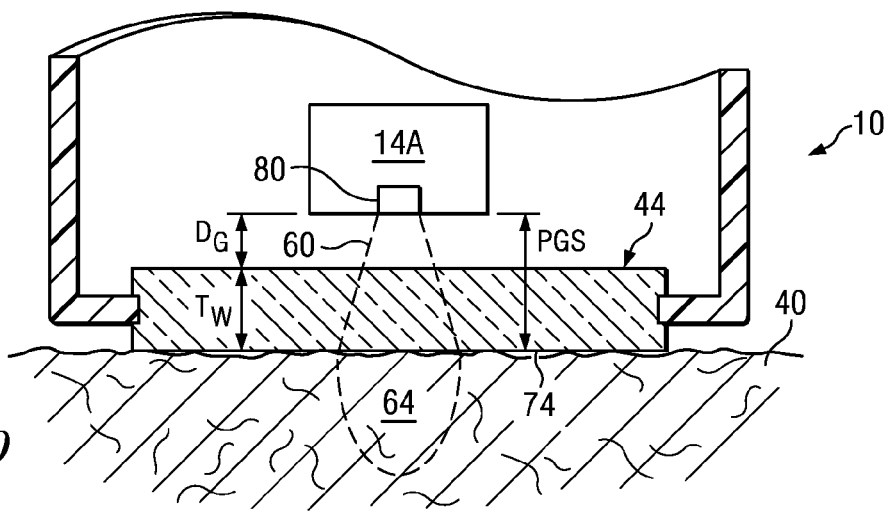
FIG. 10 illustrates a simplified cross-sectional side view of an example direct exposure embodiment that includes an edge emitting laser diode and a window in contact with the skin.

FIG. 10 illustrates a simplified cross-sectional side view of an example embodiment of device 10 that includes an edge emitting laser diode 14A including an emitter 80 having an emitting surface 82. A transmissive window 44 (e.g., a sapphire or other transmissive window, or a thin transmissive film) is located at the application end 42 of device 10, and forms a skin-contacting surface 74 with the skin 40. In some embodiments, manufacturing or other limits may prevent the emitter 80 from being placed directly onto the window 44, thus forming a gap between emitter 80 and window 44. Thus, the proximity gap spacing (PGS) between the emitting surface 82 of edge emitting laser diode 14A includes the thickness of the window 44 ($T_W$) plus the gap distance ($D_G$) between the emitting surface 82 and the window 44. In other embodiments, emitter 80 or emitting surface 82 may be placed directly onto the window 44, such that the gap distance ($D_G$) is effectively zero.

In some embodiments, window 44 has a thickness ($T_W$) of between about 100 µm and about 200 µm, with a gap distance ($D_G$) of about 50-150 µm, providing in a proximity gap spacing (PGS) of between about 150 µm and about 350 µm. In other embodiments, window 44 is a thin film having a thickness of less than 150 µm, e.g., about 75 µm, such that the proximity gap spacing (PGS) may be about 125-225 µm, depending on the gap distance ($D_G$).

In one example embodiment, window 44 is a sapphire window with a thickness of about 140 µm, with a gap distance of about 100 µm, providing a proximity gap spacing (PGS) of about 240 µm. At a proximity gap spacing of 240 µm, an edge emitting laser diode that emits a 1-micron by 95-micron beam with divergence of 28 deg FWHM (fast axis) by 6 deg FWHM (slow axis), respectively, will form an approximately circular treatment spot on the skin having a diameter of about 120 µm. With a device glide speed of about 2 cm/s and a 5 ms pulse duration, the treatment spot becomes an oval of about 120 µm by 220 µm in respective diameters. In another example embodiment, window 44 is a sapphire window with a thickness of about 180 µm.

Figure 11:
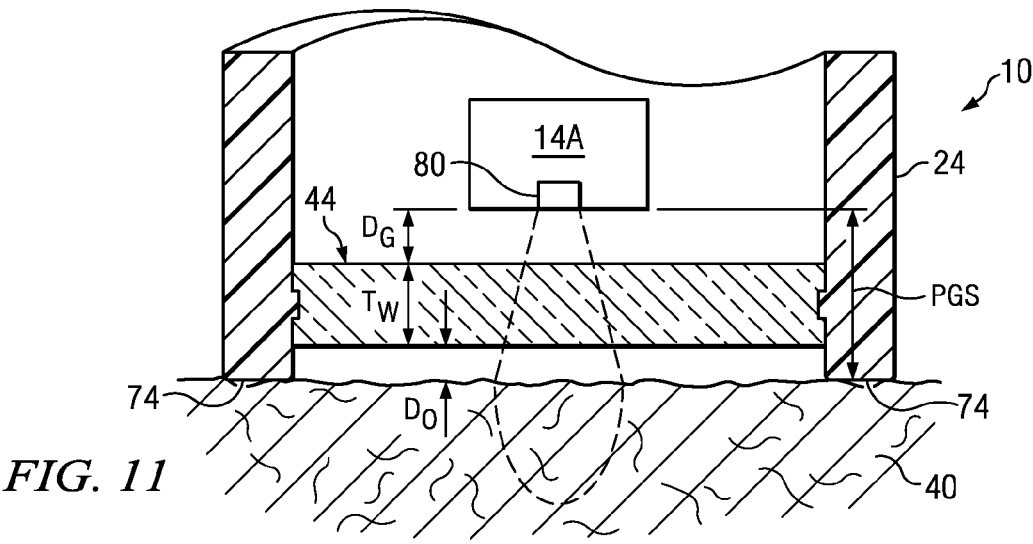
FIG. 11 illustrates a simplified cross-sectional side view of an example direct exposure embodiment that includes an edge emitting laser diode and a window offset from the skin.

FIG. 11 illustrates an example configuration in which the window 44 is set back from the skin by an offset distance ($D_O$), with another part of the treatment tip forming the skin-contacting surface 74. Such offset may be provided for any suitable reason, e.g., to protect the window from damage, to keep the window clean, or to avoid friction between the window and the skin. The proximity gap spacing (PGS) in this configuration is composed of the thickness of the window 44 ($T_W$), the gap distance ($D_G$) between the emitting surface 82 and the window 44, and the offset distance ($D_O$) of the window 44.

Figure 12:
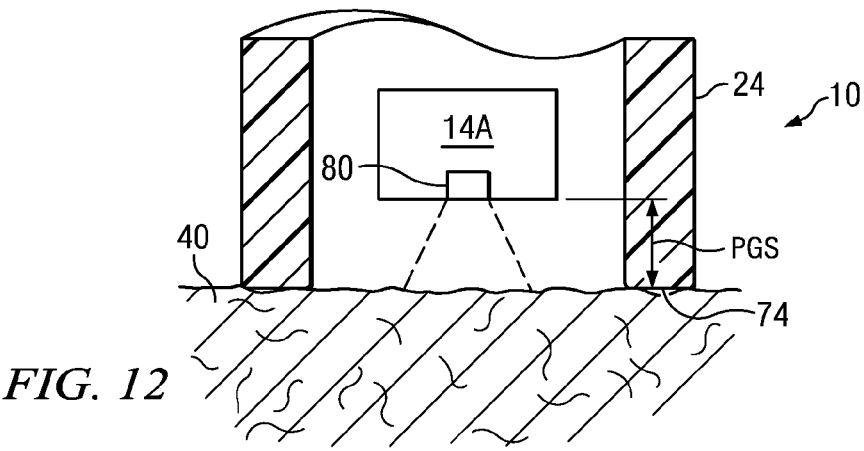
FIG. 12 illustrates a simplified cross-sectional side view of an example direct exposure embodiment that includes an edge emitting laser diode separated from the skin by only an air gap.

FIG. 12 illustrates an example configuration that excludes a window, such that the emitter 80 is exposed to open air. Thus, the proximity gap spacing (PGS) may be set at any desired distance, or even zero (i.e., with the emitting surface 82 touching the skin). However, the edge emitting laser diode 14A may be set back from the skin-contacting surface 74 by some distance, e.g., to protect the edge emitting laser diode from damage, to keep the edge emitting laser diode clean, to avoid friction between the edge emitting laser diode and the skin, or to provide some distance for the beam to diverge (in particular, in the fast axis direction) by a suitable amount to form a suitable treatment spot size on the skin or eye safety or other benefits.

Figure 13:
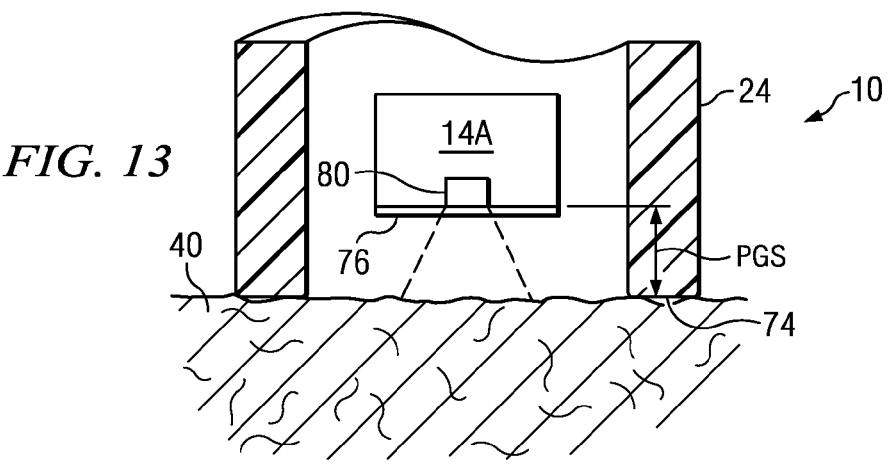
FIG. 13 illustrates a simplified cross-sectional side view of an example direct exposure embodiment that includes an edge emitting laser diode having a covering film and separated from the skin by only an air gap.

FIG. 13 illustrates an example configuration that excludes a window, but includes a film or other coating over the leading surface of edge emitting laser diode 14A, e.g., to protect the edge emitting laser diode from damage, provide electrical isolation, or for other purposes. The proximity gap spacing (PGS) may be set at any desired distance (limited only by the film thickness), or even such that the film-covered emitting surface 82 touches the skin. However, as discussed above regarding FIG. 12, the edge emitting laser diode 14A may be set back from the skin-contacting surface 74 by some distance, e.g., to protect the edge emitting laser diode from damage, to keep the edge emitting laser diode clean, to avoid friction between the edge emitting laser diode and the skin, or to provide some distance for the beam to diverge (in particular, in the fast axis direction) by a suitable amount to form a suitable treatment spot size on the skin.

Figure 14:
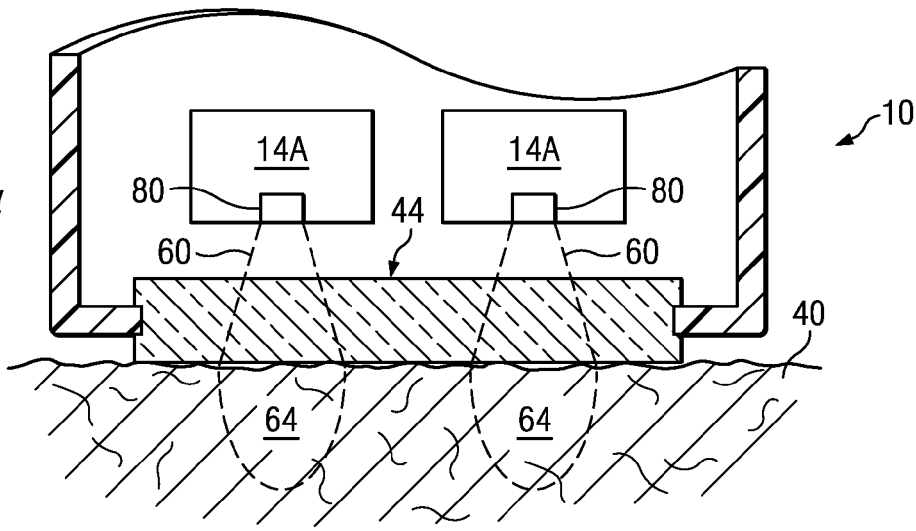
FIG. 14 illustrates a simplified cross-sectional side view of an example direct exposure embodiment that includes multiple edge emitting laser diodes and a window in contact with the skin.

FIG. 14 illustrates an example configuration of device 10 similar to the configuration of FIG. 10 but including two edge emitting laser diodes 14A, each generating a discrete beam 60. Device 10 may include any other number of edge emitting laser diodes 14A, arranged in any suitable manner, e.g., in a row, a two-dimensional array, or any other manner. Each edge emitting laser diode 14A in device 10 may be arranged with the proximity gap spacing between the respective emitter surface 82 and the skin-contacting surface 74, or different edge emitting laser diodes 14A may be arranged to have different proximity gap spacing (PGS), e.g., to provide multiple different treatment spot sizes, shapes, or energy intensities at the skin. Two or more edge emitting laser diodes 14A may similarly be arranged in any of the configurations shown in FIGS. 10-13, as well as FIGS. 15-16 discussed below. Any of these configurations may similarly utilize laser diode bars or VCSELs with single beam or multiple beams, as discussed below.

Figure 15:
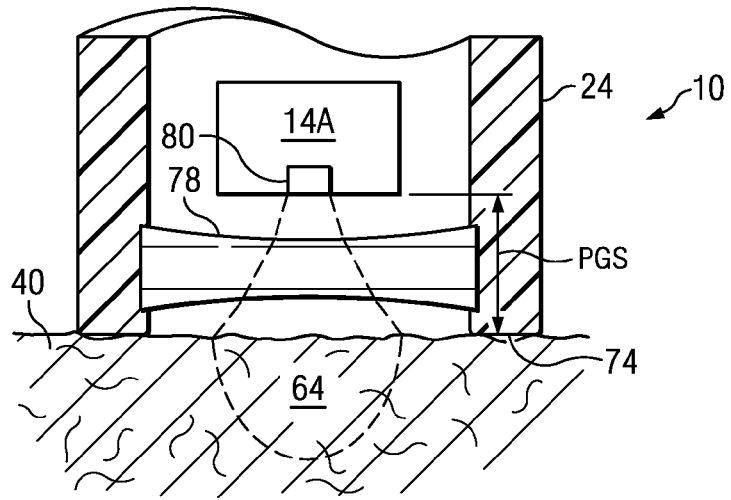
FIG. 15 illustrates a simplified cross-sectional side view of an example indirect exposure embodiment that includes an edge emitting laser diode and a downstream concave lens.
Figure 16:
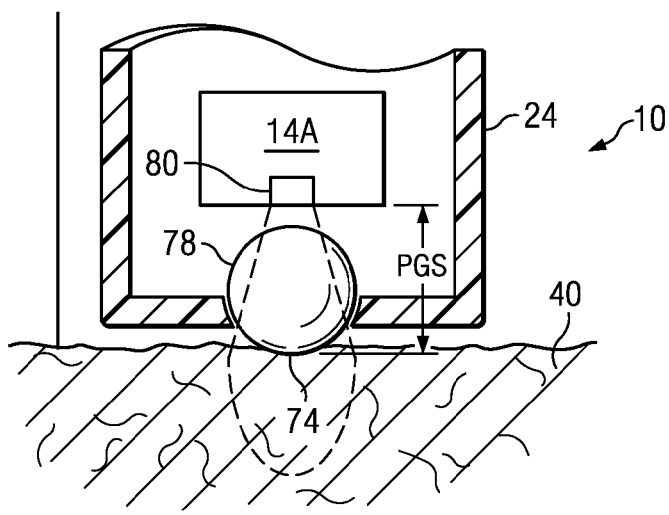
FIG. 16 illustrates a simplified cross-sectional side view of an example indirect exposure embodiment that includes an edge emitting laser diode and a downstream ball lens.

FIGS. 15-16 illustrate example indirect exposure configurations (i.e., including optics between the laser and the skin), which may also be configured for "close proximity" radiation, depending on the proximity gap spacing or "PGS" of the particular embodiment. Thus, in certain embodiments, device 10 configured as shown in FIG. 15 or 16 may have a proximity gap spacing of less than or equal to 10 mm, 5 mm, 2 mm, 1 mm, 500 µm, 200 µm, or even 100 µm in particular configurations.

FIG. 15 illustrates an example configuration of device 10 including a concave lens 78 positioned between edge emitting laser diode emitter 80 and the skin. Convex lens 78 may act to increase the divergence of the beam 60 in one or more axis (e.g., fast axis and/or slow axis), e.g., to provide a desired spot size or shape, and/or to provide increased eye safety. The lens 78 may be set back from the skin-contacting surface 74, as shown in FIG. 15, or may alternatively be arranged to contact the skin directly. Alternatively, a convex lens could be used to decrease the divergence of the beam 60 in one or more axis (e.g., fast axis and/or slow axis), e.g., to provide a desired spot size or shape.

FIG. 16 illustrates an example configuration similar to FIG. 15, but including a cylindrical lens or a ball lens 79 instead of convex lens 78. Cylindrical or ball lens 79 may act to increase the divergence of the beam 60 in one or more axis (e.g., fast axis and/or slow axis), e.g., to provide a desired spot size or shape, and/or to provide increased eye safety. Like lens 78 discussed above, lens 79 may be set back from the skin-contacting surface 74, or may alternatively be arranged to contact the skin directly, as shown in FIG. 16.

In other embodiments, any other type of lens (e.g., aspheric) or other optic may be provided to affect the beam 60 as desired.

Figure 17A:
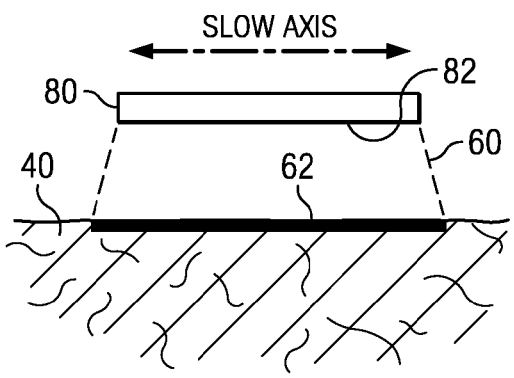
FIGS. 17A-17C illustrate the asymmetrical divergence of a beam emitted from an edge emitting laser diode, in embodiments in which the proximity gap spacing is extremely small.
Figure 17B:
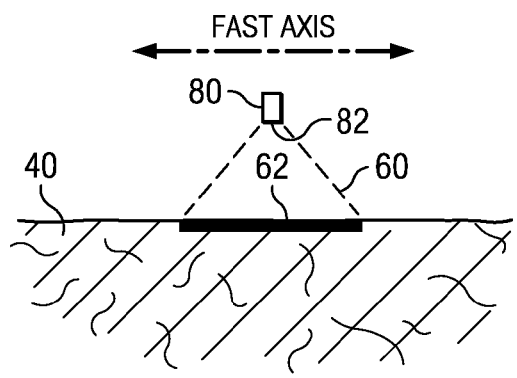
Figure 17C:
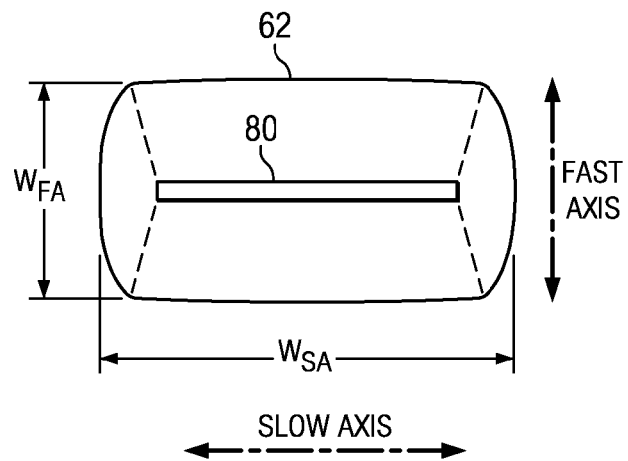

FIGS. 17A-17C illustrate the asymmetrical divergence of a beam 60 emitted from an edge emitting laser diode, in embodiments in which the proximity gap spacing is extremely small. A typical edge emitting laser diode includes an elongated rectangular emitter 80 having a long side and a short side. For example, an edge emitting laser diode emitter 80 may be about 1 µm by 100 µm, or about 5 µm by 95 µm.

FIG. 17A illustrates a long-side view of an edge emitting laser diode emitter 80, and illustrates the relatively slow divergence of the beam 60 in the slow axis. FIG. 17B illustrates a short-side view of edge emitting laser diode emitter 80 (perpendicular to the long-side view), and illustrates the relatively fast divergence of the beam 60 in the fast axis. FIG. 17C illustrates a top-down view showing edge emitting laser diode emitter 80 and a corresponding treatment spot 62 formed by edge emitting laser diode emitter 80, indicating the divergence of the beam 60 in both the fast axis and slow axis to form a treatment spot 62 having a generally oval or rounded-rectangular shape, which is elongated in the slow-axis direction. A treatment spot 62 elongated in the slow-axis direction, such as shown in FIG. 17C, may be produced by using an extremely small proximity gap spacing (e.g., less than the slow-axis width of the laser diode emitter surface or facet, e.g., about 100 µm). FIG. 17C does not account for any "smearing" or "blurring" of the treatment spot 62 due to the movement of device 10 due to movement of device 10.

FIGS. 18A-18C are similar to FIGS. 17A-17C, but correspond to configurations with a larger proximity gap spacing (e.g., about 500 µm for an emitter surface or facet having a slow-axis width of about 100 µm), whereby the longer propagation of the divergent beam 60 to the skin surface allows the fast axis divergence to overcome the slow axis divergence. Thus, the resulting treatment spot 62 may be elongated in the fast axis direction, as shown in FIG. 18C. Like FIG. 17C, FIG. 18C does not account for any "smearing" or "blurring" of the treatment spot 62 due to the movement of device 10 due to movement of device 10.

Figure 19A:
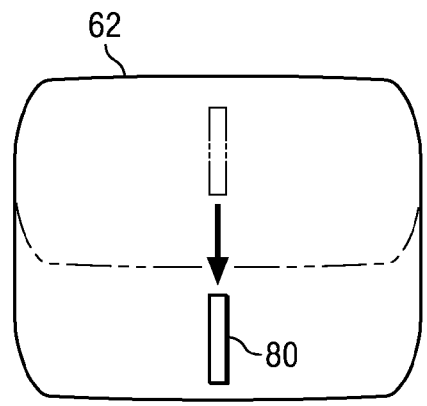
FIG. 19A-19B illustrates smearing or blurring of a treatment spot due to movement of the device across the skin during the treatment pulse.

FIG. 19A illustrates a treatment spot 62 formed by edge emitting laser diode emitter 80 emitting a beam pulse while device 10 is glided across the skin in the direction of the arrow, with emitter 80 moving the dashed-line image of emitter 80 to the solid-line image of emitter 80 during the pulse. Thus, the illustration shows the "smearing" or "blurring" of the treatment spot 62 due to the movement of device 10 during the beam pulse. In this orientation, the device movement may smear or blur the treatment spot 62 perpendicular to the elongated direction of the instantaneous spot, by an amount that depends at least upon the pulse duration and the manual glide speed. The longer the pulse duration or the faster the manual glide speed, the greater the elongation (blurring) of spot 62 in the glide direction. In the example shown in shown in FIG. 19A, the amount of blurring produces a generally circular or rounded-rectangular spot 62.

Figure 19B:
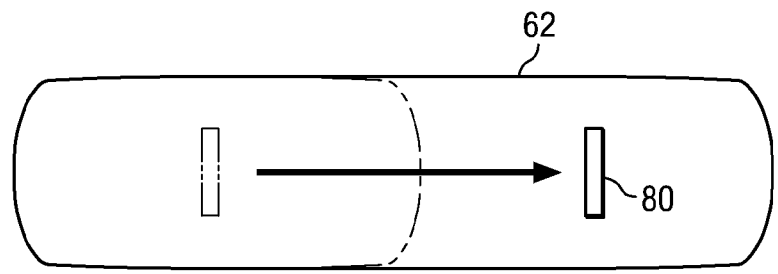

Like FIG. 19A, FIG. 19B illustrates a treatment spot 62 formed by edge emitting laser diode emitter 80 emitting a beam pulse while device 10 is glided across the skin in the direction of the arrow, with emitter 80 moving the dashed-line image of emitter 80 to the solid-line image of emitter 80 during the pulse. However, in the example shown in FIG. 19B, the device is moved in the elongated direction of the emitter 80, rather than perpendicular to the elongated direction of the emitter 80 as shown in FIG. 19A. Thus, the smearing or blurring of the treatment spot 62 caused by the device movement may increase the elongation of the resulting treatment spot 62.

Thus, it should be understood from the discussion above that the exact shape and size of the resulting treatment spot 62 may depend on a variety of factors, including at least (a) the size and shape of the particular emitter 80, (b) the orientation of the emitter 80 relative to the manual glide direction, (c) the proximity gap spacing between the emitter surface 82 and the skin, (d) the pulse duration, and (e) the manual glide speed. Any one or more (or all) of parameters (a)-(d) may be selected or controlled by device 10, and a desired manual glide speed may be encouraged (e.g., by instructing the user) to provide treatment spots 62 having a desired shape and size.

Figure 20:
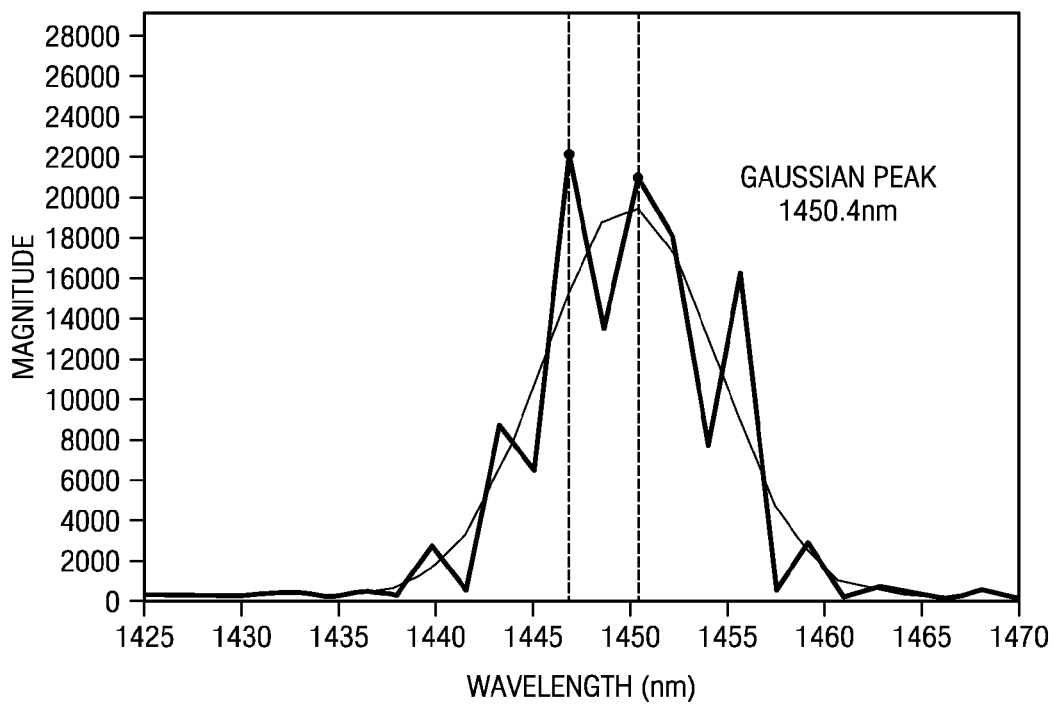
FIG. 20 is a plot of a detected wavelength profile of laser radiation received at a target surface from an example edge emitting laser diode.

FIG. 20 is a plot of a detected wavelength profile of laser radiation received at a target surface from an example edge emitting laser diode. In this example, the wavelength profile defines an approximately Gaussian peak at 1450.4 nm.

Figure 21A:
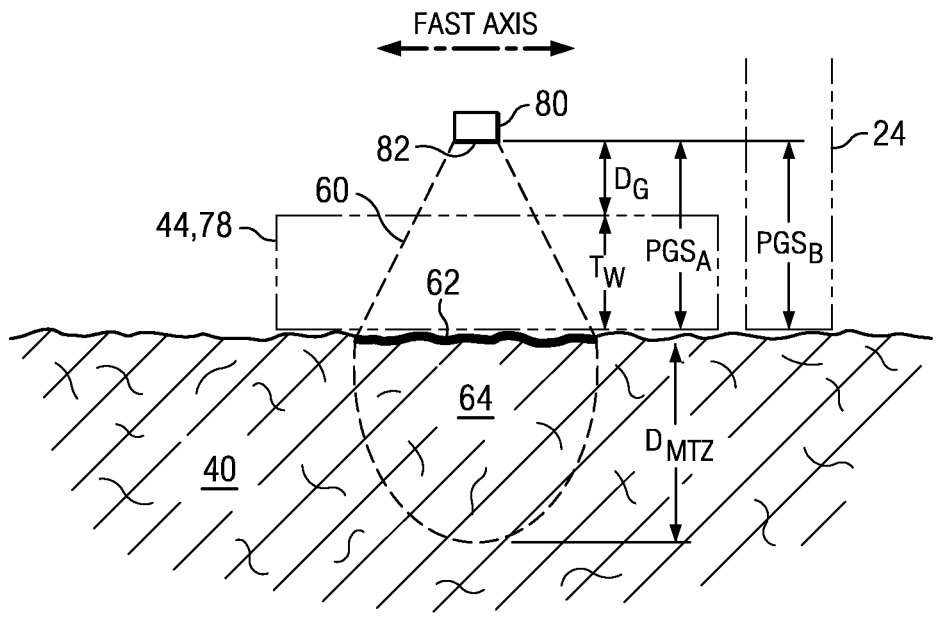
FIGS. 21A and 21B illustrate example dimensions for a treatment spot and corresponding MTZ generated by an edge emitting laser diode configured for direct exposure and/or close proximity radiation, according certain embodiments.
Figure 21B:
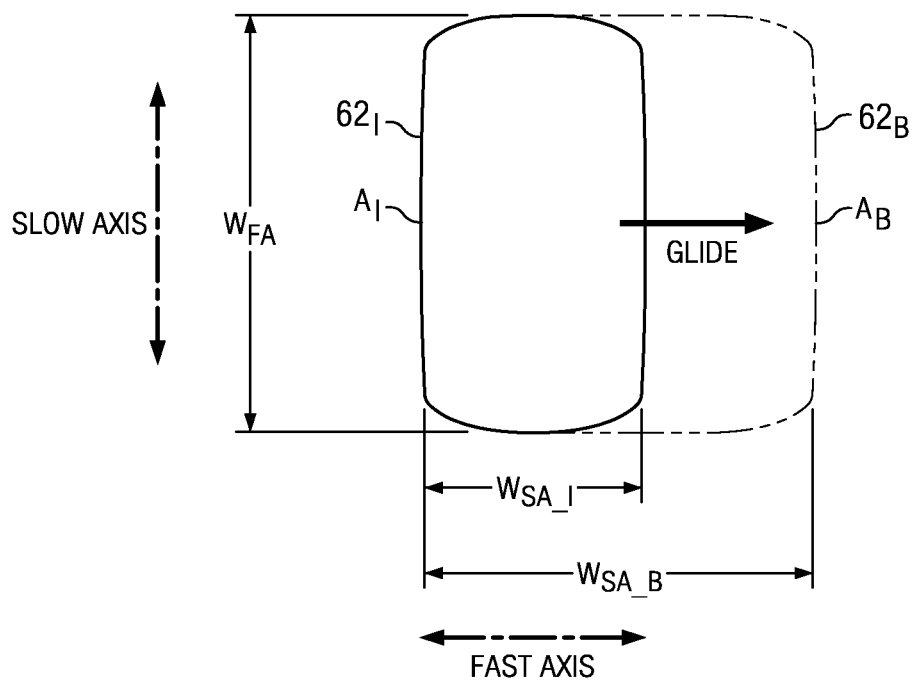

FIGS. 21A and 21B illustrate example dimensions for a treatment spot 62 and corresponding MTZ 64 generated by an edge emitting laser diode configured for direct exposure and/or close proximity radiation, e.g., according to any of the example configurations of FIGS. 10-16. As shown in FIG. 21, an edge emitting laser diode emitter 80 is positioned above the skin 40 with either a window 44 (i.e., not an optic 16), a lens 78 (i.e., an optic 16), or nothing (e.g., air only) positioned between the emitting surface 82 and the skin 40. Depending on the particular configuration, the proximity gap spacing (PGS) between the emitting surface 82 of the edge emitting laser diode and the skin-contacting surface of device 10 is indicated as $PGS_A$ (for embodiments in which window 44 or lens 78 directly contacts the skin) or $PGS_B$ (for embodiments in which window 44 or lens 78 is set back from the skin by some distance). Where the proximity gap spacing is indicated as $PGS_A$ (i.e., embodiments in which window 44 or lens 78 directly contacts the skin), the PGS is equal to the thickness of the window 44 or lens 78 ($T_W$) plus the gap distance ($D_G$) between the emitting surface 82 and the window 44 or lens 78. As discussed above, in some embodiments emitter 80 may be placed directly onto the window 44 or lens 78, such that the gap distance ($D_G$) is effectively zero.

FIG. 21A also indicates the treatment spot 62 on the skin surface, as well as the depth of the MTZ 64 extending below the treatment spot 62, indicated as $D_{MTZ}$.

FIG. 21B illustrates the dimensions of the treatment spot 62 on the skin surface, with the instantaneous treatment spot $62_I$ shown in solid line and the "blurred" treatment spot $62_B$ (due to gliding of device 10 across the skin during the delivery of the beam pulse) shown in dashed line. The instantaneous treatment spot $62_I$ is defined by a fast axis direction width $W_{FA}$, a slow axis direction width $W_{SA\_I}$, and an area $A_I$. The blurred treatment spot $62_B$ is defined by a fast axis direction width $W_{FA}$, a slow axis direction width $W_{SA\_B}$, and an area $A_B$.

In some embodiments, one or more parameters of device 10 may be selected or controlled to control or limit the amount of blurring of treatments spots 62, e.g., to provide an effective spot size and/or fluence or energy density at the skin within individual treatments spots 62 (e.g., to achieve the desired dermatological effect in the skin). For example, in some embodiments, one or more of (a) the pulse duration and (b) the fluence or energy density of the emitted beam 60 may be controlled or limited based on an assumed manual glide speed (e.g., 2-6 cm/s), a measured manual glide speed, or a measured displacement of device 10 across the skin, for example, to limit the blurring of treatments spots 62 to a defined maximum blur factor. As stated above, the blur factor may be defined as the ratio of the area of the blurred treatment spot 62 (with blurring caused by movement of device 10) to the area of the instantaneous treatment spot size. Thus, to illustrate, a blur factor of 1.0 indicates no blurring, a blur factor of 2.0 indicates a doubling of the treatment spot size area, and a blur factor of 3.0 indicates a tripling of the treatment spot size area.

In general, the larger the blur factor, the lower the fluence or energy density at the skin within the area of the blurred treatment spot. In some embodiments or device settings, a blur factor of up to about 3.0 is generally acceptable for providing effective MTZs for a fractional treatment. In other embodiments or device settings, a blur factor of up to about 2.5 or up to about 2.0 is generally acceptable for providing effective MTZs for a fractional treatment. Thus, in some embodiments, one or more device parameters (e.g., the pulse duration and/or the fluence or energy density of emitted beams 60) may be selected controlled to limit the blur factor to less than about 3.0, 2.5, or 2.0, depending on the selected limit. Certain embodiments limit the blur factor to less than about 1.8 or less than about 1.5. Other embodiments or device settings may allow a blur factor of up to about 3.5 or 4.0. Other embodiments or device settings may allow even larger blur factors.

In some embodiments, the pulse duration may be limited to a defined value (e.g., 5 ms) based on an assumed range of manual glide speeds (e.g., 2-8 cm/s) to limit the blur factor to about 2.0. Further, it has been determined that an MTZ 64 need not be circular or axis-symmetric in shape to be effective, and can be elliptical or elongated to a certain extent, e.g., as caused by a manual glide speed between about 6 cm/s and 10 cm/s for certain embodiments.

Table 5 shows relevant parameter values for a variety of example embodiments of device 10, with reference to FIGS. 21A and 21B.

TABLE 5

| Parameter | Example Embodiment 1 | Specific Example of Embodiment 1 | Example Embodiment 2 | Specific Example of Embodiment 2 |
|---|---|---|---|---|
| Radiation source | Single beam edge emitting laser diode | Single beam edge emitting laser diode | Single beam laser diode | Single beam laser diode |
| emitter surface ($\mu m \times \mu m$) | 100 (slow-axis) × 5 (fast-axis) | 100 (slow-axis) × 5 (fast-axis) | 100 (slow-axis) × 5 (fast-axis) | 100 (slow-axis) × 5 (fast-axis) |
| window or lens? | window | window | window | window |
| beam divergence at skin surface (fast axis, slow axis) | 35°-45° fast axis, 6°-12° slow axis, | 45° fast axis 10° slow axis | 35°-45° fast axis 6°-12° slow axis, | 45° fast axis 10° slow axis |
| $T_W$ ($\mu m$) | 150-250 | 180 | 50-150 | 130 |
| $D_G$ ($\mu m$) | 200-500 | 320 | 50-150 | 130 |
| PGS ($\mu m$) | 350-750 | 500 | 100-300 | 260 |
| $W_{FA}$ ($\mu m$) | 225-625 | 419 | 70-255 | 220 |
| $W_{SA\_I}$ ($\mu m$) | 135-260 | 187 | 110-165 | 145 |
| $A_I$ ($mm^2$) | 0.03-0.16 | 0.078 | 0.01-0.04 | 0.032 |
| manual glide speed (cm/s) | 2-6 | 4 | 1-4 | 2 |
| $W_{SA\_B}$ ($\mu m$) | 155-740 | 307 ($W_{SA\_B}$; glide in slow-axis direction) | 120-765 | 225 ($W_{SA\_B}$; glide in slow-axis direction) |
| $A_B$ ($mm^2$) | 0.03-0.46 | 0.129 | 0.01-0.20 | 0.050 |
| Pulse duration (ms) | 1-8 | 3 | 1-15 | 4 |
| Power (W) | 2-6 | 4 | 1-4 | 3 |
| Total energy per pulse (mJ) | 5-15 | 12 | 5-15 | 12 |
| Energy density (J/cm$^2$) | 1.1-50 | 9.3 | 2.5-150 | 24 |
| $D_{MTZ}$ ($\mu m$) | 100-400 | 260 | 120-700 | 350 |
| Pulse frequency rate (Hz) | 10-30 | 15 | 10-40 | 20 |

| Parameter | Example Embodiment 3 | Specific Example of Embodiment 3 | Example Embodiment 4 | Specific Example of Embodiment 4 |
|---|---|---|---|---|
| Radiation source | Single beam laser diode | Single beam laser diode | Single beam laser diode | Single beam laser diode |
| emitter surface ($\mu m \times \mu m$) | 100 (slow-axis) × 5 (fast-axis) | 100 (slow-axis) × 5 (fast-axis) | 100 (slow-axis) × 5 (fast-axis) | 100 (slow-axis) × 5 (fast-axis) |
| window or lens? | convex rod lens | convex rod lens | neither (air) | neither (air) |
| beam divergence at skin surface (fast axis, slow axis) | 2°-8° fast axis, 6°-12° slow axis | 5° fast axis 10° slow axis | 35°-45° fast axis, 6°-12° slow axis | 45° fast axis 10° slow axis |
| $T_W$ ($\mu m$) | 50-150 | 130 | N/A | N/A |
| $D_G$ ($\mu m$) | 400-2500 | 2000 | 50-150 | 100 |
| PGS ($\mu m$) | 450-3000 | 2130 | 50-150 | 100 |

TABLE 5-continued

| | | | | |
|---|---|---|---|---|
| $W_{FA}$ (μm) | 20-425 | 191 | 35-130 | 88 |
| $W_{SA\_I}$ (μm) | 145-730 | 473 | 105-130 | 117 |
| $A_I$ (mm$^2$) | 0.003-0.31 | 0.090 | 0.004-0.02 | 0.010 |
| manual glide speed (cm/s) | 2-6 | 4 | 1-4 | 2 |
| $W_{SA\_B}$ (μm) | 40-900 | 351 ($W_{FA\_B}$; glide in fast-axis direction) | 45-450 | 168 ($W_{FA\_B}$; glide in fast-axis direction) |
| $A_B$ (mm$^2$) | 0.006-0.66 | 0.166 | 0.005-0.06 | 0.020 |
| Pulse duration (ms) | 1-8 | 4 | 1-8 | 4 |
| Power (W) | 2-6 | 3 | 2-6 | 3 |
| Total energy per pulse (mJ) | 5-15 | 12 | 5-15 | 12 |
| Energy density (J/cm$^2$) | 0.8-250 | 7.2 | 8-300 | 60 |
| $D_{MTZ}$ (μm) | 100-700 | 250 | 250-700 | 450 |
| Pulse frequency rate (Hz) | 10-30 | 15 | 10-40 | 30 |

Laser Diode Bars

As discussed above, in some embodiments, radiation source 14 is an laser diode bar (or multiple laser diode bars) including multiple emitters, each acting as a discrete beam source that generates a discrete laser beam. In a typical laser diode bar, the beam emitted from each beam source (emitter) of the laser diode bar has a beam divergence of nearly 45° in the fast axis direction and about 10° in the slow axis.

Due to the rapid divergence in the fast axis direction, the laser diode bar provides a significant beam spread in this fast axis direction, in the absence of optical elements provided downstream of the laser diode bar. Therefore, as with an edge emitting laser diode, in order to capture a desired portion of the beam energy (and/or maintain a desired beam intensity), certain embodiments are configured as close proximity devices in which the proximity gap spacing (the spacing between emitting surfaces of the laser diode bar and the skin-contacting surface 74 of device 10) is less than or equal to 10 mm. In certain laser diode bar embodiments, device 10 may have a proximity gap spacing of less than or equal to 5 mm, 2 mm, 1 mm, 500 μm, 200 μm, or even 100 μm, depending on the desired size and/or intensity of the treatment spots 62 generated by the laser diode bar.

The multiple beams emitted by the multiple emitters of an laser diode bar may (a) remain separate during their propagation to the skin to form multiple, spaced-apart treatment spots 62 on the surface of the skin, or (b) partially or substantially combine during their propagation to the skin (due to the divergence of the individual beams) to form a single contiguous treatment spot 62 with substantially uniform or spatially modulated energy profile, depending at least on (a) the proximity gap spacing between the emitting surfaces of the laser diode bar and the skin, (b) the size and shape of each emitter of the laser diode bar, and (c) the fill factor of the laser diode bar.

FIGS. 22A-23B illustrate example embodiments in which the multiple beams emitted by the multiple emitters of an laser diode bar remain separate and form multiple, spaced-apart treatment spots 62 on the skin. Such embodiments may be suitable or advantageous for certain applications or treatments, e.g., certain fractional treatments. In contrast, FIGS. 24A-24B illustrate an example embodiment in which the multiple beams emitted by the multiple emitters of an laser diode bar combine during their propagation to the skin (due to the divergence of the individual beams) to form a single contiguous treatment spot 62. In particular, the example embodiment of FIGS. 24A-24B includes a "high fill-factor" laser diode bar that promotes the combination of the individual beams to form a single contiguous treatment spot 62 on the skin. Such embodiments may be suitable or advantageous for certain applications or treatments, e g, hair removal treatments, bulk heating for skin tightening, or acne, for example, or non-ablative wrinkle treatments.

Turning first to FIGS. 22A-23B, FIG. 22A illustrates a simplified cross-sectional side view of an embodiment similar to the embodiment of FIG. 10, but including an laser diode bar 14B instead of a single-emitter edge emitting laser diode 14A as the radiation source, Laser diode bar 14B includes multiple emitters 80 arranged in a row, with each emitter 80 acting as a discrete beam source that generates a discrete laser beam 60. The multiple beams 60 emitted by the multiple emitters 80 of the laser diode bar 14B form a linear array of spaced-apart treatment spots 62 on the skin, and thus a corresponding linear array of spaced-apart MTZs 64 in the skin. This embodiments may be suitable for fractional treatment, for example. Laser diode bar 14B may include any suitable number of emitters 80.

Laser diode bar 14B may be controlled to deliver pulsed radiation, continuous wave (CW) radiation, or otherwise. FIG. 22B shows a two-dimensional array of treatment spots 62 formed by manually scanning an array of beams 30 onto the skin, e.g., by pulsing laser diode bar 14B while device 10 is moved across the skin in the indicated direction, e.g., in a gliding mode or stamping mode operation. Each pulse of the laser diode bar 14B generates a linear array 66 of treatment spots 62, such that moving device 10 in a direction generally perpendicular to the linear array 66 provided by each pulse creates a two-dimensional array 68 of treatment spots 62. Device 10 may be glided across the skin any suitable number of times and in any suitable direction(s) to cover a desired treatment area.

Figure 23A:
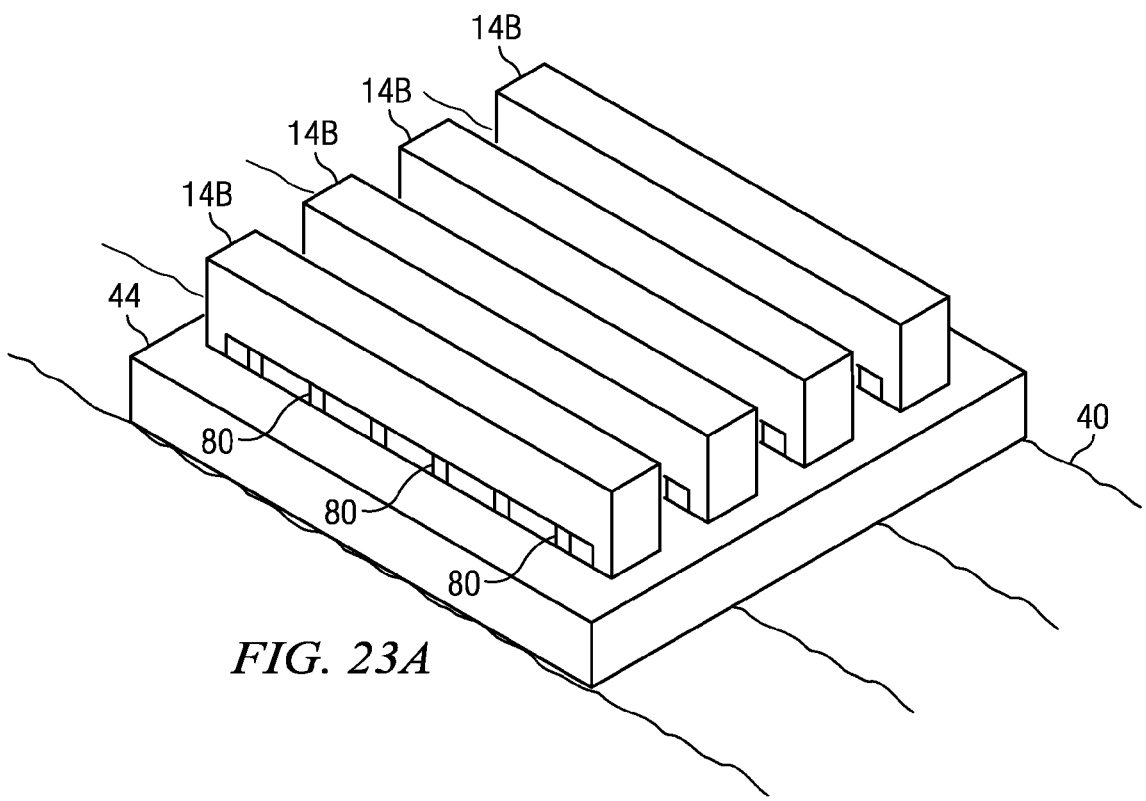
FIGS. 23A and 23B illustrate a configuration and example treatment spot array, respectively, for a device including multiple laser diode bars as the radiation source, according to certain embodiments.
Figure 24A:
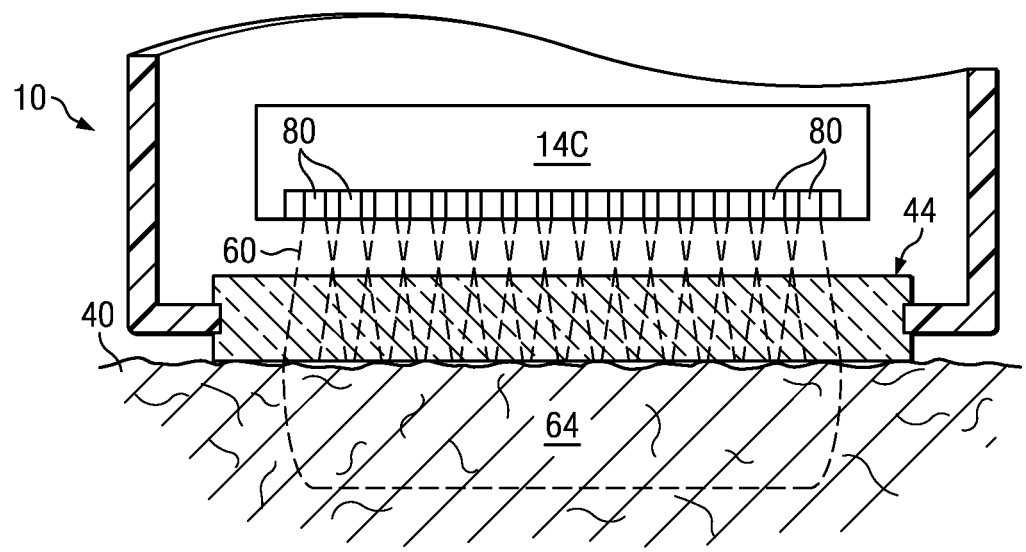
FIGS. 24A and 24B illustrate a configuration and example treatment spot, respectively, for a device including a high fill-factor laser diode bar as the radiation source, according to certain embodiments.
Figure 24B:
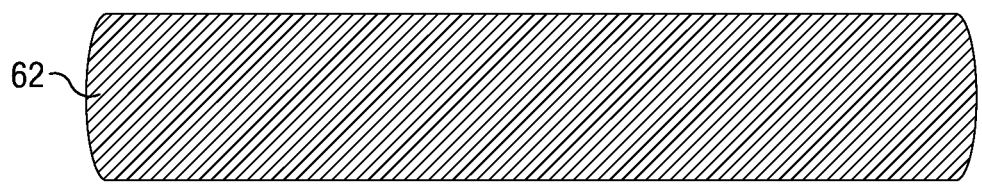

FIG. 23A illustrates a partial three-dimensional view of laser diode bars 14B and a window 44 for an embodiment of device 10 including multiple laser diode bars 14B arranged parallel to each other (e.g., to form a "stack"). Each emitter 80 of each laser diode bar 14B may act as a discrete beam source that generates a discrete laser beam 60, with the multiple beams 60 of the multiple laser diode bars 14B forming a two-dimensional array of spaced-apart treatment spots 62 on the skin, and thus a corresponding linear array of spaced-apart MTZs 64 in the skin.

Figure 23B:
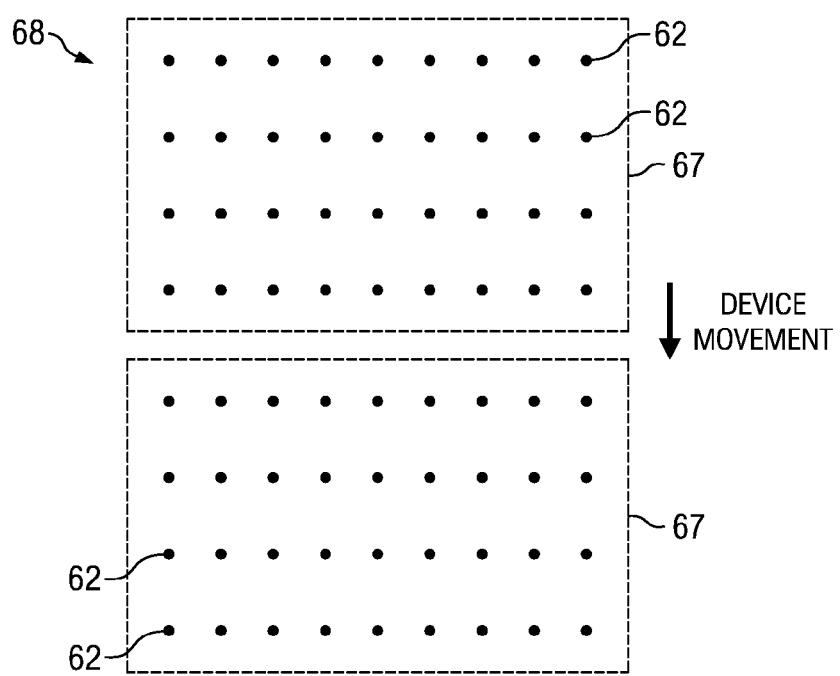

As discussed above, laser diode bars 14B may be controlled to deliver pulsed radiation, continuous wave (CW) radiation, or otherwise. In a pulsed embodiment, the multiple laser diode bars 14B may be pulsed simultaneously, time-sequentially in any defined order (or in random order), or in any other manner. FIG. 23B shows a two-dimensional array of treatment spots 62 formed by manually scanning an array of beams 30 onto the skin, e.g., by pulsing laser diode bars 14B while device 10 is moved across the skin in the indicated direction, e.g., in a gliding mode or stamping mode operation. In this example, the multiple laser diode bars 14B are pulsed simultaneously. Thus, each pulse of the laser diode bar 14B generates a two-dimensional array 67 of treatment spots 62, and the combination of moving device 10 and pulsing the multiple laser diode bars 14B creates a larger two-dimensional array 68 of treatment spots 62 extending in the direction of the device movement. Device 10 may be glided across the skin any suitable number of times and in any suitable direction(s) to cover a desired treatment area.

The example embodiments of FIGS. 22A-23B may utilize "low fill-factor" laser diode bars that provide sufficient spacing between adjacent emitters 80 for providing the resulting spaced-apart treatment spots 62 on the skin. In contrast, FIGS. 24A-24B include a "high fill-factor" laser diode bar that promotes the combination of the individual beams to form a single contiguous treatment spot 62 on the skin. In particular, the multiple beams emitted by the multiple emitters of the high fill-factor laser diode bar may combine during their propagation to the skin (due to the divergence of the individual beams) to form a single contiguous treatment spot 62.

As used herein, "high fill-factor" means a fill-factor of at least 50%, as compared to a "low-fill factor," defined as a fill-factor of less than 50%. The fill factor is defined as the total emitter active portion of the laser diode bar divided by the width of the entire laser diode bar, as defined in greater detail in co-pending U.S. Provisional Patent Application 61/563,491, the entire contents of which are hereby incorporated by reference. For some applications, using high fill-factor laser diode bars may provide one or more advantages as compared to low fill-factor laser diode bars. For example, a high fill-factor laser bar may provide a more uniform radiation image at the target surface. The beam profile from the high fill-factor laser diode bar, even in certain close proximity arrangements, is a substantially uniform line segment. Such uniform line segment may be suitable or desirable for certain applications or treatments, e.g., a gliding treatment normal to the line segment direction (e.g., for laser hair removal, bulk heating skin tightening, or other suitable treatments). In some embodiments, the high fill-factor laser diode bar may be used in conjunction with a sensor (e.g., a displacement sensor or a motion/speed sensor) to allow a treatment dose to be metered uniformly over a relatively large area.

Figure 22A:
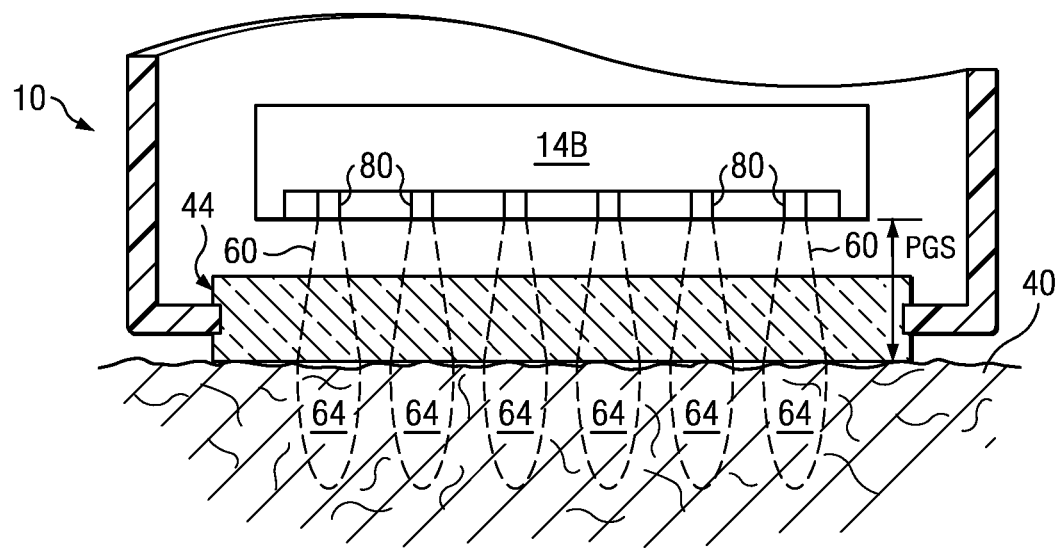
FIGS. 22A and 22B illustrate a configuration and example treatment spot array, respectively, for a device including a laser diode bar as the radiation source, according to certain embodiments.
Figure 22B:
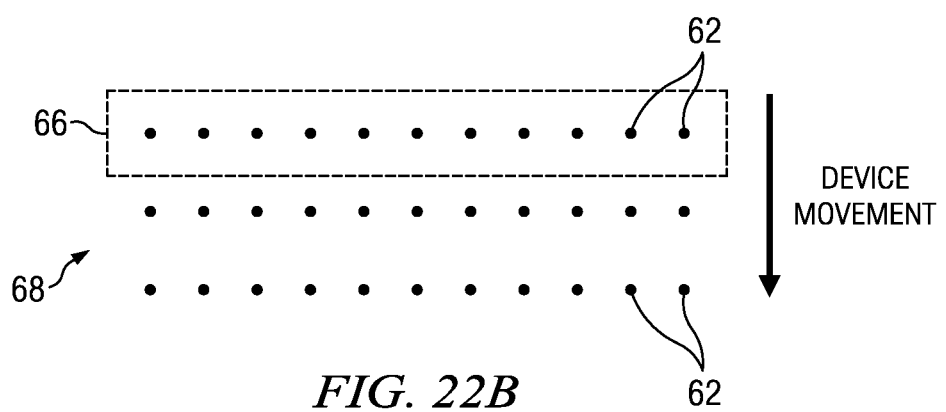

FIG. 24A illustrates an embodiment similar to that of FIG. 22A, but using a high fill-factor laser diode bar 14C. As shown, the beams 60 emitted by the multiple emitters 80 of the laser diode bar 14C combine with each other during their propagation to the skin to form a single contiguous treatment spot 62, and a corresponding single contiguous MTZ 64. FIG. 24B illustrates an example contiguous treatment spot 62 generated by laser diode bar 14C. Laser diode bar 14C may be pulsed, may provide continuous wave (CW) radiation, or may be otherwise controlled, in combination with movement of device 10 across the skin (e.g., in a gliding mode or stamping mode operation) to provide the desired size, shape, and pattern of treatment spots 62 suitable for the particular dermatological treatment, e.g., as described in more detail in incorporated co-pending U.S. Provisional Patent Application 61/563,491.

As discussed above, in some embodiments of device 10, laser diode bars (e.g., laser diode bars 14B/14C) may be configured for "direct exposure" radiation, "close proximity" radiation, or both, as such terms are defined and discussed herein. Further, laser diode bars may be arranged in any of the various configurations discussed herein regarding other types of radiation sources, e.g., laser diode bars may be arranged in any of the various configurations shown in FIGS. 10-16 with respect to embodiments including edge emitting laser diodes.

Figure 25:
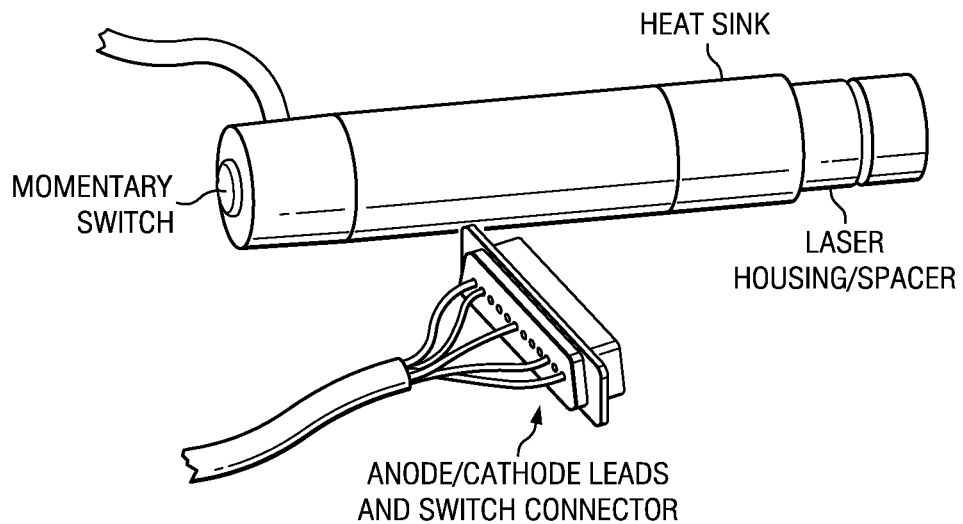
FIGS. 25 and 26 illustrate components of an example embodiment of a device in which the radiation source is laser diode bar including an array of 19 laser emitters that emit an array of beams to generate an array of treatment spots in each pulse.
Figure 26:
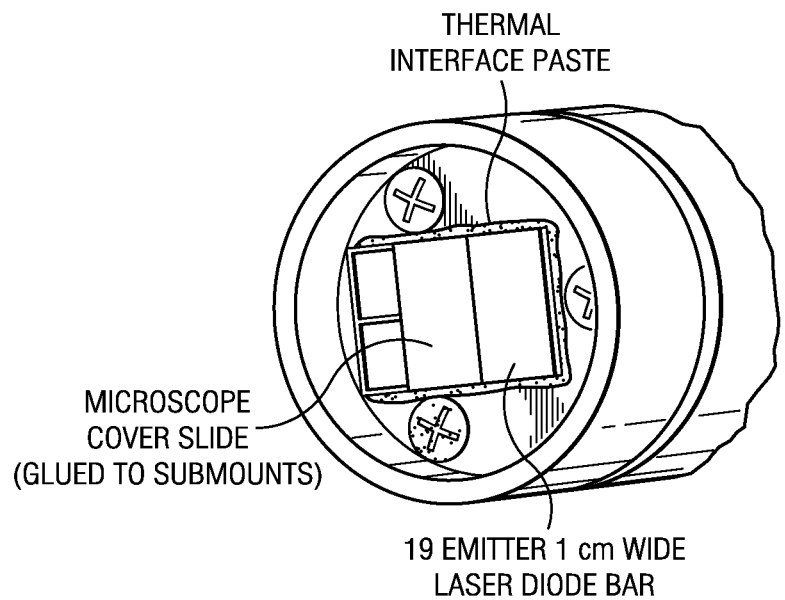

FIGS. 25 and 26 illustrate an example embodiment of device 10 in which the radiation source 14 is laser diode bar including an array of 19 laser emitters 80 that emit an array of beams 60 to generate an array of treatment spots 62 in a single pulse. The device can be constructed as a fully solid-state device with no optics or moving parts. Because the laser diode bar generates multiple treatment spots 62 in each pulse, the device may achieve faster treatment rate and may be less expensive per spot relative to a device using a single-emitter laser diode and/or may deliver a preferred dot pattern, such as more uniform spacing or reduced blurring or smearing of the spots, when manually moved across the skin.

VCSEL Lasers

Figure 27:
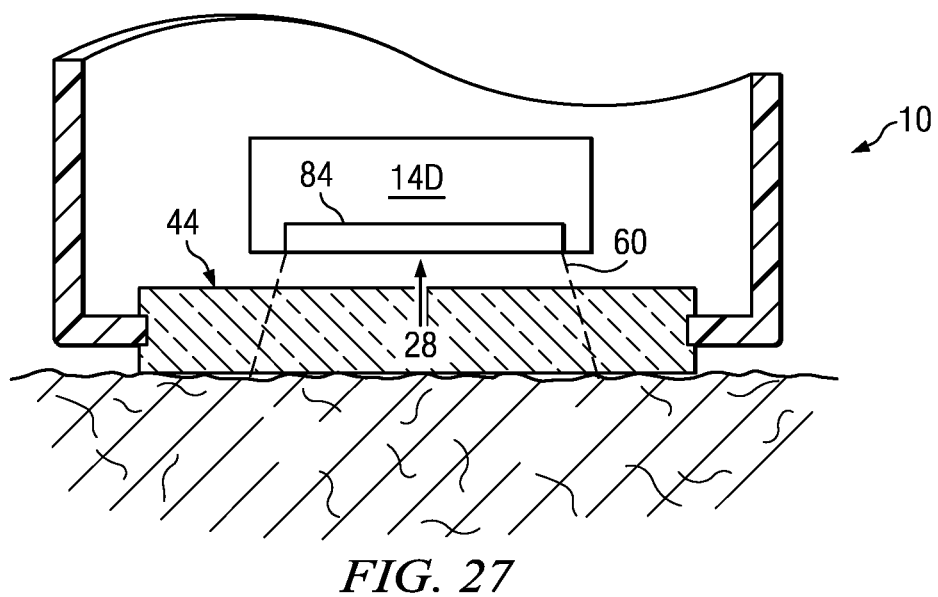
FIG. 27 illustrates an example direct exposure configuration of a device including a single-beam-source VCSEL laser as the radiation source, according to certain embodiments.
Figure 28:
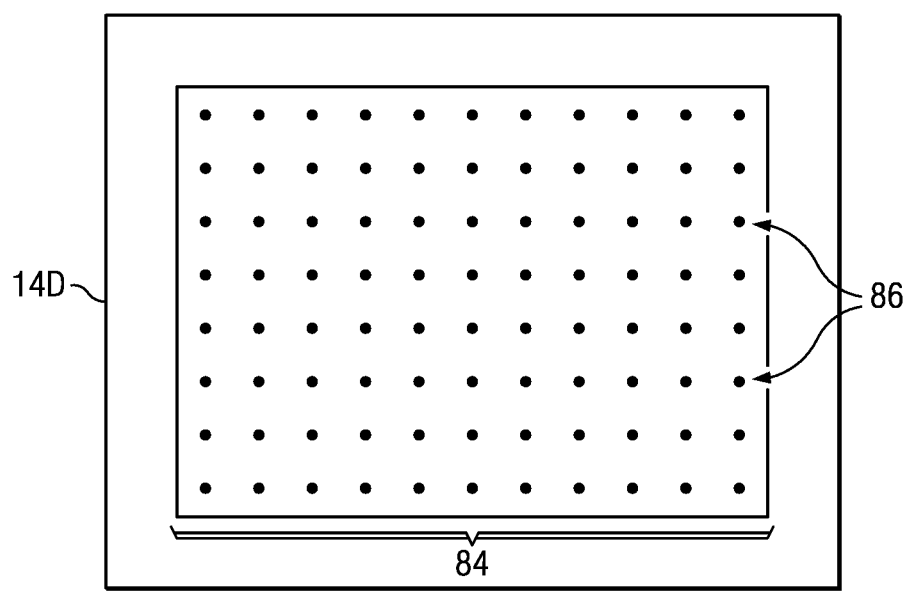
FIG. 28 illustrates an example arrangement of micro-emitters forming a single-beam-source VCSEL laser, according to an example embodiment.
Figure 29:
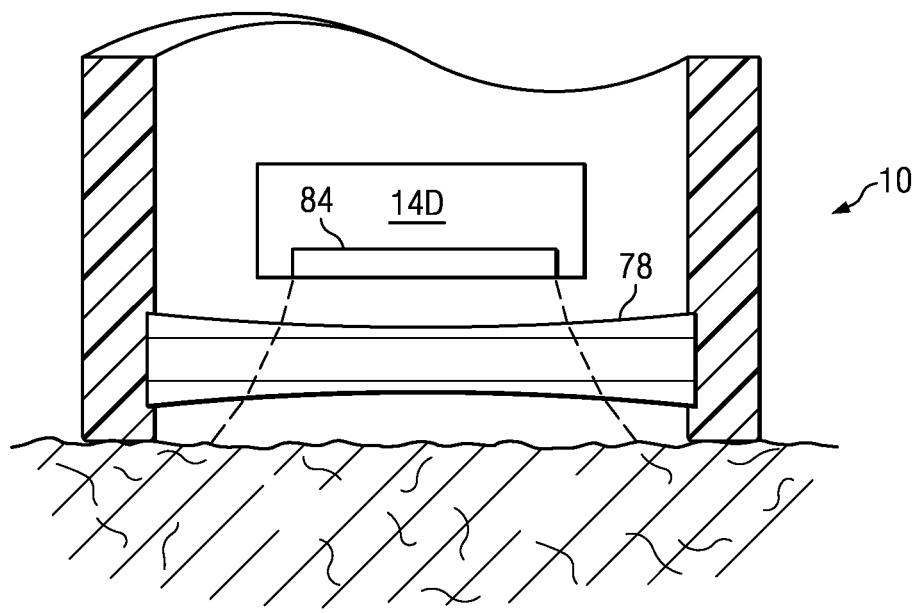
FIG. 29 illustrates an example indirect exposure arrangement of a single-beam-source VCSEL laser and downstream optic (concave lens), according to certain embodiments.

As discussed above, in some embodiments, device 10 includes one or more VCSEL (Vertical Cavity Surface Emitting Laser) lasers for generating one or more treatment beams. A VCSEL may be configured to generate a single energy beam (e.g., as shown in FIGS. 27-29) or multiple discrete energy beams (e.g., as shown in FIGS. 30-34). In some embodiments, a VCSEL can be configured to generate an array (1D or 2D) of discrete laser beams for creating an array (1D or 2D) of spaced-apart treatment spots 62 on the skin, e.g., to provide a fractional treatment.

FIG. 27 illustrates a simplified cross-sectional side view of an example embodiment of device 10 that includes a VCSEL 14D configured to generate a single energy beam for providing a single treatment spot 62 on the skin. VCSEL 14D may include an array 84 of micro-emitters 86, as shown in FIG. 29, which shows an emitter surface view of the example VCSEL 14D in the direction of arrow 28 shown in FIG. 27. Each micro-emitter 86 emits a divergent micro-beam, and the array of micro-beams combine (due to the divergence of the individual micro-beams) to form a single, generally uniform beam 60 for delivery to the skin, as shown in FIG. 27. Thus, in such embodiments, the micro-emitter array 84 acts as a single beam source to generate a single beam 60 that creates a single treatment spot 62 on the skin.

For at least some VCSELs, each micro-emitter 86 emits a circularly symmetrical micro-beam. For example, each micro-emitter 86 may emit a micro-beam having an axially-symmetric divergence angle of above 20° (e.g., conventional VCSELs), or a divergence angle of between 10° and 20° (e.g., certain surface relief and antiresonant reflecting optical waveguide structures), or a divergence angle of between 7° and 10°, or a divergence angle of below 7° (e.g., certain holey structures, such as photonic crystals and multi-leaf structures), or a divergence angle of about 6° (e.g., certain multi-leaf VCSELs), or a divergence angle of below 6°, e.g., between 5.1° and 5.5° (for certain photonic crystal vertical-cavity surface-emitting laser (PC-VCSEL)), e.g., as described in "*Reduction of the Far-Field Divergence Angle of an 850 nm Multi-Leaf Holey Vertical Cavity Surface Emitting Laser*," Zhou Kang et al., CHIN. PHYS. LETT. Vol. 28, No. 8 (2011) 084209; and "*Reduced divergence angle of photonic*

*crystal vertical-cavity surface-emitting laser,"* Anjin Liu et al., Appl. Phys. Lett. 94, 191105 (2009); doi:10.1063/1.3136859.

Micro-emitter array 84 may have any suitable shape, size, and configuration, and may include any suitable number of micro-emitters 86 arranged in any suitable pattern to form any suitable one-dimensional or two-dimensional array 84. For example, the micro-emitters 86 in an array 84 may be evenly spaced from each other, e.g., to provide a beam 60 having a generally uniform intensity profile, or may be unevenly spaced from each other, e.g., to provide a beam 60 having a selected non-uniform intensity profile suitable for a particular application or treatment. For example, micro-emitters 86 towards the outside of the array 84 may be spaced further apart from each other to provide a more rounded (i.e., less flat-topped or top hat-like) beam intensity profile, which may be suitable for particular applications or treatments. As another example, micro-emitters 86 towards the inside of the array 84 may be spaced further apart from each other to provide a more cusped beam intensity profile having a dip in intensity level near the center of the profile, which may be suitable for particular applications or treatments. Similarly, the emitters could be distributed to produce a flat-topped or Gaussian beam profile. Micro-emitters 86 may be arranged in any other suitable manner to provide any other desired beam intensity profile.

FIG. 29 illustrates a simplified cross-sectional side view of an example embodiment of device 10 that includes a single-beam-source VCSEL 14D (e.g., as discussed above regarding FIGS. 27-28) and an optic 78 downstream of the VCSEL. Optic 78 may be any type of lens (e.g., concave, convex, ball lens, cylindrical lens, aspherical lens, etc.) or other optic for affecting the radiation emitted by VCSEL 14D as desired. For example, optic 78 may be provided e.g., to increase or decrease the divergence of the resulting beam 60 delivered to the skin, such as to provide a desired spot size or shape, energy intensity level at the skin, and/or to provide increased eye safety. The downstream optic(s) may be provided directly on the VCSEL(s) via coatings, MEMs structures or otherwise, so may be monolithic with the VCSEL(s). Other optics examples are a microlens array, fiber(s), or fiber bundles, among others.

Figure 30:
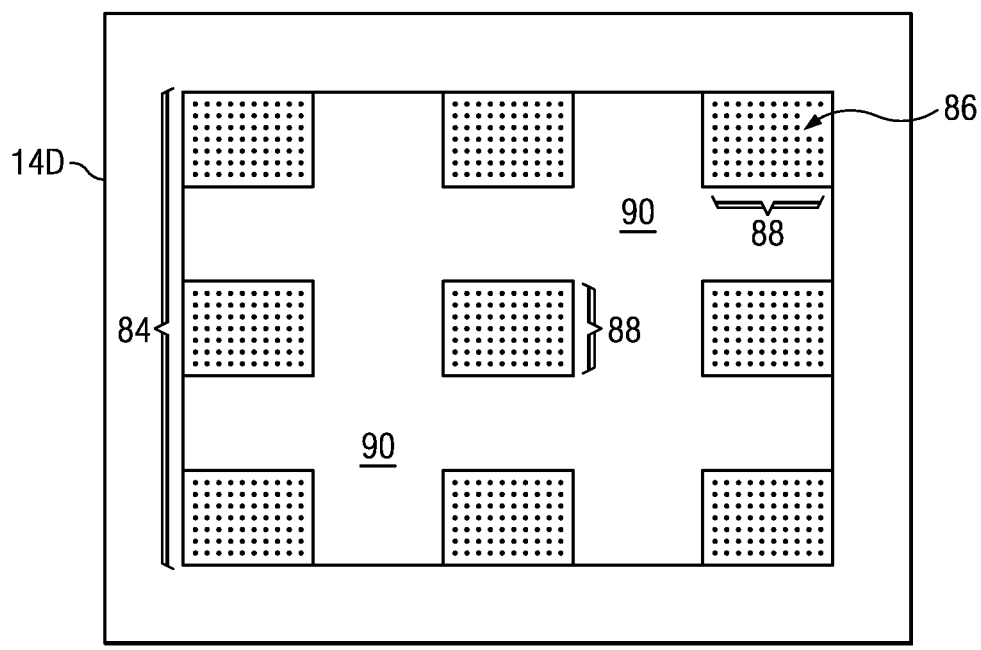
FIG. 30 illustrates an example arrangement of micro-emitters and non-active areas forming a multiple-beam-source VCSEL laser, according to an example embodiment.

FIGS. 30-34 illustrate embodiments that include a VCSEL configured to generate an array (1D or 2D) of multiple discrete laser beams for creating an array (1D or 2D) of multiple spaced-apart treatment spots 62 on the skin, e.g., to provide a fractional treatment. FIG. 30 illustrates an emitter surface view of an example VCSEL 14D in which micro-emitters 86 are arranged in an array (in this example, a 3×3 two-dimensional array) of discrete micro-emitter zones 88, each including a number of micro-emitters 86. Each micro-emitter zone 88 acts as a single beam source to provide a single discrete beam 60 for delivery to the skin. In particular, the micro-beams emitted by the micro-emitters 86 in each particular zone 88 combine (due to the divergence of the individual micro-beams) to form a single, discrete beam 60. Thus, the 3×3 array of discrete spaced-apart micro-emitter zones 88 forms a 3×3 array of discrete beam sources that generate a 3×3 array of discrete spaced-apart beams 60, which provide a corresponding 3×3 array of discrete spaced-apart treatment spots 62 on the skin, e.g., for providing a fractional treatment.

The micro-emitter zones 88 may be separated from each by non-active regions of the VCSEL chip, which regions may be formed by known photolithographic techniques. Each micro-emitter zone 88 may have any shape and size, and may include any number of micro-emitters 86 arranged in any suitable pattern to form any suitable one-dimensional or two-dimensional array of micro-emitters 86. For example, in some embodiments in which VCSEL is configured for pulsed radiation, each zone 88 may be shaped to provide a desired treatment spot size and/or shape, taking into consideration an assumed rate of movement of the device 10 across the skin during the pulsed radiation. Thus, for instance, to provide treatment spots 62 having a generally symmetrical shape (e.g., generally circular or square), each zone 88 may be elongated in the direction perpendicular to the expected glide direction of the device 10, with the aspect ratio of such elongation being selected based on an expected glide speed or range of glide speeds of the device 10. The zones may also be created by masking certain regions, such as by overlaying an opaque material, or by using optics, such as microlens array, or any other suitable means. As with uniform VCSELs, optics may be monolithic to the VCSEL and built with coatings, such as spun-on-glass, or MEMs, or other means.

Further, as discussed above regarding the single-beam-source VCSEL, the micro-emitters 86 in an array 84 may be evenly spaced from each other, e.g., to provide a beam 60 having a generally uniform intensity profile, or may be unevenly spaced from each other, e.g., to provide a beam 60 having a selected non-uniform intensity profile suitable for a particular application or treatment.

In addition, VCSEL 14D may include any suitable number of micro-emitter zones 88 arranged in any suitable pattern to form any suitable one-dimensional or two-dimensional array of zones 88. Zones 88 may evenly spaced from each other, e.g., to provide a generally uniform array of beams 60, or may be unevenly spaced from each other, e.g., to provide a non-uniform array of beams 60 for a particular application or treatment.

Figure 31:
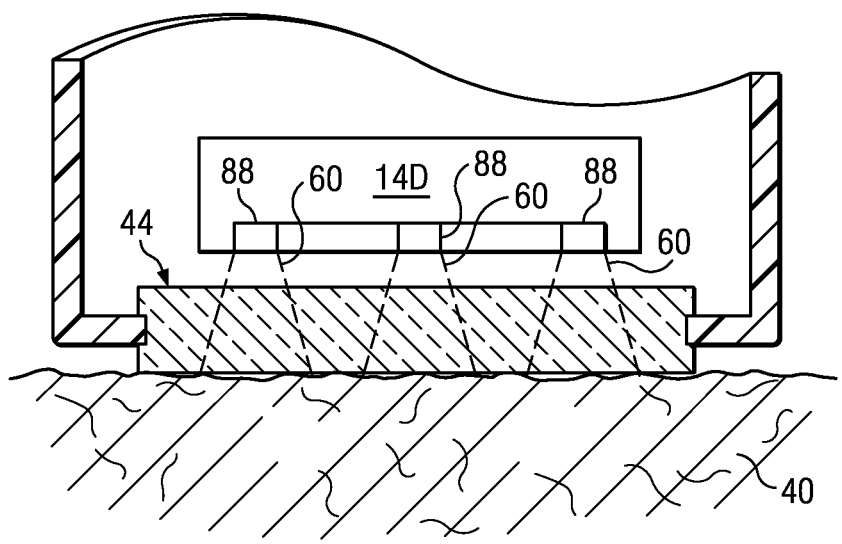
FIG. 31 illustrates an example direct exposure configuration of a device including a multiple-beam-source VCSEL laser as the radiation source, according to certain embodiments.

FIG. 31 a simplified cross-sectional side view of an example embodiment of device 10 that includes the example multi-beam-source VCSEL 14D of FIG. 30. In particular, the figure shows one row of the 3×3 array of micro-emitter zones 88, which row generates three discrete, spaced-apart beams 60 for delivery to the skin.

Figure 32:
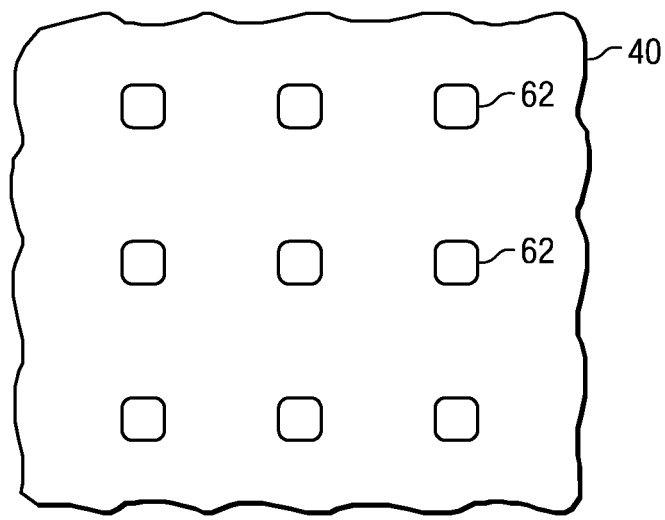
FIG. 32 illustrates an example treatment spot array produced by an example multiple-beam-source VCSEL laser having a two-dimensional array of emitter zones, according to certain embodiments.
Figure 33:
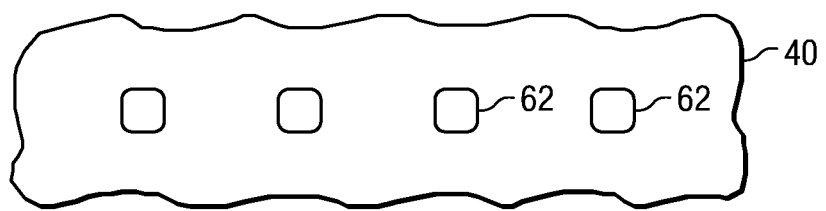
FIG. 33 illustrates an example treatment spot array produced by an example multiple-beam-source VCSEL laser having a one-dimensional array of emitter zones, according to certain embodiments.

FIG. 32 illustrates an example array of treatment spots 62 generated by the example VCSEL 14D shown in FIG. 30, e.g., as arranged in a device 10 as shown in FIG. 31. FIG. 33 illustrates an example one-dimensional array of treatment spots 62 generated by another example VCSEL having a one-dimensional array of (in this example, four) micro-emitter zones 88. As discussed above, VCSEL 14D may be configured to provide any other suitable one-dimensional or two-dimensional array of treatment spots 62 by designing micro-emitter zones 88 as desired.

Figure 34:
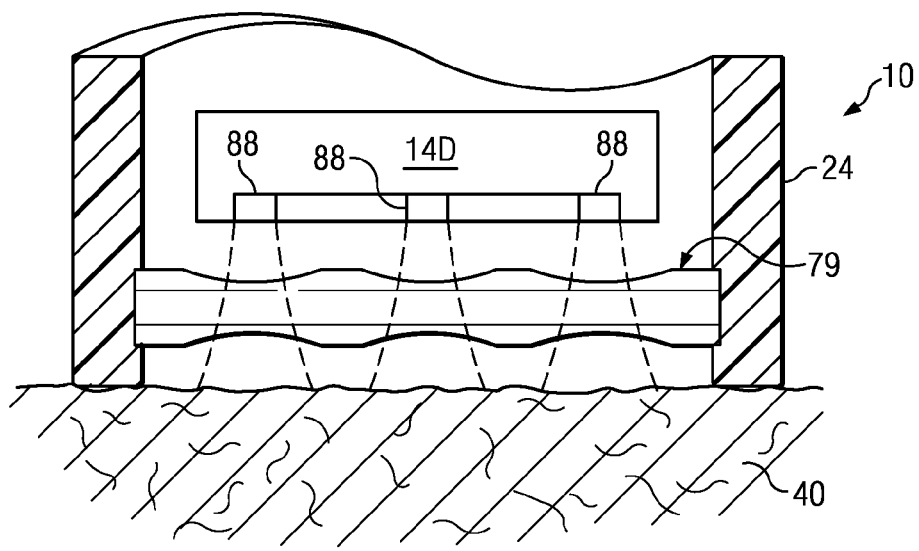
FIG. 34 illustrates an example indirect exposure arrangement of a multiple-beam-source VCSEL laser and downstream optic (concave lens array), according to certain embodiments.

FIG. 34 a simplified cross-sectional side view of an example embodiment of device 10 that includes a multi-beam-source VCSEL 14D (e.g., the VCSEL shown in FIG. 30), with a micro-lens array 79 for affecting each beam 60 generated by the various micro-emitter zones 88. Micro-lens array 79 may include an array of optical elements corresponding to the array of micro-emitter zones 88 of the particular VCSEL 14D, with each optical element of the array corresponding to one zone 88 of VCSEL 14D (and thus one beam 60). The optical elements of the micro-lens array 79 may be discrete elements or may be formed as a contiguous structure, e.g., as shown in FIG. 34. Each optical element of the array 79 may comprise any type of lens (e.g., concave, convex, ball lens, cylindrical lens, aspherical lens, etc.) or other optic for affecting the corresponding beam 60 as desired. For example, each optical element of array 79 may be provided to increase or decrease the divergence of the resulting beam 60 delivered to the skin, such as to provide a desired spot size or shape, energy intensity level at the skin, and/or to provide increased eye safety.

In some embodiments, each micro-emitter zone 88 of a multi-beam-source VCSEL may be independently addressable or controllable, e.g., by independently controlling the current applied to each micro-emitter zone 88. For example, zones 88 may be independently turned on/off or pulsed, or activated at different power levels. For pulsed embodiments, the various pulsing parameters for each zone 88, e.g., pulse on time, pulse off time, pulse frequency, pulse duration, pulse profile, intensity, power level, etc., may be controlled independent of the other zones 88. Thus, for instance, the multiple zones 88 may be controlled to deliver pulsed beams 60 (and create corresponding treatment spots 62) in any spatial or sequential order, e.g., according to a defined algorithm, semi-randomly, or randomly.

In some embodiments, device 10 may include a single VCSEL for providing one or multiple beams 60, as discussed above. In other embodiments, device 10 may include multiple VCSELs, each providing one or multiple beams 60. Multiple VCSELs may be arranged in any suitable manner in device 10, e.g., in any suitable one-dimensional or two-dimensional array.

In some embodiments of device 10, VCSEL(s) may be configured for "direct exposure" radiation, "close proximity" radiation, or both, as such terms are defined and discussed herein. Further, VCSEL(s) may be arranged in any of the various configurations discussed herein regarding other types of radiation sources, e.g., VCSEL(s) may be arranged in any of the various configurations shown in FIGS. 10-16 with respect to embodiments including edge emitting laser diodes or configured with sensors, such as displacement, velocity, or contact, or configured for eye safety, such as Class 1M or better per IEC 60825, and other features disclosed herein. Some embodiments that use VCSEL(s) as radiation source(s) may include a diffuser or other element(s) or configuration to increase the eye safety aspects of such devices, e.g., depending on the beam divergence of the particular VCSELs, the configuration of micro-emitters 86 and emitter zones 88, and/or one or more operational parameters of device 10, e.g., pulse parameters, output fluence, etc.

Like edge emitting laser diodes 14A and laser diode bars 14B/14C discussed above, VCSELs 14D may be controlled to deliver pulsed radiation, continuous wave (CW) radiation, or otherwise. Thus, embodiments of device 10 including one or more VCSELs can generate one- or two-dimensional arrays of treatment spots 62 by manually scanning a series of beams 30 onto the skin, e.g., by pulsing the VCSEL(s), or the individual micro-emitter zones 88 of the VCSEL(s) while device 10 is moved across the skin, e.g., in a gliding mode or stamping mode operation. The device 10 may be glided across the skin any suitable number of times and in any suitable direction(s) to cover a desired treatment area.

Eye Safety

Some embodiments of device 10 provide eye safe radiation, by delivering a substantially divergent energy beam 60 (e.g., using an edge emitting laser diode with no downstream optics), and/or using an eye safety control system including one or more sensors 26, and/or by any other suitable manner. For example, in some laser-based embodiments or settings (including certain direct exposure embodiments and certain direct exposure embodiments), device 10 meets the Class 1M or better (such as Class 1) eye safety classification per the IEC 60825-1, referred to herein as "Level 1 eye safety" for convenience. In other laser-based embodiments or settings (including certain direct exposure embodiments and certain direct exposure embodiments), the device falls outside the IEC 60825-1 Class 1M eye safety classification by less than 25% of the difference to the next classification threshold, referred to herein as "Level 2 eye safety" for convenience. In still other laser-based embodiments or settings (including certain direct exposure embodiments and certain direct exposure embodiments), the device falls outside the IEC 60825-1 Class 1M eye safety classification by less than 50% of the difference to the next classification threshold, referred to herein as "Level 3 eye safety" for convenience. In some lamp-based embodiments, the device meets the "Exempt" or "Low Risk" eye safety classification per the IEC 62471.

Some laser-based embodiments of device 10 configured for direct exposure (and/or close proximity exposure) of laser radiation provide Level 3 eye safety as defined above; some laser-based direct exposure embodiments provide Level 2 eye safety as defined above; and some laser-based direct exposure embodiments provide Level 1 eye safety as defined above. Some laser-based embodiments of device 10 configured for indirect exposure (and/or close proximity exposure) of laser radiation provide Level 3 eye safety as defined above; some laser-based direct exposure embodiments provide Level 2 eye safety as defined above; and some laser-based direct exposure embodiments provide Level 1 eye safety as defined above.

Such levels of eye safety may be provided based on a combination of factors, including for example, (a) the divergence of the beam, (b) the pulse duration, (c) the emitted power, (d) the total energy per pulse, (e) the wavelength of the emitted beam, and/or (f) the arrangement of the laser beam source. Thus, in some embodiments (including certain direct exposure, close proximity embodiments; certain direct exposure, remote proximity embodiments; certain indirect exposure, close proximity embodiments; and certain indirect exposure, remote proximity embodiments), one, some, or all of such factors may be selected or adjusted to provide Level 1, Level 2, or Level 3 eye safety, as defined above.

Certain beam sources discussed herein generate divergent (and in some cases, highly divergent) radiation in at least one axis, which may increase the eye safety aspect of embodiments that employ such beam sources. For example, a typical edge emitting laser diode diverges in both a fast axis and a slow axis, which may to provide Level 1, Level 2, or Level 3 eye safety, depending on the other selected parameters. An analysis of relevant issues is discussed below.

Highly divergent intense light source can be eye safe if it meets the IEC 60825-1 Class 1M AEL (Accessible Emission Limit) specification. With Class 1M classification, the source is generally only potentially harmful if an intervening optics is deliberately placed in between the source and the eye. For the typical wavelength greater than 1400 nm used in fractional laser treatment, the light source is also greatly attenuated by the water absorption in the eye anterior chamber. Hence there is substantially little or no retinal hazard in this wavelength range. The emission limit is determined by the potential corneal damage. The accessible emission limit for Class 1M source in the wavelength range of 1400 to 1500 nm and 1800 to 2600 nm is described by a simple equation in Table 4 of IEC 60825-1:2007:

$$AEL = 4.4 t^{0.25} \text{ mJ} \qquad \text{Equation 1}$$

AEL energy is measured at 70 mm from the source with a circular aperture of 7 mm in diameter (Condition 2 measurement setup described in Table 11 of IEC 60825-1:2007, applicable for diverging beam). In this equation, t (in unit of seconds) is the source pulse duration in the range of 1 ms to 350 ms. For a typical single beam laser diode source, this pulse duration is in the range of 1 to 10 ms. Therefore, the corresponding AEL is 0.8 to 1.4 mJ.

The actual source AE (Accessible Energy) can be estimated for a given beam divergent characteristics. It can also be measured experimentally with the appropriate aperture stop (7-mm wide) and measurement distance (70-mm from the source). The AE at a distance 70-mm from the treatment aperture is given by (this is approximately correct for a Gaussian beam from a diffraction limited laser):

$$AE = 2.5 \times 10^{-3} Q / [\tan(\Phi_F/2)\tan(\Phi_S/2)] \text{ mJ} \qquad \text{Equation 2}$$

where Q (in unit of mJ) is the source energy at the treatment plane, and $\Phi_F$ and $\Phi_S$ are the beam divergence in the fast and slow axis, respectively. To achieve the Class 1M eye safety classification, AE must be lower than the AEL for the corresponding pulse duration.

Table 6 below provides several example configurations and device settings for providing Level 1 eye safety (Class 1M or better per standard IEC 60825-1) for certain embodiments of device 10.

pulse durations, wavelengths, pulse repetition frequencies, beam profile characteristics, and beam propagation characteristics) to provide increased eye safety. Other embodiments may provide a particular eye safety level (e.g., Level 1, Level 2, or Level 3 as defined above) without such elements, and in a direct exposure configuration (and/or close proximity configuration), due to the inherent or selected divergence of the beam source (e.g., certain laser diodes) combined with suitable operational parameters of the beam source, e.g., as discussed above.

Displacement-Based Control

As discussed above regarding FIG. 1, device 10 may include control systems 18 configured to control various controllable operational parameters of device 10 (e.g., operational aspects of radiation engine 12, fans 34, displays 32, etc.). In some embodiments, control systems 18 may include a displacement monitoring and control system 132 ("displacement-based control system 132" for short) configured to determine the displacement of device 10 relative to the skin if

TABLE 6

| Parameter | Example Embodiment 1 | Specific Example of Embodiment 1 | Example Embodiment 2 | Specific Example of Embodiment 2 |
| --- | --- | --- | --- | --- |
| Configuration | direct exposure (no optics) | direct exposure (no optics) | indirect exposure (with optic) | indirect exposure (with optic) |
| Radiation source | Single beam edge emitting laser diode | Single beam edge emitting laser diode | Single beam edge emitting laser diode w/collimating optics | Single beam edge emitting laser diode w/ collimating optics |
| wavelength | 1400-1500 nm or 1800-2600 nm | 1400-1500 nm or 1800-2600 nm | 1400-1500 nm or 1800-2600 nm | 1400-1500 nm or 1800-2600 nm |
| beam divergence at skin surface (fast axis, slow axis) | 35°-45° fast axis, 6°-12° slow axis | 45° fast axis 10° slow axis | 2°-12° fast axis, 6°-12° slow axis | 12° fast axis 12° slow axis |
| Pulse duration (ms) | 1-8 | about 3 | 1-15 | about 5 |
| Power (W) | 2-6 | about 4 | 1-4 | about 1 |
| Total energy per pulse (mJ) | 5-15 | about 12 | 5-15 | about 5 |
| AEL (mJ) | 0.8-1.3 | about 1.0 | 0.8-1.5 | about 1.2 |
| AE (mJ) | 0.3-2.3 | about 0.8 | 1.1-41 | about 1.1 |
| Eye safety classification | Class 1M for AE < AEL | Class 1M | Class 1M for AE < AEL | Class 1M |

Because certain embodiments or device settings may provide Level 1, Level 2, or Level 3 eye safety based on the appropriate selection of parameters discussed above, in some such embodiments an eye safety sensor or system may be omitted. However, some such embodiments, even those providing Level 1 eye safety, may include an eye safety sensor or system to provide redundancy, to meet particular regulatory standards, or for other reasons.

In at least some embodiments additional eye safety is provided by incorporating a contact sensor that enables pulsing of the light source only when in contact with the skin. Thus, in such embodiments, the likelihood of corneal eye injury may be reduced or substantially eliminated unless the device is literally pressed to the eye surface.

Some embodiments may include an optical diffuser or radiation-diffusing elements or configuration (e.g., as described in U.S. Pat. No. 7,250,045, U.S. Pat. No. 7,452,356, or US Patent Application Publication, all three of which are hereby incorporated by reference), one or more optics (e.g., a lens), or other elements and configurations (e.g., selected or as device 10 is moved across the surface of the skin (e.g., while operating device 10 in a gliding mode or a stamping mode), and control one or more controllable operational parameters of device 10 based on the determined displacement. For example, displacement-based control system 132 may control one or more operational aspects of radiation source(s) 14, such as for example, controlling the radiation mode of radiation source(s) 14, controlling the on/off status of radiation source(s) 14, controlling the timing of such on/off status (e.g., pulse-on time, pulse-off time, pulse duty cycle, pulse frequency), controlling parameters of the radiation (e.g., wavelength, intensity, power, fluence, etc.), controlling parameters of optics 16, and/or any other controllable operational parameters of device 10.

In some embodiments, displacement-based control system 132 may also provide feedback to the user via display 32 and/or one or more user interfaces 28 based on the monitored displacement of device 10 and/or the automatic control of one or more controllable operational parameters by system 132. For example, system 132 may provide audio and/or visual feedback to the user indicating data detected, or actions taken, by system 132, e.g., feedback indicating whether or not the displacement of device 10 exceeds a predetermined threshold distance, feedback indicating that treatment radiation source 14 has been turned on or off, feedback indicating that system 132 has automatically changed the radiation mode or other parameter of treatment radiation source 14, etc.

Displacement-based control system 132 may include, utilize, or otherwise cooperate with or communicate with any one or more of the control subsystems 52 discussed above with respect to FIG. 2 (e.g., radiation source control system 130, and user interface control system 134, including user interface sensor control subsystem 140 and user input/feedback control subsystem 142), as well as control electronics 30, any one or more sensors 46, user interfaces 28, and displays 32.

Figure 35:
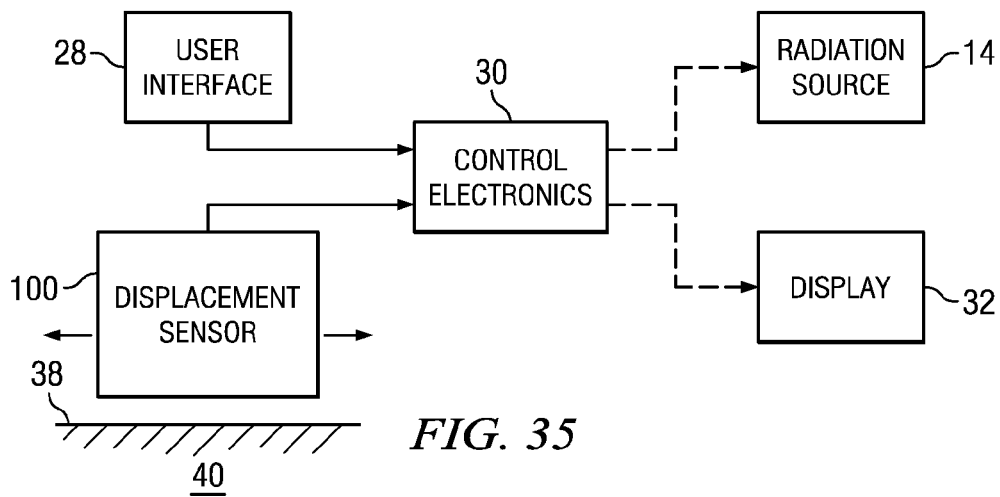
FIG. 35 illustrates a block diagram of an example displacement-based control system, according to certain embodiments.

FIG. 35 illustrates a block diagram of a displacement-based control system 132, according to certain embodiments. Displacement-based control system 132 may be provided in any of the embodiments of device 10 discussed herein. As shown, displacement-based control system 132 may include a displacement sensor 100, control electronics 30, and treatment radiation source 14 and/or display 32. In general, displacement sensor 100 collects data regarding the displacement of device 10 relative to the skin 40 and communicates such data to control electronics 30, which analyzes the data and controls or provides feedback via one or more of treatment radiation source 14 and display 32. In some embodiments, control electronics 30 may also analyze particular user input received via one or more user interfaces 28 in conjunction with data received from sensor 100. For example, the appropriate control or feedback provided by control electronics 30 (e.g., as defined by a relevant algorithm 154) may depend on the current operational mode and/or other settings selected by the user. For instance, the minimum threshold displacement for triggering particular responses by control electronics 30 may depend on the current operational mode selected by the user.

Control electronics 30 may include any suitable logic instructions or algorithms 154 stored in memory 152 and executable by one or more processors 150 (e.g., as discussed above regarding FIG. 1) for performing the various functions of displacement-based control system 132. Displacement sensor 100 may be configured for detecting, measuring, and/or calculating the displacement of device 10 relative to the skin 40, or for generating and communicating signals to control electronics 30 for determining the displacement of device 10. In some embodiments, e.g., as discussed below with reference to FIGS. 40-43, displacement sensor 100 may be a single-pixel sensor configured to identify and count intrinsic skin features in the skin, and determine a displacement of the device 10 across the skin based on the number of identified intrinsic skin features. As used herein, "intrinsic skin features" include both (a) surface features of the skin, e.g., textural roughness, follicles, and wrinkles, and (b) sub-surface features, e.g., vascularity and pigmentation features.

In other embodiments, e.g., as discussed below with reference to FIG. 45, displacement sensor 100 may be a multiple-pixel sensor, such as a mouse-type optical sensor utilizing a two-dimensional array of pixels.

Depending on the particular embodiment, displacement sensor 100 (or a combination of multiple displacement sensors 100) may be used for (i) detecting, measuring, and/or calculating displacements of device 10 in one or more directions, or (ii) detecting, measuring, and/or calculating the degree of rotation travelled by device 10 in one or more rotational directions, or (iii) any combination thereof.

Displacement-based control system 132, and in particular control electronics 30, may control one or more controllable operational parameters of device 10 (e.g., operational aspects of treatment radiation source 14, fans 34, displays 32, etc.) to achieve any of a variety of goals. For example, control electronics 30 may control treatment radiation source 14 (a) in order to avoid overtreatment of the same area of skin, (b) to provide desired spacing between adjacent or sequential treatment spots 62 or arrays of spots 62, (c) to generate a relatively uniform pattern, or other desired pattern, of treatment spots 62, (d) to restrict the delivery of radiation to particular tissue, such as human skin (i.e., to avoid delivering radiation to eye or to other non-skin surfaces), (e) and/or for any other suitable goals, and (f) and combination of the above.

In some embodiments, displacement-based control system 132 may be used in both a gliding mode and a stamping mode of device 10.

Figure 36:
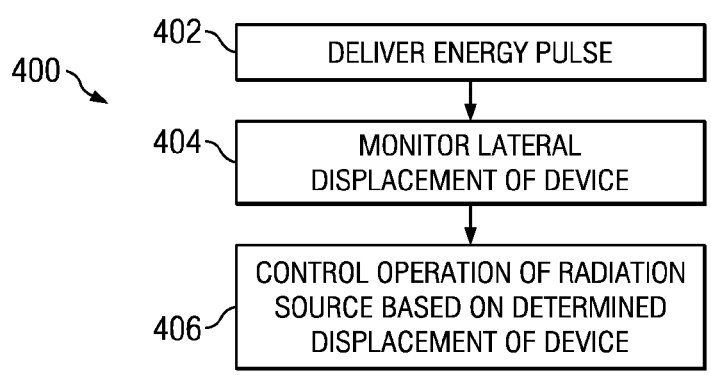
FIG. 36 illustrates a flowchart of an example method for controlling a device using a displacement-based control system, while the device is used either in a gliding mode or a stamping mode, according to certain embodiments.

FIG. 36 illustrates a flowchart of an example method 400 for controlling device 10 using displacement-based control system 132, while device 10 is used either in a gliding mode or a stamping mode, according to certain embodiments. At step 402, device 10 pulses the beam source(s) of device 10, to generate one or more treatment spots 62 on treatment area 40. If device 10 is being used in a gliding mode, the user may glide device 10 across the skin during the first pulse of the beam source(s). If device 10 is being used in a stamping mode, the user may hold device 10 stationary on the skin during the first pulse of the beam source(s).

At step 404, displacement-based control system 132 performs a first monitoring process to monitor and analyze the displacement of device 10 across the surface of the skin using displacement sensor 100. For example, as discussed below, displacement-based control system 132 may analyze signal 360 to identify and count intrinsic skin features 70 in the skin (e.g., in embodiments utilizing a single-pixel displacement sensor 100 (e.g., sensors 100A, 100B, or 100C discussed below)), or compare images scanned at different times (in embodiments utilizing a multi-pixel displacement sensor 100 (e.g., sensor 100D discussed below)), as device 10 is moved across the skin (e.g., in a gliding mode, during and/or after the first pulse of the beam source(s); or in a stamping mode, after the first pulse of the beam source(s)). System 132 may begin the first monitoring process at the initiation or conclusion of the first pulse of the beam source(s) or upon any other predefined event or at any predetermined time.

At step 406, displacement-based control system 132 controls the pulsing of the beam source(s) based on the displacement of device 10 determined at step 404. For example, in some embodiments, displacement-based control system 132 initiates a second pulse of the beam source(s) upon determining that device 10 has moved a particular predetermined distance across the skin (e.g., 3 mm). Thus, in such embodiments, a substantially constant spacing (e.g., 3 mm) between successive treatment spots 62 in the glide direction can be achieved regardless of the manual glide speed. Thus, the pulse frequency may vary dynamically as a function of the manual glide speed.

In other embodiments, device 10 (or the user) sets a defined pulse frequency (e.g., 15 Hz), as well as a predefined minimum device displacement for providing a predefined minimum spacing between successive treatment spots 62 in the glide direction (e.g., 1 mm). Displacement-based control system 132 analyzes the monitored displacement of device 10 determined at step 404 and the defined pulse frequency to determine whether the providing the next pulse according to the defined pulse frequency would violate the minimum spot spacing (e.g., 1 mm) If not, displacement-based control system 132 allows device 10 to continue pulsing at the defined pulse frequency. However, if so (i.e., if providing the next pulse according to the defined pulse frequency would violate the minimum spot spacing), displacement-based control system 132 may control radiation source 14 to delay the next pulse at least until system 132 determines that the minimum device displacement has been achieved (thus ensuring the predefined minimum spacing between successive treatment spots 62), or system 132 may other control radiation source 14 to prevent over-treatment (e.g., decreasing the beam intensity, turning off radiation source 14, providing feedback to the user, etc.)

Single Pixel Displacement Sensor

Figure 37:
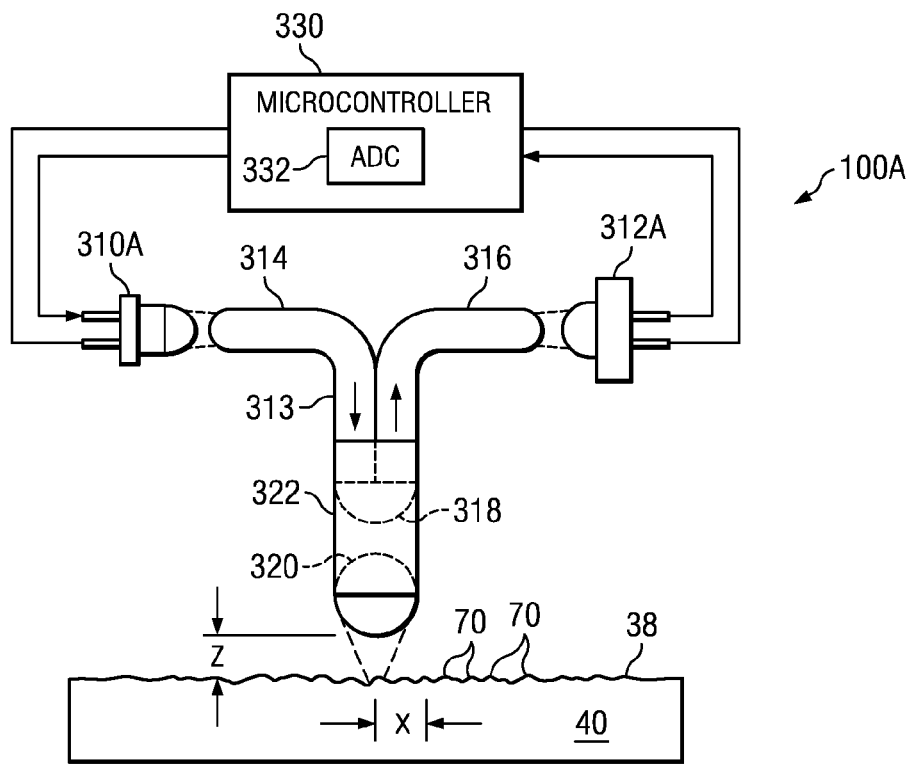
FIG. 37 illustrates an example single-pixel displacement sensor for use in a displacement-based control system, according to certain embodiments.

FIG. 37 illustrates an example single-pixel displacement sensor 100A for use in displacement-based control system 132, according to certain embodiments. Displacement sensor 100A includes a light source 310A, a light detector 312A, a light guide 313 having an input and output portions 314 and 316, a half-ball lens 318, a ball lens 320, a housing 322 for housing at least lenses 318 and 320 (and/or other components of sensor 100A), and a and a microcontroller 330.

Light source 310A may be a light-emitting diode (LED) or any other suitable light source. Light source 310A may be selected for detecting fine details in the surface or volume of human skin. Thus, a wavelength may be selected that penetrates a relatively shallow depth into the skin before being reflected. For example, light source 310A may be a blue LED having a wavelength of about 560 nm, or a red LED having a wavelength of about 660 nm, or an infrared LED having a wavelength of about 940 nm. Red or infrared wavelength LEDs are relatively inexpensive and work well in practice. Alternatively, a semiconductor laser or other light source could be used.

Light detector 312A may be a photodiode, phototransistor, or other light detector. In some embodiments, a phototransistor has sufficient current gain to provide a directly usable signal, without requiring additional amplification.

Light guide 313 is configured to guide light from light source 310A (via input portion 314) and guide light reflected off the skin to detector 312A (via output portion 316). Input portion 314 and output portion 316 may comprises optical fibers or any other suitable light guides. Light guide 313 may be omitted in some embodiments in which light source 310A and detector 312A are close enough to the skin surface to image or convey the light directly onto the skin surface, or alternatively using suitable optics to image or convey light source 310A and detector 312A directly onto the skin surface.

Microcontroller 330 may be configured to drive light source 310A and receive and analyze signals from light detector 312A. Microcontroller 330 may include an analog-to-digital converter (ADC) 332 for converting and processing analog signals from light detector 312A.

In operation of this embodiment, light (for example, visible or near-IR energy) from light source 310A travels down input light guide 314 and through half-ball lens 318 and ball lens 320, which focuses the light on the skin surface 32. Some of this light is reflected and/or remitted by the skin and returns through ball lens 320, half-ball lens 318, and output light guide 316, toward light detector 312A, which converts the light into an electrical signal, which is then delivered to microcontroller 330. The light may be modulated to permit discrimination of a constant background ambient illumination level from the local light source.

Detector 312A may deliver analog signals to microcontroller 330, which may convert the signals to digital signals (using integrated ADC 332 or suitable alternatives), and perform computations regarding on the amplitude of the recorded signal over time to identify and count features in the skin and determine a relative displacement device 10 accordingly, as discussed below.

The amount of light that is returned to detector 312A is a strong function of the distance "z" between the sensor optics and skin surface 32. With no surface present only a very small signal is generated, which is caused by incidental scattered light from the optical surfaces. In addition to displacement sensor, this characteristic can be exploited to provide a contact sensor in another embodiment. When the skin surface 32 is within the focal distance of the lens 320, a much larger signal is detected. The signal amplitude is a function of distance z as well as surface reflectivity/remittance. Thus, surface texture features on the skin surface create a corresponding signal variation at detector 312A. Microcontroller 330 is programmed to analyze this signal and identify intrinsic skin features 70 that meet particular criteria. Microcontroller 330 may count identified features and determine an estimated displacement of sensor 100A relative to the skin 40 in the x-direction (i.e., lateral displacement), based on knowledge of estimated or average distances between intrinsic skin features 70 for people in general or for a particular group or demographic of people, as discussed below.

Displacement sensor 100A as described above may be referred to as a "single-pixel" displacement sensor 100A because it employs only a single reflected/remitted beam of light for generating a single signal 360, i.e., a single pixel. In other embodiments, displacement sensor 100 may be a multi-pixel sensor that employs two pixels (i.e., two reflected beams of light for generating two signals 360), three pixels, four pixels, or more. Multi-pixel displacement sensors 100 may be configured such that the multiple pixels are arranged along a single linear direction (e.g., along the glide direction, the scan direction, or any other direction), or in any suitable two-dimensional array (e.g., a circular, rectangular, hexagonal, or triangular pattern).

Figure 38:
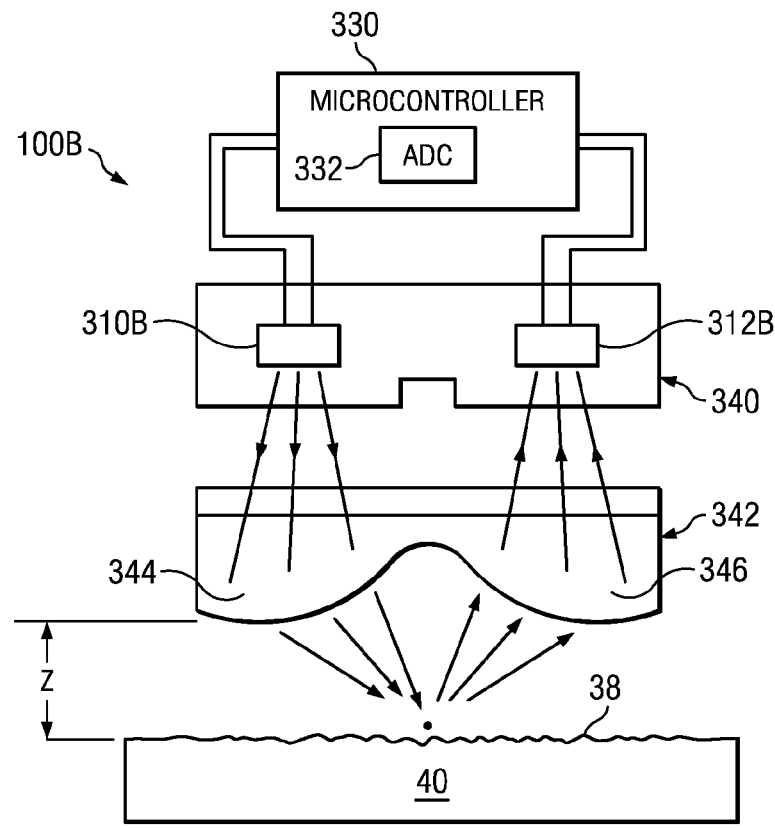
FIG. 38 illustrates another example single-pixel displacement sensor for use in a displacement-based control system, according to certain embodiments.

FIG. 38 illustrates another example single-pixel displacement sensor 100B for use in displacement-based control system 132, according to certain embodiments. Displacement sensor 100B includes a light source 310B, a light detector 312B, optics 342, and a microcontroller 330.

Light source 310B and light detector 312B may be provided in an integrated emitter-detector package 340, e.g., an off-the-shelf sensor provided by Sharp Microelectronics, e.g., the Sharp GP2S60 Compact Reflective Photointerrupter. Light source 310B may be similar to light source 310A discussed above, e.g., a light-emitting diode (LED) or any other suitable light source. Light detector 312B may be similar to light source 310A discussed above, e.g., a photodiode, phototransistor, or other light detector.

Optics 342 may include one or more optical elements for directing light from light source 310B onto the target surface and for directing light reflected/remitted from the target surface toward light detector 312B. In some embodiments, optics 342 comprises a single lens element 342 including a source light focusing portion 344 and a reflected light focusing portion 346. As shown, source light focusing portion 344 may direct and focus light from light source 310B onto the skin surface 38, and reflected light focusing portion 346 may direct and focus reflected light onto detector 312B. Lens element 342 may have any suitable shape for directing and focusing the source light and reflected light as desired.

Microcontroller 330 may be configured to drive light source 310B and receive and analyze signals from light detector 312B. Microcontroller 330 may include an analog-to-digital converter (ADC) 332 for converting and processing analog signals from light detector 312B.

The operation of sensor 100B—including the operation of light detector 312B and microcontroller 330—may be similar to that described above with reference to sensor 100A of FIG. 37. That is, detector 312B may record a signal having an amplitude or other property that corresponds to a distance z perpendicular to the target surface or other properties indicative of intrinsic skin features. Detector 312B may deliver analog signals to microcontroller 330, which may convert the signals to digital signals (using integrated ADC 332), and perform computations regarding the recorded signal over time to identify and count features in the skin and determine a relative displacement of device 10 accordingly.

Like displacement sensor 100A, displacement sensor 100B may be referred to as a "single-pixel" displacement sensor 100B because it employs only a single reflected beam of light for generating a single signal 360, i.e., a single pixel.

Figure 39:
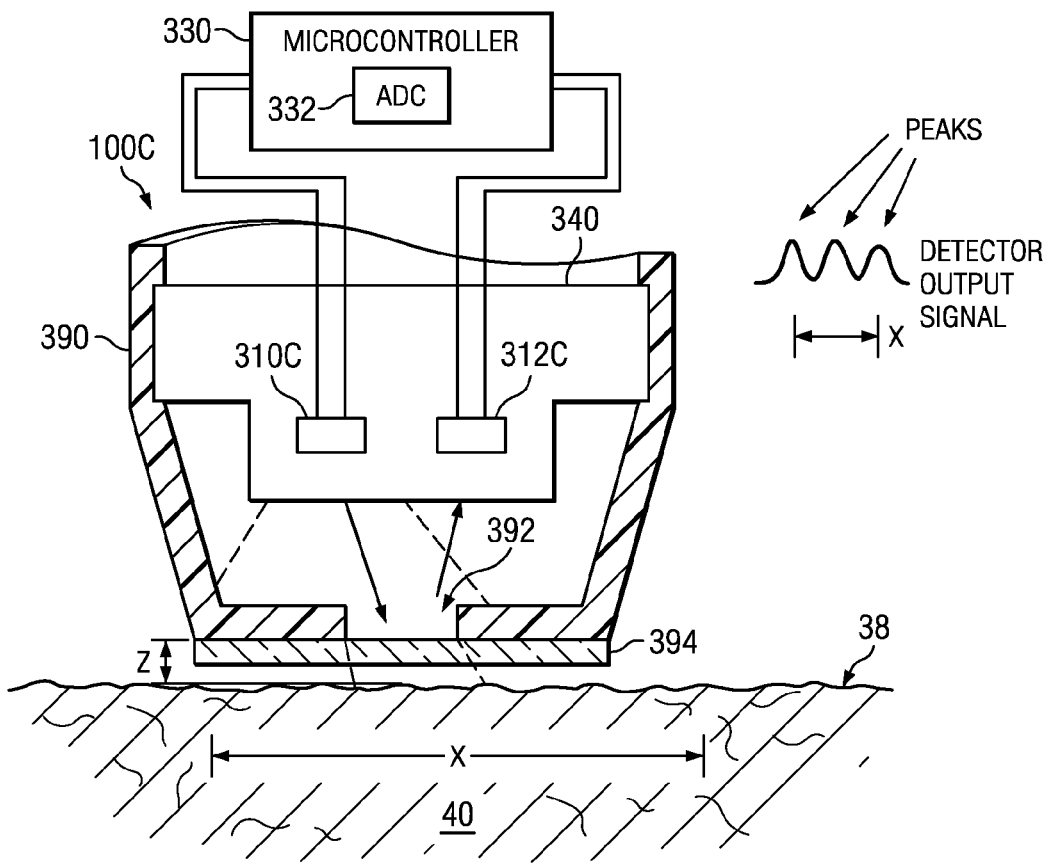
FIG. 39 illustrates yet another example single-pixel displacement sensor for use in a displacement-based control system, according to certain embodiments.

FIG. 39 illustrates yet another example single-pixel displacement sensor 100C for use in displacement-based control system 132, according to certain embodiments. Displacement sensor 100C is generally similar to displacement sensor 100B shown in FIG. 38, but omits the lens element 342 of displacement sensor 100B.

Displacement sensor 100C includes a light source 310C, a light detector 312C, optics 342, and a microcontroller 330. Light source 310C and light detector 312C may be provided in an integrated emitter-detector package 340, e.g., an off-the-shelf sensor provided by Sharp Microelectronics, e.g., the Sharp GP2S60 Compact Reflective Photointerrupter. Light source 310C may be similar to light source 310A/310B discussed above, e.g., a light-emitting diode (LED) or any other suitable light source. Microcontroller 330 may be configured to drive light source 310C with a direct or modulated current. Light detector 312C may be similar to light source 310A discussed above, e.g., a photodiode, phototransistor, or other light detector.

The integrated (or non-integrated) emitter-detector package 340 may be housed in an opaque enclosure 390, having a clear aperture 392 in the front which is covered by a window 394 (for example a transparent plastic, or glass) Infrared light from light source 310C (e.g., LED) shines through the aperture 392 and impinges on the skin surface 38. Some of this light (reflected/remitted from the skin 40, as well as scattered from the interior volume of opaque enclosure 390, returns through aperture 392 and reaches detector 312C (e.g., photodetector), which converts the received light into an electrical signal. The light may be modulated to permit discrimination of a constant background ambient illumination level from the local light source.

The amount of light that is returned to detector 312C is a strong function of the distance "z" between the skin surface 38 and the optical aperture 392. When the skin surface 38 is close to or in contact with window 394, a larger signal is detected. With no surface presented to the detector, a smaller optical signal remains, due to reflections from the surface of opaque mask 390 and window 394, as well as background light from exterior illumination sources.

Thus, the signal amplitude recorded by detector 312C is a function of z-height as well as skin reflectivity/remittance. Surface texture features 70 create a corresponding signal variation at detector 312C. Detector 312C may deliver the recorded analog signals (with the amplitude being at least indicative of z-height) to microcontroller 330, which may convert the signals to digital signals (using integrated ADC 332), and perform computations regarding the recorded signal over time to identify features 70 in the skin (based on the signal amplitude), count or otherwise process such identified features 70, and determine a relative displacement of device 10 accordingly.

Integrated emitter-detector pairs used for the proximity detector may be compact, inexpensive, and readily available. It is also possible to use a separate emitter and detector. Any suitable wavelength range of light may be used, but infrared may be selected due to the sensitivity of the detector 312C (e.g., phototransistor), and ability to block out visible light with an IR-pass filter over the detector. Also, different skin types show more uniform reflectance levels in IR than in shorter wavelengths. Test results show that a phototransistor has sufficient current gain to provide a directly usable signal to the integrated ADC 332 of microcontroller 330, without requiring additional amplification.

Like displacement sensors 100A and 100B, displacement sensor 100C may be referred to as a "single-pixel" displacement sensor 100C because it employs only a single reflected beam of light for generating a single signal, i.e., a single pixel.

Figure 40:
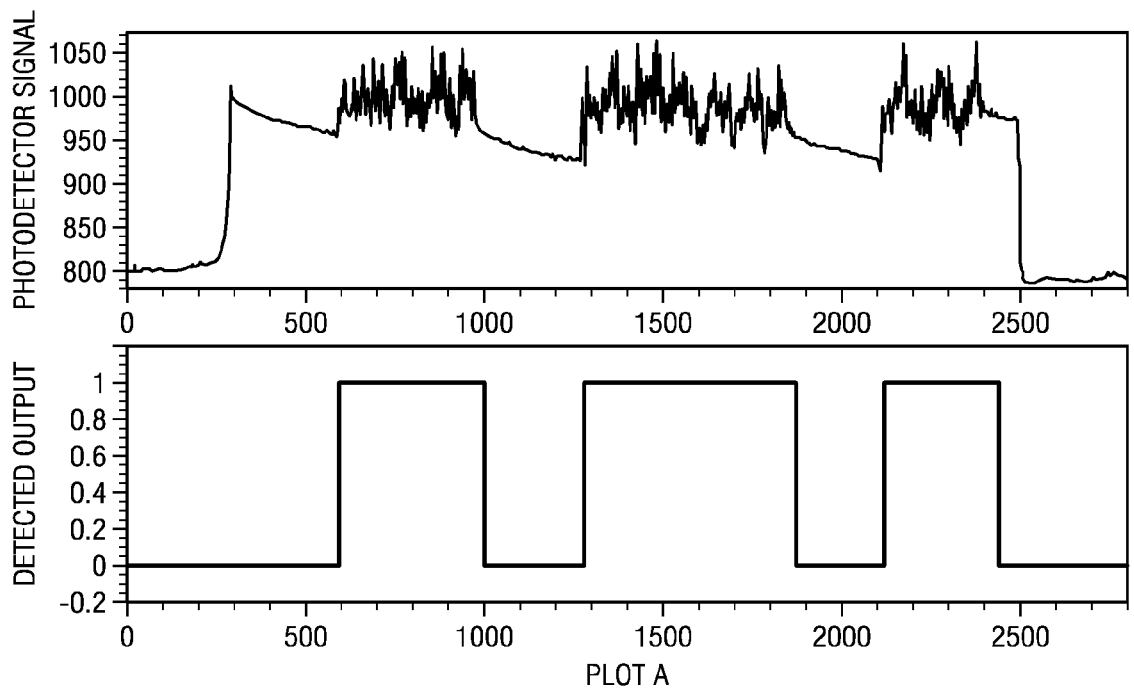
FIG. 40 illustrates a pair of experimental data plots for an embodiment of an optical displacement sensor being scanned above the skin surface of a human hand.

FIG. 40 illustrates a pair of experimental data plots for an embodiment of optical displacement sensor 100C being scanned above the skin surface 38 of a human hand. The photodetector signal (y-axis) is shown versus time (x-axis) in arbitrary units. The area without dense peaks indicates times in which the sensor aperture 392 is held against a fixed area of the skin. An algorithm takes as input the photodetector signal to generate the lower "detected output" plot, which is a signal suitable for controlling device 10. For example, microcontroller 330 may be programmed to analyze the photodetector signal and identify intrinsic skin features 70 that meet particular criteria, e.g., using any of the various techniques or algorithms disclosed herein, or any other suitable techniques or algorithms. In some embodiments, microcontroller 330 may count identified features and determine an estimated displacement of sensor 100C relative to the skin 40 in the x-direction (i.e., lateral displacement), based on knowledge of estimated or average distances between intrinsic skin features 70 for people in general or for a particular group or demographic of people, as discussed below.

Certain embodiments of single-pixel displacement sensor 100, e.g., sensors 100A, 100B, and/or 100C discussed above, may not require imaging optics, as compared to imaging-type sensors. Further, certain embodiments of single-pixel displacement sensor 100 may not require close proximity between the electronics (e.g., microcontroller) and the target surface to be sensed. For example, the light source and/or detector may be spaced away from the target surface, with light guides or relay optics used to convey light between the light source/detector and the target surface. As another example, the light source and/or detector may be spaced relative close to the target surface, but may be coupled to a relatively remote microcontroller by wiring.

Further, in certain embodiments of single-pixel displacement sensor 100, e.g., sensors 100A, 100B, and 100C discussed above, the active components (e.g., light source, detector, etc.) and the active sensing area are relatively small (e.g., as compared to a standard optical mouse-type imaging sensor). Thus, in embodiments in which single-pixel displacement sensor 100 is located at the application end 42 of device 10, sensor 100 may occupy relatively little real estate on the application end 42 (e.g., as compared to a standard optical mouse-type imaging sensor), which may allow the total size of application end 42 to be reduced in at least one dimension, which may be advantageous in certain embodiments.

Figure 41:
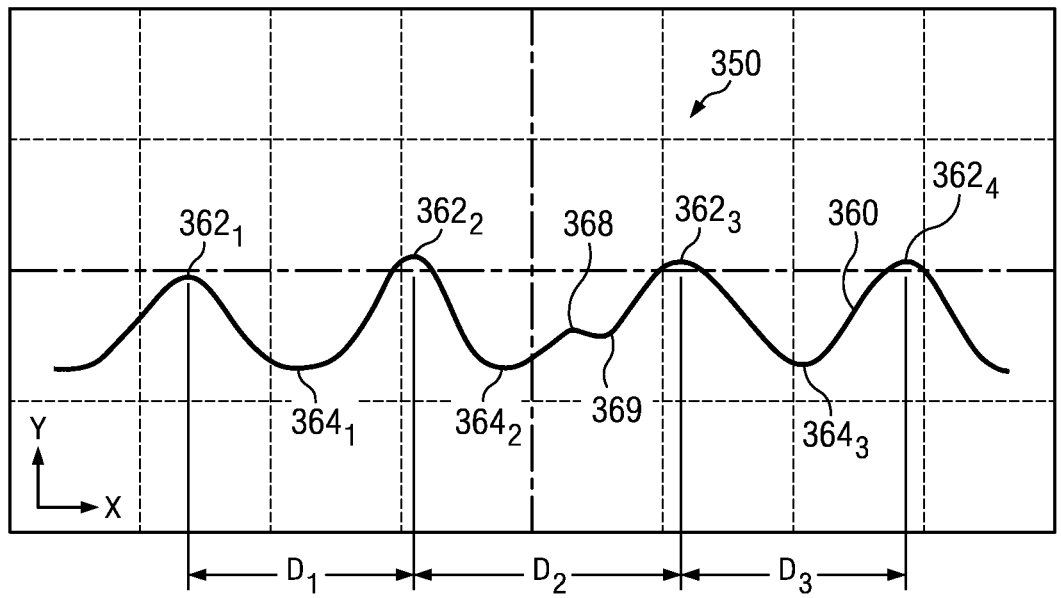
FIG. 41 represents an example plot of a signal generated by a detector as a displacement sensor is moved across the skin of a human hand.

FIG. 41 represents an example plot 350 of a signal 360 generated by detector 312A, 312B, or 312C as sensor 100A, 100B, or 100C is moved across the skin of a human hand in the x-direction. The x-axis of plot 350 may be scaled such that the movement of the signal 360 on the x-axis matches the distance of movement of sensor 100A/100B/100C across the skin.

The amplitude of the signal 360 corresponds with the texture of the skin surface, which includes numerous intrinsic skin features 70. As shown, signal 360 includes a series of peaks 362, valleys 364, and other characteristics. Intrinsic skin features 70 may be identified from signal 360 based on any suitable parameters or algorithms.

For example, one or more of the following criteria may be used for identifying intrinsic skin features 70 based on signal 360:

(a) the raw amplitude of a peak 362, (b) the amplitude of a peak 362 relative to the amplitude of one or more other peaks 362 (e.g., one or more adjacent peaks 362), (c) the amplitude of a peak 362 relative to the amplitude of one or more valleys 364 (e.g., one or more adjacent valleys 364), (d) the raw amplitude of a valley 364, (e) the amplitude of a valley 364 relative to the amplitude of one or more other valleys 364 (e.g., one or more adjacent valleys 364), (f) the amplitude of a valley 364 relative to the amplitude of one or more valleys 364 (e.g., one or more adjacent valleys 364), (g) the rate of increase in amplitude of signal 362 (i.e., positive slope of signal 360) for a particular portion of signal 360, (h) the rate of decrease in amplitude of signal 360 (i.e., negative slope of signal 360) for a particular portion of signal 362, (i) the x-direction distance between adjacent peaks 362 ($D_1$, $D_2$, $D_3$, etc), (j) the x-direction distance between adjacent valleys 364, or (k) any other suitable criteria.

An algorithm 154 may identify intrinsic skin features 70 based on any one or any combination of more than one of the criteria listed above. Such algorithm 154 may include (predefined or real-time calculated) threshold values to which one or more of the criteria listed above are compared. In some embodiments that identify intrinsic skin features 70 based on peaks 362 in signal 360, the algorithm 154 may be able to distinguish major or global peaks (e.g., peaks 362) from minor or local peaks (e.g., local peak 368), and use only the major or global peaks 362 for identifying intrinsic skin features 70. As another example, the algorithm 154 may distinguish major or global valleys (e.g., valleys 364) from minor or local valleys (e.g., local valley 369), and use only the major or global valleys 364 for identifying intrinsic skin features 70.

Figure 42:
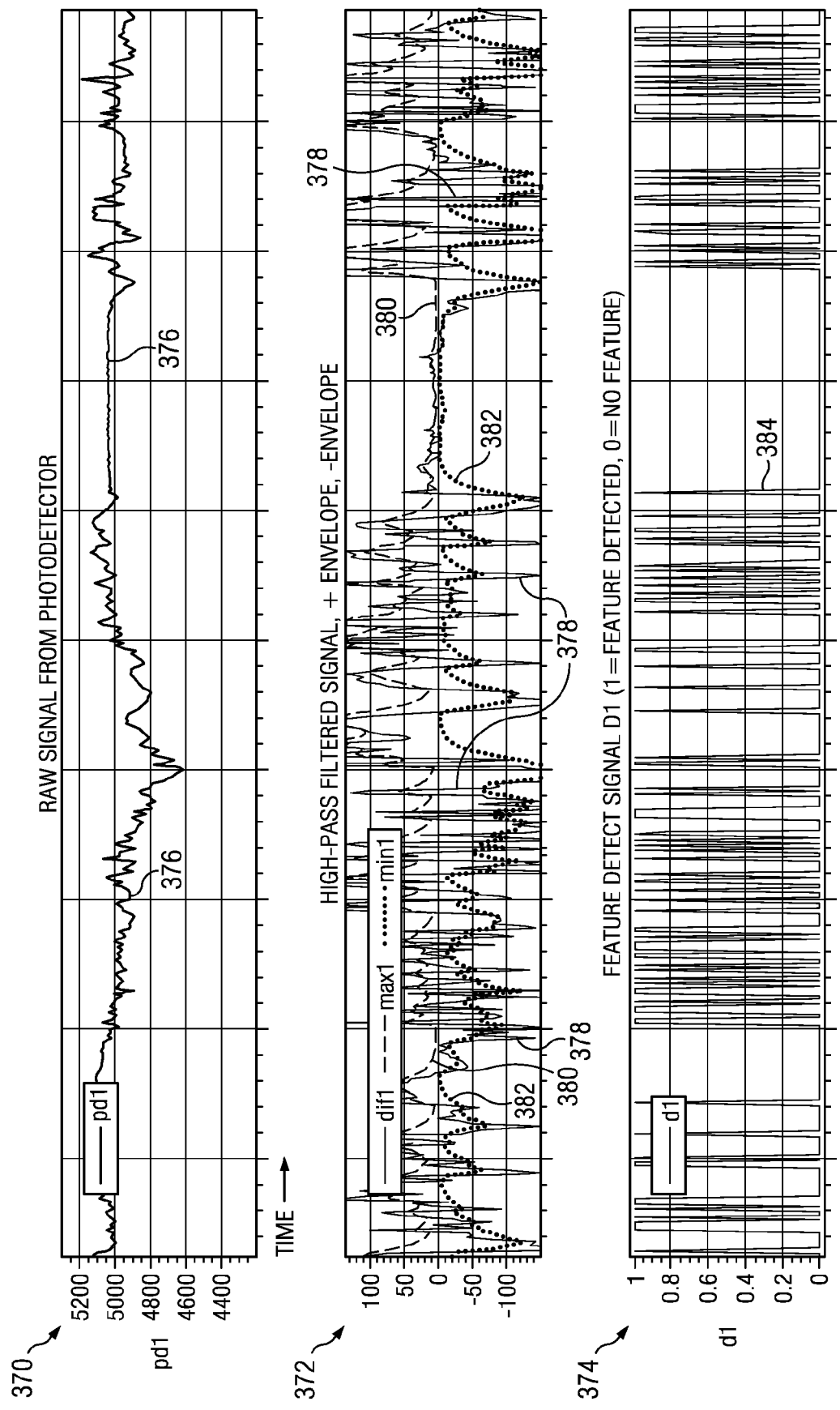
FIG. 42 illustrates three data plots: a raw signal plot, filtered signal plot, and a intrinsic skin feature detection plot, for detecting skin features based on signals from a displacement sensor, according to certain embodiments.

One example displacement algorithm that may be used with a single-pixel displacement sensor (e.g., sensor 100A or 100B) to identify intrinsic skin features 70, and detect displacement of device 10, is discussed below with reference to FIG. 42. FIG. 42 illustrates three data plots: a raw signal plot 370, filtered signal plot 372, and an intrinsic skin feature detection plot 374. The example displacement algorithm takes as input a raw signal from a photodetector (representing reflectance/remittance vs. time), and generates as output a digital pulse "1" when a displacement has been detected, and "0" when no displacement has been detected. In FIG. 42, each plot 370, 372, and 374 shows the specified signals plotted against time on the horizontal axis.

Raw signal plot 370 shows the raw input signal "pd1" 376, which includes amplitude variations corresponding to displacement of the sensor across the skin (the amplitude variations correspond to intrinsic skin features 70 on the skin), and flatter areas corresponding to the sensor dwelling in the same place on the skin.

As shown in filtered signal plot 372, the algorithm extracts a high-pass filtered version "diff1" 378 of the raw signal pd1 and also a positive-tracking and negative-tracking envelope indicated as "max1" 380 and "min1" 382, respectively. The positive envelope "max1" 380 is created at each point in time by adding a fraction of the current high-pass-filtered positive signal "dif1$p$" to the previous time-step value of the positive envelope signal "max1", where "dif1$p$" is formed from the high-pass filtered signal "dif1":

dif1$p$=dif1(dif1>0)

dif1$p$=0(dif1<=0)

Similarly, the negative envelope "min1" 382 is created the same way from "dif1$n$", which is the high-pass filtered negative signal:

dif1$n$=dif1(dif1<0)

dif1$n$=0(dif1>=0)

Finally, as shown in the intrinsic skin feature detection plot 374, the feature-detect signal "d1" 384 is set to 1 at any time step in which "dif1" has a zero crossing (i.e., where previous time step and current time step have a different sign) AND "max1" exceeds a threshold value, AND "min1" exceeds a threshold value. Otherwise, "d1" is set to 0. The threshold limits may be designed to prevent non-desirable outputs (e.g., feature-detection false positives and/or false negatives) due to random sensor or circuit noise levels. The zero-crossing requirement may also be designed to prevent non-desirable outputs (e.g., feature-detection false positives and/or false negatives) when the photosignal dif1 is entirely positive or negative, as when the photosensor is initially brought up against a surface (signal shows large increase with time), or removed from it (signal decreases).

From feature detection plot 374, the displacement of the sensor relative to the skin can be determined by counting the number of detected features 70. The algorithm may then make control decisions by (a) comparing the number of detected features 70 to one or more predetermined threshold numbers (e.g., allow continued treatment if at least three features 70 have been detected), or (b) by multiplying the number of detected features 70 by a known nominal or average distance between features 70 (e.g., as determined based on experimental testing) to determine displacement distance (e.g., in millimeters), and then comparing the determined displacement distance to one or more predetermined threshold distances (e.g., allow continued treatment if the determined displacement exceeds 2 mm). It can be appreciated by one of ordinary skill in the art that, if desired, this embodiment could also be used to create a velocity sensor if rate information was also obtained and used or a dwell sensor.

In some embodiments, the example algorithm may be utilized in a system including a single sensor (e.g., single-pixel displacement sensor 100A or 100B) having a single detector (e.g., detector 312A or 312B). In other embodiments, the example algorithm may be utilized in a system with more than one sensors (e.g., more than one sensor 100A and/or 100B) or with a sensor 100 that includes more than one detector 312 (e.g., a sensor 100A or 100B including more than one detector 312A or 312B). Such embodiments may thus generate multiple feature detection signals 384, each corresponding to a different sensor 100 or detector 312 with the same type of features detected or different types of features detected.

In embodiments including multiple sensors 100 or detectors 312, the algorithm may make control decisions based on the multiple feature detection signals 384 in any suitable manner. For example, the algorithm may generate a control signal only if each of the multiple feature detection signals 384 detects a predetermined number of features 70 (which may provide relatively greater resistance to noise or possible fault conditions). Or, the algorithm may generate a control signal if any of the multiple feature detection signals 384 detects a predetermined number of features 70 (which may provide relatively greater detection sensitive for surfaces with less texture and smaller amplitude reflectance features). Or, the algorithm may generate control signals based on the total number of features 70 detected by the multiple feature detection signals 384. The algorithm can also be designed to the identify an outlier feature detection signal 384 (as compared to the other feature detection signal 384), and ignore such signal 384, at least while it remains an outlier.

A sample of humans was tested with a particular embodiment of sensor 100A, and identifying intrinsic skin features 70 according to the example algorithms discussed above. The testing involved moving sensor 100A in a straight line across the surface of the test subjects' skin, such as face or arm skin. The resulting test data using the particular embodiment of sensor 100A indicated that adjacent intrinsic skin features 70 (texture or roughness, in this case) are located about 0.3-0.4 mm apart on average. In other words, with reference to FIG. 40, the test data indicated an average spacing $D_1$, $D_2$, $D_3$, etc. of about 0.3-0.4 mm.

The displacement of device 10 can be determined or approximated using this experimental data, e.g., the average spacing between intrinsic skin features 70. For example, the displacement of device 10 can be determined or approximated by multiplying the number of intrinsic skin features 70 identified by system 132 by the experimentally determined average spacing between intrinsic skin features 70.

Thus, displacement-based control system 132 (in particular, control electronics 30) may control device 10 based on the determined or approximated displacement of device 10 across the skin. For example, displacement-based control system 132 may control one or more controllable operational parameters of device 10 (e.g., operational aspects of treatment radiation source 14) based on the number of intrinsic skin features 70 identified by system 132 for a displacement of device 10 across the skin. For example, system 132 may control device 10 to pulse the beam source(s) of device 10 (thus generating one or more treatment spots 62) each time device 10 is displaced X mm, as determined by identifying N intrinsic skin features 70. For example, if experimental data indicates that intrinsic skin features 70 are spaced by an average of 0.4 mm, system 132 may control device 10 to pulse the beam source(s) each time device 10 is displaced approximately 1.2 mm, as determined by identifying three intrinsic skin features; the next pulse of the beam source(s) is not initiated delivered until/unless device 10 is displaced another approximately 1.2 mm (i.e., until three intrinsic skin features 70 are identified by system 132). Additional details and examples of the control of device 10 by system 132 are provided below.

Thus, in some embodiments, control systems 18, including displacement-based control system 132, controls operational aspects of device 10 (e.g., operational aspects of treatment radiation source 14) based on the displacement of device 10 across the skin, independent of the rate, speed, or velocity of device 10 moving across the skin. In some embodiments device 10, including displacement-based control system 132, is not configured for detecting or measuring any data indicative of the rate, speed, or velocity of device 10 moving across the skin, or for determining or attempting to determine the rate, speed, or velocity of device 10 moving across the skin. Rather, device 10 is configured for detecting or measuring data indicative of the lateral displacement of device 10 relative to the skin, and for determining the lateral displacement of device 10 using such data, e.g., as discussed above. In other words, device 10 can be moved at any rate, including very slowly, and pulses are delivered only if sufficient distance been translated relative to prior pulse location.

In other embodiments, device 10 may include a speed detection system, e.g., including a motion/speed sensor 102, for detecting or measuring data indicative of the rate, speed, or velocity of device 10 moving across the skin, and for determining or attempting to determine the rate, speed, or velocity of device 10 based on such data. Such speed detection sensor or system may be provided in addition to, or in place of, displacement-based control system 132 and displacement sensor 100A.

In other embodiments, device 10 may include a dwell sensor 116 for measuring data indicative of whether device 10 is stationary or stationary within a certain tolerance with respect to the skin. Dwell sensor 116 may employ aspects of displacement sensor 100 described above but may be configured to provide information specifically about whether device 10 is stationary. For example, all or portions of the example algorithm described above for single-pixel displacement sensor 100A/100B may be used to determine when device 10 is substantially stationary (e.g., by recognizing the flat spots in the raw data signal 376 shown in FIG. 42) and device 10 may be controlled based on that information (e.g., radiation source 14 may be disabled if device 10 is determined to be stationary or dwelling).

Figure 43:
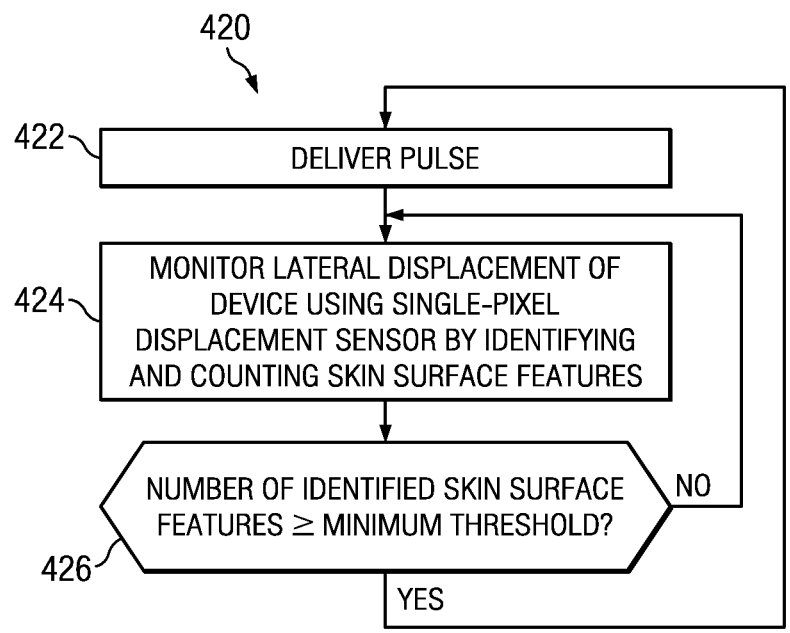
FIG. 43 illustrates a more specific example of the general method of FIG. 36 for controlling a device using a displacement-based control system, according to certain embodiments.

FIG. 43 illustrates a more specific example of the general method 400 of FIG. 36. In particular, FIG. 43 illustrates a method 420 for controlling device 10 using displacement-based control system 132 that employs a single-pixel displacement sensor 100A, 100B, or 100C, while device 10 is used either in a gliding mode or a stamping mode, according to certain embodiments.

At step 422, device 10 pulses the beam source(s) of device 10, to generate one or more treatment spots 62 on treatment area 40, as discussed above regarding step 402. If device 10 is being used in a gliding mode, the user may glide device 10 across the skin during the first pulse of the beam source(s). If device 10 is being used in a stamping mode, the user may hold device 10 stationary on the skin during the first pulse of the beam source(s).

At step 424, displacement-based control system 132 performs a first monitoring process to monitor and analyze the displacement of device 10 across the surface of the skin using single-pixel displacement sensor 100A/100B/100C. For example, as discussed below, displacement-based control system 132 may analyze signal 360 to identify and maintain a count of intrinsic skin features 70 in the skin as device 10 is moved across the skin (e.g., in a gliding mode, during and/or after the first pulse of the beam source(s); or in a stamping mode, after the first pulse of the beam source(s)). System 132 may begin the first monitoring process at the initiation or conclusion of the first pulse of the beam source(s) or upon any other predefined event or at any predetermined time.

At step 426, displacement-based control system 132 controls the pulsing of the beam source(s) based on the number of intrinsic skin features 70 identified at step 424. For example, in some embodiments, displacement-based control system 132 initiates a second pulse of the beam source(s) upon identify a predetermined number of features 70 in the skin (e.g., 5 features). Thus, in such embodiments, a relatively constant spacing (e.g., a spacing corresponding to 5 skin features) between successive treatment spots 62 in the glide direction can be achieved regardless of the manual glide speed. Thus, the pulse frequency may vary dynamically as a function of the manual glide speed.

In other embodiments, device 10 (or the user) sets a defined pulse frequency (e.g., 15 Hz), as well as a predefined minimum number of intrinsic skin features 70 (e.g., 3 features) corresponding to a desired minimum spacing between successive treatment spots 62 in the glide direction (e.g., about 1 mm). Displacement-based control system 132 analyzes the count of identified features 70 maintained at step 424 and the defined pulse frequency to determine whether the providing the next pulse according to the defined pulse frequency would violate the minimum feature count (e.g., 3 features) between successive pulses. If not, displacement-based control system 132 allows device 10 to continue pulsing at the defined pulse frequency. However, if so (i.e., if providing the next pulse according to the defined pulse frequency would violate the minimum feature count), displacement-based control system 132 may control radiation source 14 to delay the next pulse at least until the minimum feature count is achieved by system 132 (thus providing a minimum spacing (e.g., about 1 mm) between successive treatment spots 62), or system 132 may other control radiation source 14 to prevent over-treatment (e.g., decreasing the beam intensity, turning off radiation source 14, providing feedback to the user, etc.)

Thus, in certain embodiment, control of device 10 (e.g., controlling the pulse timing or other aspects of treatment radiation source 14) to provide a desired spot spacing and/or to avoid over-treatment of a particular area is not based on any signals related to the rate, speed, or velocity of device 10 moving across the skin. As discussed above, in some embodiments device 10 is not configured for detecting or measuring any data indicative of the rate, speed, or velocity of device 10 moving across the skin, or for determining or attempting to determine the rate, speed, or velocity of device 10 moving across the skin.

Multi-Pixel Displacement Sensor

As mentioned above, in some embodiments displacement sensor 100 is a multi-pixel displacement sensor 100 that employs two pixels (i.e., two reflected beams of light for generating two signals 360), three pixels, four pixels, or more. For example, some embodiments employ a multi-pixel imaging correlation sensor 100D, of the type used in optical mice for computer input, for detecting displacement along the skin.

Figure 44:
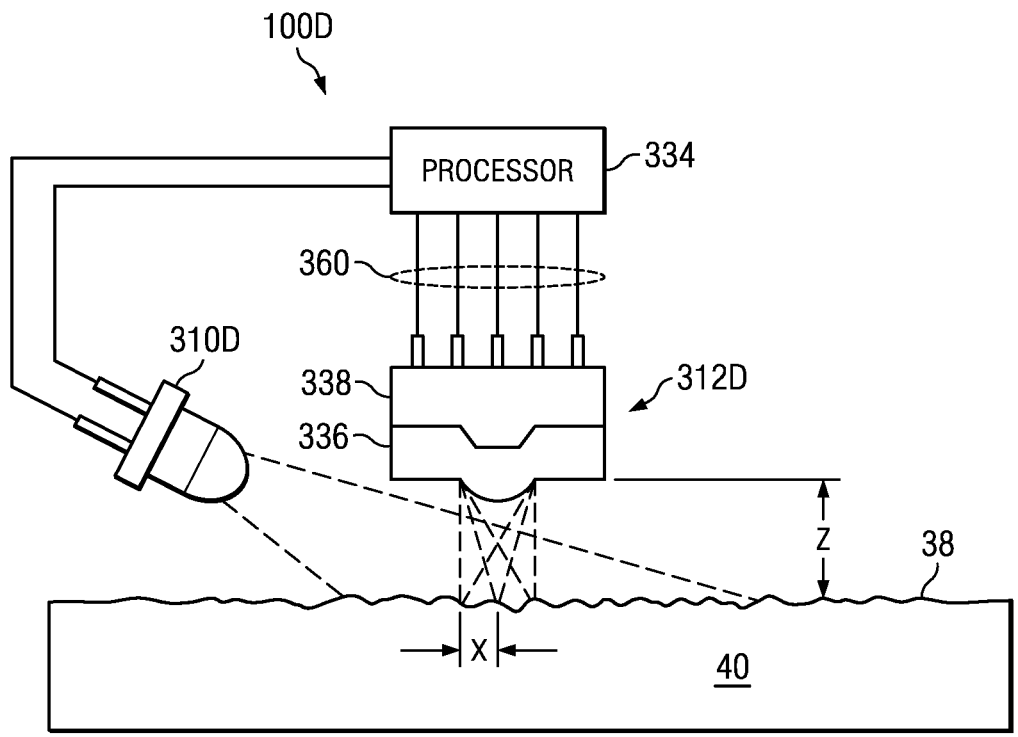
FIG. 44 illustrates an example multi-pixel imaging correlation sensor, of the type used in optical mice for computer input, for detecting displacement along the skin, according to certain embodiments.

FIG. 44 illustrates an example multi-pixel imaging correlation sensor 100D, of the type used in optical mice for computer input, for detecting displacement along the skin, according to certain embodiments. Displacement sensor 100D may include a light source 310D, a light detector 312D, and a processor 334.

Light source 310D may be a light-emitting diode (LED) or any other suitable light source, e.g., as discussed above regarding light source 310A. Light source 310D may be arranged to deliver light at an oblique angle with respect to the skin surface 32, as shown in FIG. 44, Light detector 312D may include a molded lens optic 336 and an imaging chip 338. In some embodiments, sensor 100D is configured such that the skin is within the focal plane of molded lens optic 336, which focal plane may be located several millimeters away from the surface of molded lens optic 336, as indicated by distance z in FIG. 44. Optionally, a system of relay lenses may be added between detector 312D and skin surface 32 to extend the total distance from the external focal plane to detector 312D.

Detector 312D may be configured to generate a two-dimensional multi-pixel "image" of the area of skin surface 32 illuminated by light source 310D. The image may consists of a two-dimensional array of pixels, each pixel having a signal 360 similar to signal 360 of single-pixel sensor 100A or 100B. Imaging chip 338 may be configured to generate a digital output stream to processor 334 corresponding to the multi-pixel signal array.

Processor 334 may be configured to drive light source 310D and receive and analyze the multi-pixel array of signals from light detector 312D. In particular, processor 334 may compare different multi-pixel images received from detector 312D (e.g., successively received images) to determine linear displacements in one or more directions, rotational displacements, and/or lateral displacements of sensor 100D across the skin surface 32.

It should be understood that although the example embodiments discussed above may be suitable for detecting roughness-type skin features, other embodiments of sensor 100 may detect any other types of intrinsic skin features, such as pigment detection in the epidermis or epidermis/dermal junction or vascularity patterns such as the microvasculature in the skin, for example, using similar or analogous techniques to those discussed above.

Figure 45:
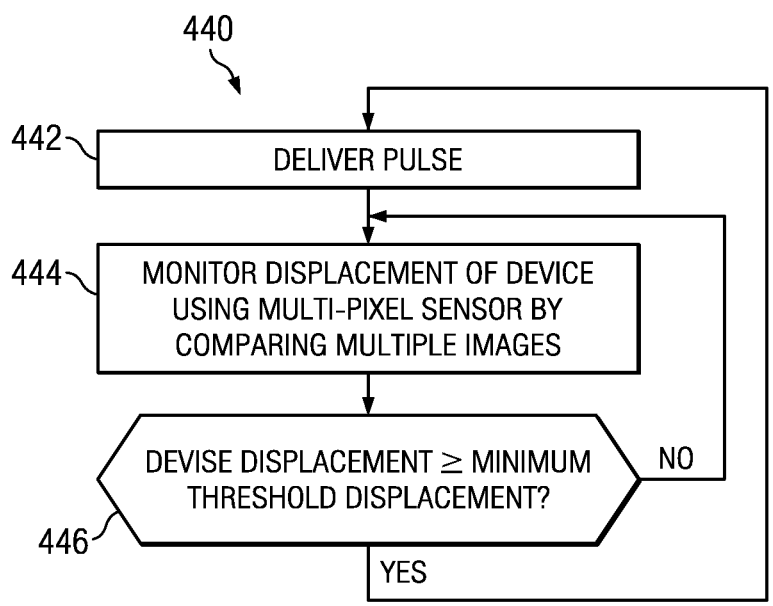
FIG. 45 illustrates an example method for controlling device using a displacement-based control system that employs a multi-pixel displacement sensor, while device is used either in a gliding mode or a stamping mode, according to certain embodiments.

FIG. 45 illustrates an example method 440 for controlling device 10 using displacement-based control system 132 that employs a multi-pixel displacement sensor 100D, while device 10 is used either in a gliding mode or a stamping mode, according to certain embodiments.

At step 442, device 10 pulses the beam source(s) of device 10, to generate one or more treatment spots 62 on treatment area 40, as discussed above regarding step 402. If device 10 is being used in a gliding mode, the user may glide device 10 across the skin during the first pulse of the beam source(s). If device 10 is being used in a stamping mode, the user may hold device 10 stationary on the skin during the first pulse of the beam source(s).

At step 444, displacement-based control system 132 performs a first monitoring process to monitor and analyze the lateral displacement of device 10 across the surface of the skin using multi-pixel sensor 100D. Displacement-based control system 132 analyzes signals 360 as device 10 is moved across the skin (e.g., in a gliding mode, during and/or after the first pulse of the beam source(s); or in a stamping mode, after the first pulse of the beam source(s)). System 132 may begin the first monitoring process at the initiation or conclusion of the first pulse of the beam source(s) or upon any other predefined event or at any predetermined time.

At step 446, displacement-based control system 132 controls the pulsing of the beam source(s) based on the displacement of device 10 determined at step 444. For example, in some embodiments, displacement-based control system 132 initiates a second pulse of the beam source(s) upon determining that device 10 has moved a particular predetermined distance across the skin (e.g., 3 mm), based on signals from multi-pixel sensor 100D. Thus, in such embodiments, a substantially constant spacing (e.g., 3 mm) between successive treatment spots 62 in the glide direction can be achieved regardless of the manual glide speed. Thus, the pulse frequency may vary dynamically as a function of the manual glide speed.

In other embodiments, device 10 (or the user) sets a defined pulse frequency (e.g., 15 Hz), as well as a predefined minimum device displacement for providing a predefined minimum spacing between successive treatment spots 62 in the glide direction (e.g., 1 mm). Displacement-based control system 132 analyzes the monitored displacement of device 10 determined at step 444 (based on signals from multi-pixel sensor 100D) and the defined pulse frequency to determine whether the providing the next pulse according to the defined pulse frequency would violate the minimum spot spacing (e.g., 1 mm). If not, displacement-based control system 132 allows device 10 to continue pulsing at the defined pulse frequency. However, if so (i.e., if providing the next pulse according to the defined pulse frequency would violate the minimum spot spacing), displacement-based control system 132 may control radiation source 14 to delay the next pulse at least until system 132 determines that the minimum device displacement has been achieved (thus ensuring the predefined minimum spacing between successive treatment spots 62), or system 132 may other control radiation source 14 to prevent over-treatment (e.g., decreasing the beam intensity, turning off radiation source 14, providing feedback to the user, etc.)

Thus, in certain embodiment, control of device 10 (e.g., controlling the pulse timing or other aspects of treatment radiation source 14) to provide a desired spot spacing and/or to avoid over-treatment of a particular area is not based on any signals related to the rate, speed, or velocity of device 10 moving across the skin. As discussed above, in some embodiments device 10 is not configured for detecting or measuring any data indicative of the rate, speed, or velocity of device 10 moving across the skin, or for determining or attempting to determine the rate, speed, or velocity of device 10 moving across the skin.

Roller-Type Displacement Sensor 100 or Motion/Speed Sensor 102

In some embodiments, device 10 may include one or more roller-based sensors 118 that function as a displacement sensor 100, or dwell sensor 116 or as a motion/speed sensor 102, or all. Roller-based sensor 118 may be arranged at or near the treatment tip 42 of device 10, and may include a roller 450 having a leading surface that is generally flush with, or projects slightly forward from the leading surface of the surrounding or adjacent portion of housing 24. In some embodiments, the leading surface of roller 450 may define a skin-contacting surface 74, which may or may not affect the distance (if any) of the treatment window 44 from the skin surface, e.g., depending on the closeness of the roller 405 to the window 44 and/or the force at which device 10 is pressed against the skin by the user.

FIGS. 46A-46G illustrate some example embodiments of a roller-based sensor 118A-118G that may be used in certain embodiments of device 10. Each embodiment includes a roller 450 coupled (e.g., mechanically, optically, magnetically, electrically, etc.) to a detection system 452 configured to generate signals indicative of (a) the displacement of device 10 (e.g., based on a detected amount of angular rotation of roller 45), or (b) the manual glide speed of device 10 (e.g., based on a detected speed of rotation of roller 45), or (c) a dwell sensor (e.g., based on rotation or not rotation), or (d) all of the above.

As device 10 is manually moved across the skin, roller 450 turns or "rolls" by a degree and at a speed corresponding to the lateral displacement and manual glide speed, respectively, of the device relative to the skin surface. Detection system 452, via its coupling or interaction with roller 450, generates signals indicative of the lateral displacement and/or manual glide speed, and communicates such signals to processor 150, which may convert and/or process such signals to determine the displacement and/or glide speed and/or stationary status of device 10. The determined displacement and/or glide speed and/or stationary status of device 10 may then be used for controlling one or more controllable operational parameters of device 10 (e.g., control operational parameters of radiation source 14), e.g., as discussed herein.

In some embodiments, roller-based sensor 118 is configured to operate as a displacement sensor 200 for use in displacement-based control system 132, and may be used for any of the displacement-based control techniques discussed herein. In some embodiments, roller-based sensor 118 measures, detects, or generates signals indicative of, the displacement of device 10, but does not measure, detect, or generate signals indicative of, the manual glide speed of device 10.

In an example embodiment, roller 450 has a diameter of about 4 mm, such that a 29 degree rotation of roller 450 corresponds to 1 mm displacements of device 10 (assuming no slipping between roller 450 and skin). In some embodiments, detection system 452 may be sensitive to device displacements to a granularity of about 1 mm.

Figure 46A:
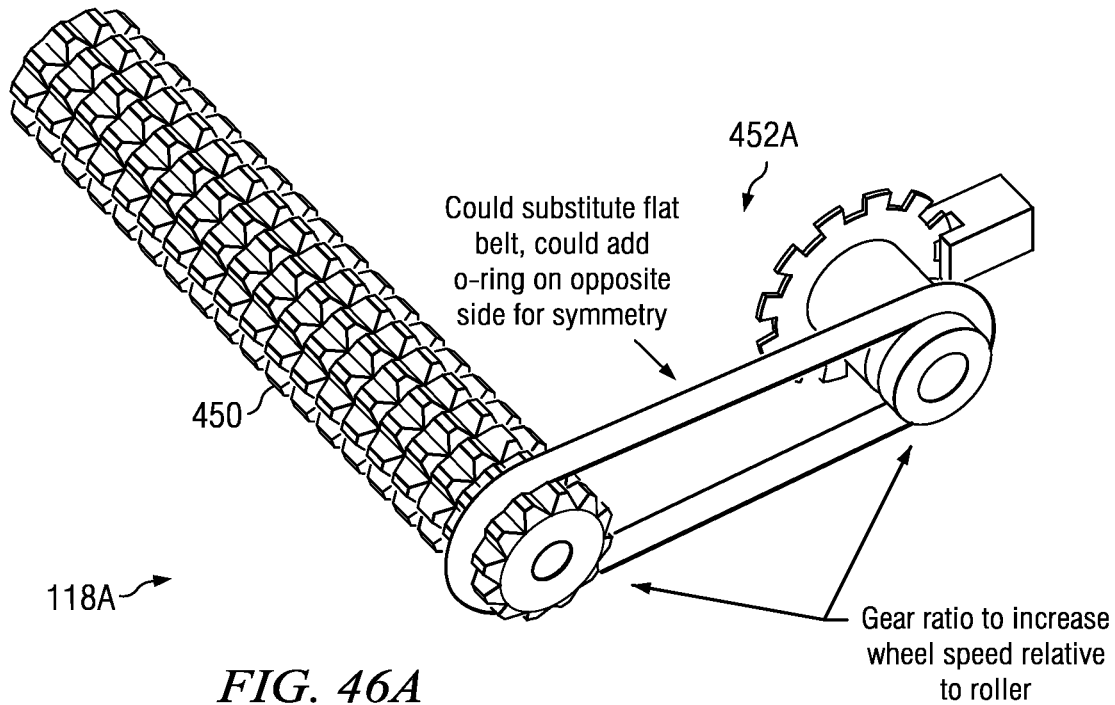
FIGS. 46A-46G illustrate example embodiments of a roller-based sensor that may be used a displacement sensor, or a motion/speed sensor, or both, for use in certain embodiments.

FIG. 46A illustrates an example roller-based sensor 118A that includes a belt-driven optical-interrupt detection system 452A to generate signals indicative of the displacement and/or glide speed of device 10.

Figure 46B:
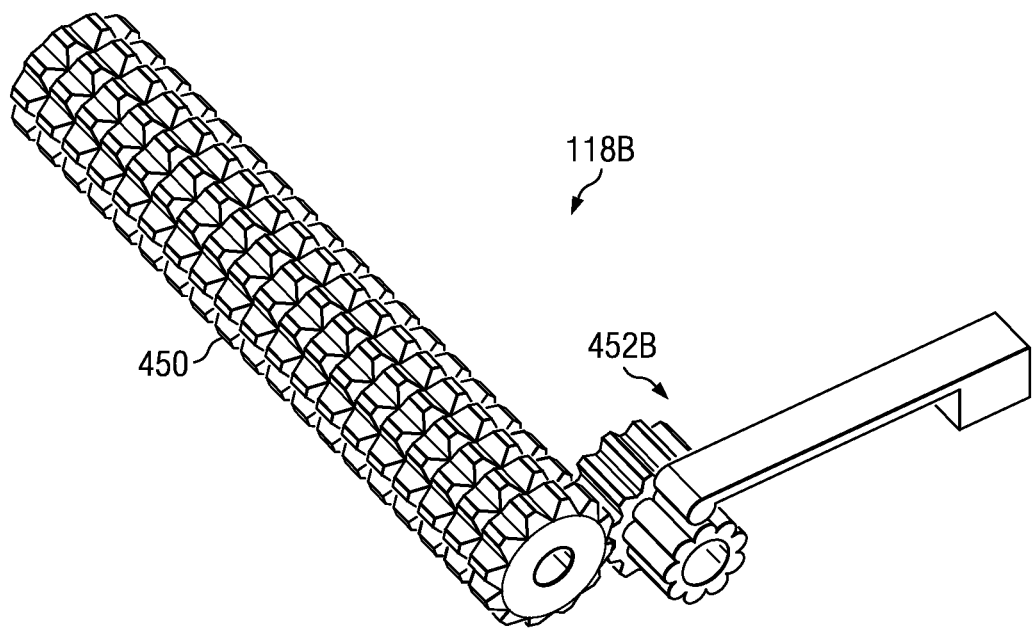
Figure 46C:
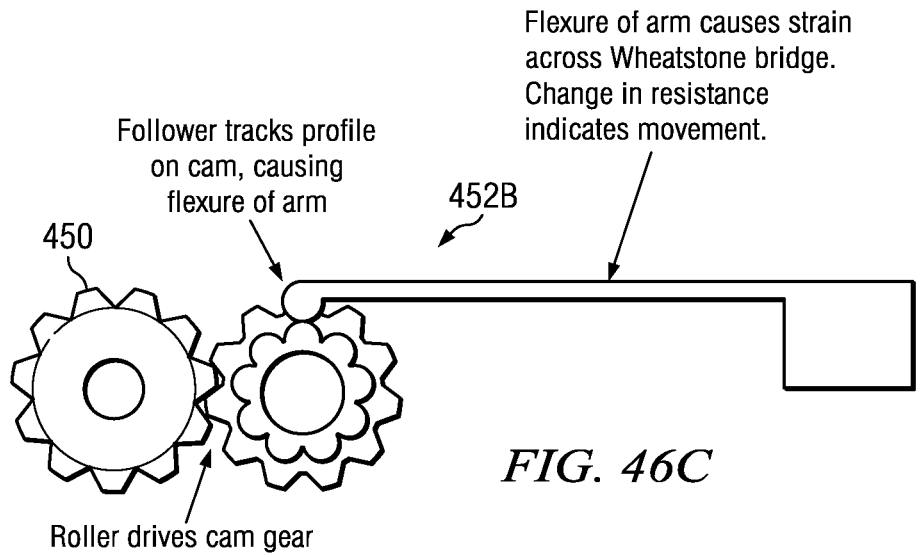

FIGS. 46B and 46C illustrate an example roller-based sensor 118B that includes a detection system 452B that generates signals indicative of the displacement and/or glide speed of device 10 based on the flexure of a physical arm, which causes strain across a Wheatstone bridge, thus causing changes in resistance corresponding to device movement.

Figure 46D:
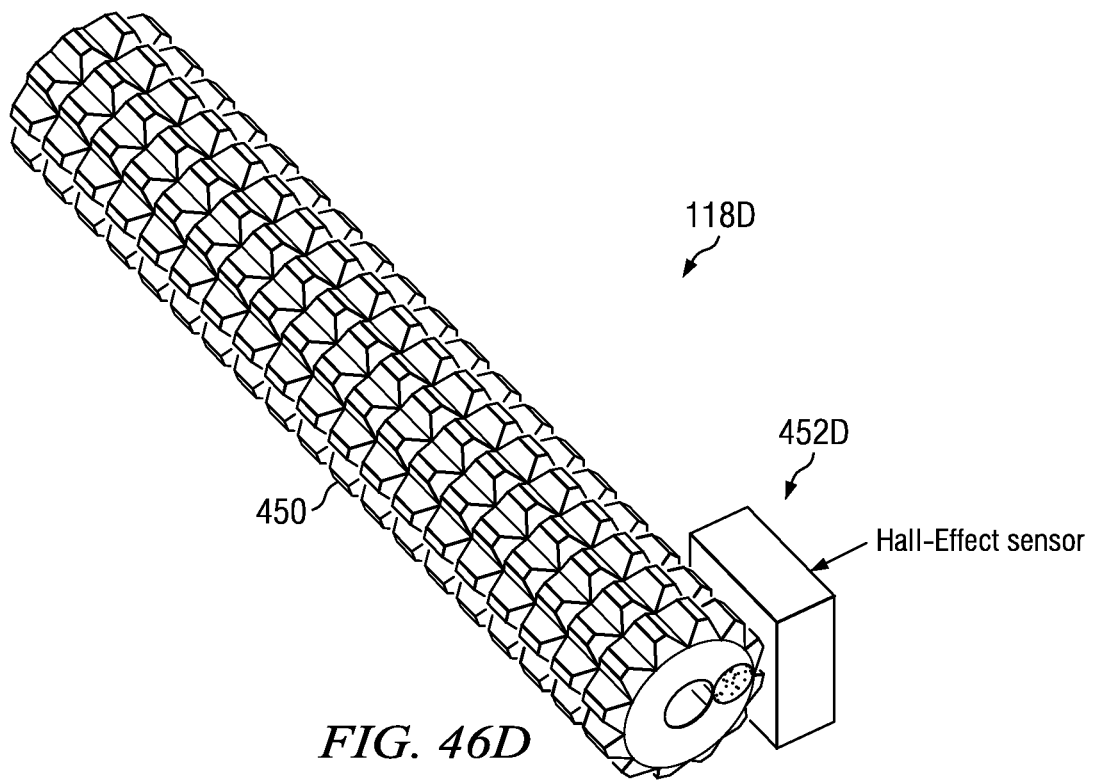

FIG. 46D illustrates an example roller-based sensor 118D that includes a detection system 452D that generates signals indicative of the displacement and/or glide speed of device 10 based on an interaction between a Hall-effect sensor and one or more magnets around the perimeter of roller 450.

Figure 46E:
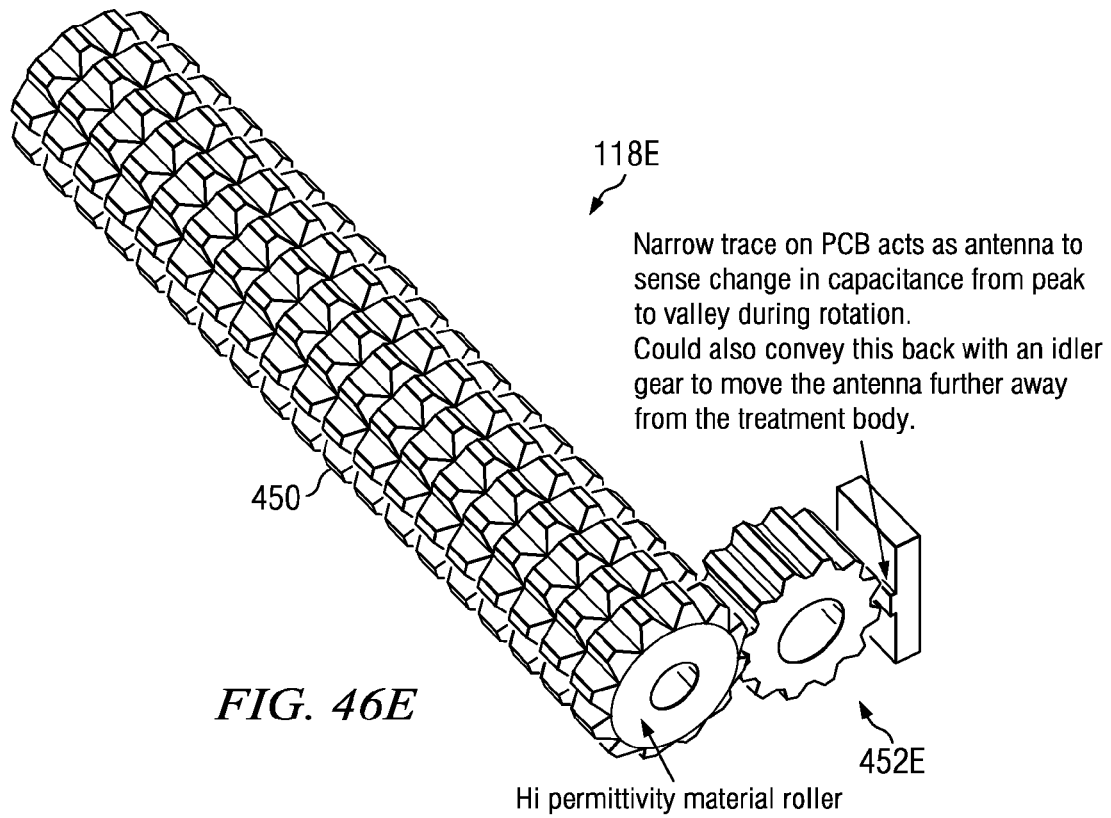

FIG. 46E illustrates an example roller-based sensor 118E that includes a detection 452E to generate signals indicative of the displacement and/or glide speed of device 10 based on a measured capacitance between an "antenna" and a gear or other rotating element.

Figure 46F:
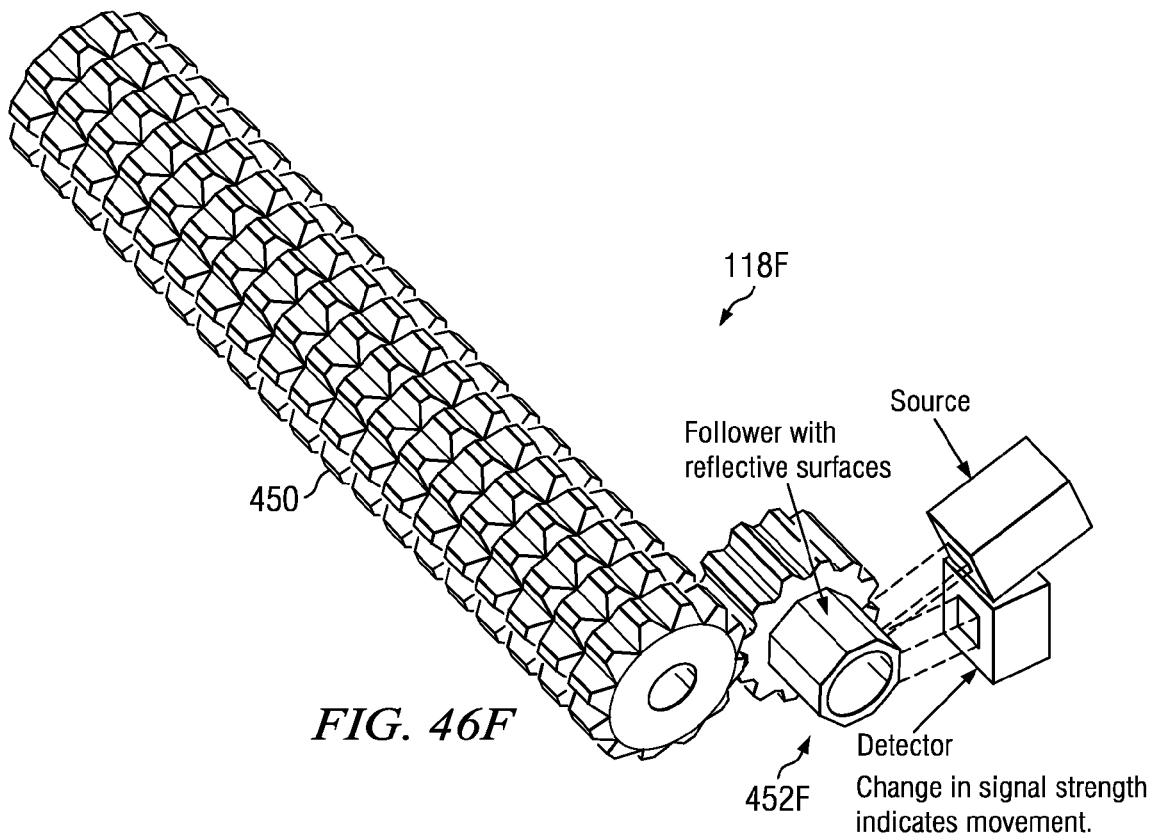

FIG. 46F illustrates an example roller-based sensor 118F that includes a detection system 452F to generate signals indicative of the displacement and/or glide speed of device 10 based on measurements of reflected optical radiation.

Figure 46G:
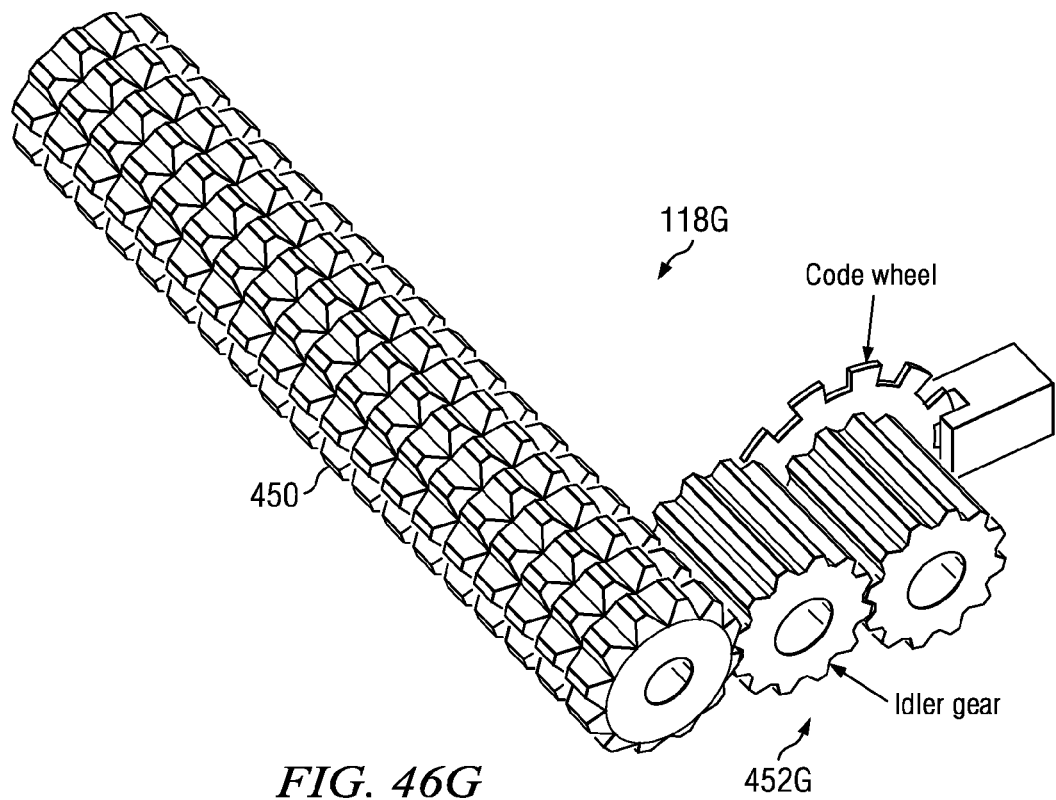

Finally, FIG. 46G illustrates an example roller-based sensor 118G that includes a gear-driven optical-interrupt detection system 452G to generate signals indicative of the displacement and/or glide speed of device 10.

Capacitive Sensors

One or more sensors 46 of device 10 may be, or may include, capacitive sensors. As discussed above, skin-contact sensor 104 may be a capacitive sensor, in which the signal amplitude is analyzed to determine whether sensor 104 is in contact or sufficient proximity with the skin. In addition, any of displacement sensor 100, motion/speed sensor 102, and/or dwell sensor 116 may be capacitive sensors, or may include capacitive sensors in addition to other types of sensors (e.g., a sensor 100, 102, or 116 may include an optical reflectance/remittance sensor in addition to a capacitive sensor for providing the desired functionality, e.g., to provide redundancy).

A capacitive sensor in contact with the skin (e.g., a capacitive sensor located at the application end 42 of device 10 may generate a signal (e.g., a high-frequency signal) indicating a measure of capacitance associated with the contact between the sensor and the skin. For example, a capacitive sensor's signal may be inversely proportional to the relative displacement between the sensor and the target surface. Because the surface of a human's skin is not perfectly smooth and/or because a human cannot achieve perfectly steady motion during manual movement of device 10, static friction (stiction) between device 10 and the skin and/or other physical principles may result in "stick-and-slip" movement of device 10 across the skin, which causes micro-displacement between the sensor and the skin surface. This micro-displacement due to stick-and-slip movement of device 10 may result in a translational signal added to the nominal steady-state capacitance signal of the sensor, to provide a total capacitance signal. The amplitude and/or other aspects of the total capacitance signal may be analyzed to determine whether the device is moving across the skin, or dwelling at the same location. Thus, a capacitive sensor may be used as a dwell sensor 116. Such analysis may include any suitable algorithms, e.g., comparing the signal to one or more threshold values.

As another example, the total capacitance signal may be analyzed to determine or estimate the speed of device 10 moving across the skin. Thus, a capacitive sensor may be used as a motion/speed sensor 102. As another example, the total capacitance signal may be analyzed to determine or estimate the displacement of device 10 moving across the skin. Thus, a capacitive sensor may be used as a displacement sensor 100.

Treatment Sessions

In some embodiments, control systems 18 define and control individual treatment sessions based on one or more "treatment delimiters" such as (a) a total number of treatment spots 62 generated in the treatment area 40, (b) a total amount of energy delivered to the treatment area 40, (c) a total treatment time, or any other suitable delimiter(s).

In some embodiments, treatment delimiters are specified for different "types" of treatments. Different types of treatments may include (a) treatments for different areas of the body (e.g., periorbital area, areas near the mouth, the back of the hand, the stomach, the knees, etc.), (b) different treatment energy or intensity levels (e.g., high energy treatment, medium energy treatment, low energy treatment), (c) different treatments for different stages of a multi-session treatment plan (e.g., a first session treatment, a mid-stage session treatment, or a final-session treatment), or any other different types of treatments.

Further, treatment delimiters may be specified for different combinations of treatment types. For example, different values for "total treatment spots 62 generated" may be specified for different combinations of treatment area and treatment energy level: (a) 4,000 treatment spots 62 for high energy periorbital treatment, (b) 7,000 treatment spots 62 for low energy periorbital treatment, (c) 6,000 treatment spots 62 for high energy hand treatment, and (d) 10,500 treatment spots 62 for low energy hand treatment.

Treatment delimiters for different treatment types (or combinations of different treatment types) may be predetermined and programmed into device 10, set or modified by a user via a user interface 18, determined by device 10 based on user input, sensors (such as skin temperature sensors), settings stored in device 10, and/or algorithms 154 stored in device 10, or determined in any other suitable manner. In some embodiments, treatment delimiters for different treatment types are determined based on experimental testing and preprogrammed into device 10. For example, experimental testing may determine that an appropriate treatment session for a periorbital region involves 1,000 treatment spots 62, an appropriate treatment session for a mouth region involves 1,300 treatment spots 62, and an appropriate treatment session for the back of the hand involves 2,700 treatment spots 62. These treatment delimiters may be stored in device 10 and implemented by control systems 18 as appropriate when a user selects from a "periorbital treatment," "mouth treatment," or "hand treatment" via user interface 18.

Where treatment sessions are defined by treatment delimiters that are not time-based, such as treatment sessions defined by (a) a total number of treatment spots 62 or (b) a total amount of energy delivered to the target, the manual glide speed of device 10 across the skin—with the possible exception of extremely fast glide speeds—may be largely or substantially irrelevant to the effectiveness of the treatment delivered during the session, at least in certain embodiments or configurations of device 10. For example, the manual glide speed may influence the number of times device 10 must be glided across the treatment area 40 to complete the treatment session (e.g., the faster the manual glide speed, the more glides are required to complete the session), but does not affect the specified treatment delimiter for the session, e.g., the total number of treatment spots 62 or the total amount of energy delivered to the treatment area 40.

Further, in some embodiments, the effectiveness of the treatment, as related to the spacing between treatment spots 62, is generally not affected by the manual glide speed of device 10. In embodiments that include displacement-based control system 132, which controls beam delivery, and thus treatment spot 62 generation, based on the determined displacement of device 10 across the skin, system 132 ensures at least a minimum spacing between successively delivered treatment spots 62, which reduces or substantially eliminates the chances of over-irradiation of any area. In particular, displacement-based control system 132 may ensure at least a minimum spacing between successively delivered treatment spots 62 during slow glide speeds, and without detecting or determining the manual glide speed. Thus, displacement-based control system 132 may reduce or substantially eliminate the chances of over-irradiation of any particular area, even for very slow glide speeds.

Further, where the treatment session involves multiple glides of device 10 across the treatment areas 40, the treatment spots 62 generated during different glides typically will not align with other, which generally results in an treatment spot 62 pattern with sufficient or desirable randomness and/or density uniformity to provide the desired treatment effects, without significantly over-irradiating any areas. Thus, although rapid glide speeds may require the user to perform more glides to reach the relevant treatment delimiter (e.g., total treatment spots 62 generated or total energy delivered), rapid glide speeds may provide a sufficient or desirable treatment spot 62 patterns, without over-irradiating any areas.

It should be noted that the manual glide speed may influence the shape of individual treatment spots 62, e.g., the extent of elongation, "blurring," or "smearing" of treatment spots 62, such as described above. Thus, operational aspects of device 10 may be configured such that within a reasonable range of glide speeds (i.e., less than very fast glide speeds), the elongation or smearing of treatment spots 62 does not substantially affect the physiological effectiveness of the treatment spots 62. In some embodiments or configurations of device 10, at very high glide speeds, the elongation or smearing of treatment spots 62 may significantly reduce the effectiveness of the treatment. For example, the energy density within a very elongated treatment spot 62 may be too low to provide the intended effects. Thus, the user may be provided general guidance (e.g., via display 32 or in a user manual) regarding the appropriate manual glide speed for the desired treatment effects. For example, the user may be instructed to glide device 10 across the treatment area 40 at manual glide speed of roughly three seconds per glide. The device may be configured to provide effective therapy at substantially all practical, or common, glide speeds used by consumers, so that therapy is substantially independent of glide speed.

Figure 47:
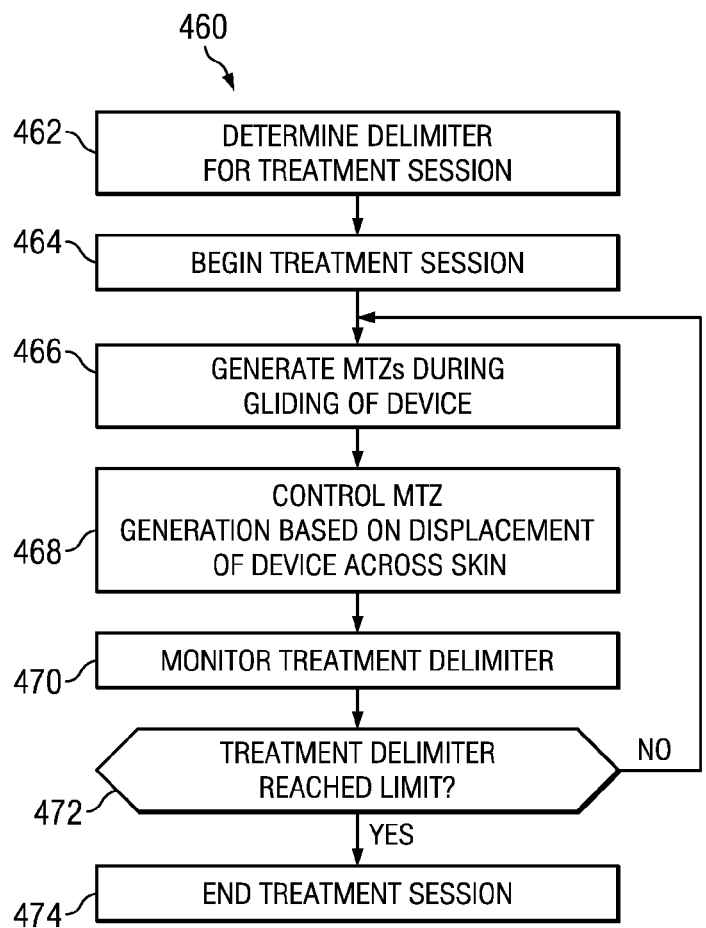
FIG. 47 illustrates an example method for executing a treatment session for providing treatment (e.g., fractional light treatment) to a user with certain embodiments of the device.

FIG. 47 illustrates an example method 460 for executing a treatment session for providing treatment (e.g., fractional light treatment) to a user with device 10. At step 462, one or more delimiters for a treatment session to be performed are determined in any suitable manner, e.g., as discussed above. For the purposes of this discussion it is assumed that a single treatment delimiter is determined. For example, control systems 18 may determine a predefined total number of treatment spots 62 for the treatment session based on a treatment area (e.g., periorbital area) selected by the user via a user interface 18: for example, 1200 treatment spots 62. (The number of treatment spots 62 may be assumed here to be equal to the number of beams 60 output by device 10).

At step 464, after the user has positioned device 10 against the treatment area 40, device 10 may begin the treatment session. In particular, control systems 18 may deliver manually scanned arrays (e.g., rows) of beams to the treatment area 40, thus generating an array of treatment spots 62, as indicated at step 466. If device is operating in a gliding mode, device 10 may glided across the skin continuously during the beam-delivery process. If device is operating in a stamping mode, device 10 may held in place during each pulse, and then moved, or glided, across the surface of skin to the next treatment location for the next pulse. The user may be instructed (e.g., by audible or visible notifications) when each pulse is delivered, and/or whether or when device 10 has been moved a sufficient distance for initiating the next pulse (as determined by displacement monitoring and control system 132). In either the gliding mode or the stamping mode, the user may glide or move the device across the treatment area 40 any number of times and any number of directions or patterns (e.g., to "paint" a two-dimensional target area) during the treatment session.

During the treatment session, as indicated as step 468, displacement monitoring and control system 132 may monitor the lateral displacement of device as it moves across the skin and control the delivery of beams/generation of treatment spots 62 accordingly, as discussed above. For example, system 132 may ensure that consecutive rows of treatment spots 62 are spaced apart in the glide direction by at least a minimum distance.

Also during the treatment session, control systems 18 may monitor the treatment delimiter determined at step 462, as indicated at step 470. For example, control systems 18 may maintain a running count of the number of treatment spots 62 generated during the treatment session. Steps 468 and 470 may be performed concurrently throughout the duration of the treatment session.

At step 472, control systems 18 determines whether the treatment delimiter has reached the predetermined limit. For example, control systems 18 may determine whether the number of treatment spots 62 that have been generated during the session has reached the predefined number of treatment spots 62 determined at step 462 (e.g., 1200 treatment spots 62). If so, the treatment session is completed at step 474. For example, control systems 18 may turn off treatment radiation source 14. If not, steps 466-472 are continued until the treatment delimiter is reached.

In some embodiments, a treatment session for providing treatment (e.g., fractional light treatment) to a user may be completed according to method 460 without regard to the manual glide speed of device 10 across the skin, e.g., as discussed above.

Eye Safety Sensor

In some embodiments, device 10 includes an optical eye safety sensor 114 configured to detect the presence of a cornea (or other eye tissue or feature) near a treatment output aperture of device 10, in order to help prevent unintended eye exposure to light from the treatment radiation source 14. For example, optical eye safety sensor 114 may be configured to distinguish between the presence of skin and the cornea, and enable device 10 to treat only the intended treatment area 40. Eye safety sensor 114 may be especially important for infrared treatment light of wavelength greater than 1400-nm, for which the eye injury risk is primarily in the cornea or for UV, visible, and/or near-IR where retinal hazards exist. In some embodiments, optical eye safety sensor 114 is relatively low cost, compact, easily packaged within a handheld enclosure (e.g., small and lightweight), and assembled from commonly available parts. Another example embodiment of an eye safety sensor is an imaging sensor with pattern recognition for shape, color, or other feature of the eye.

Figure 48:
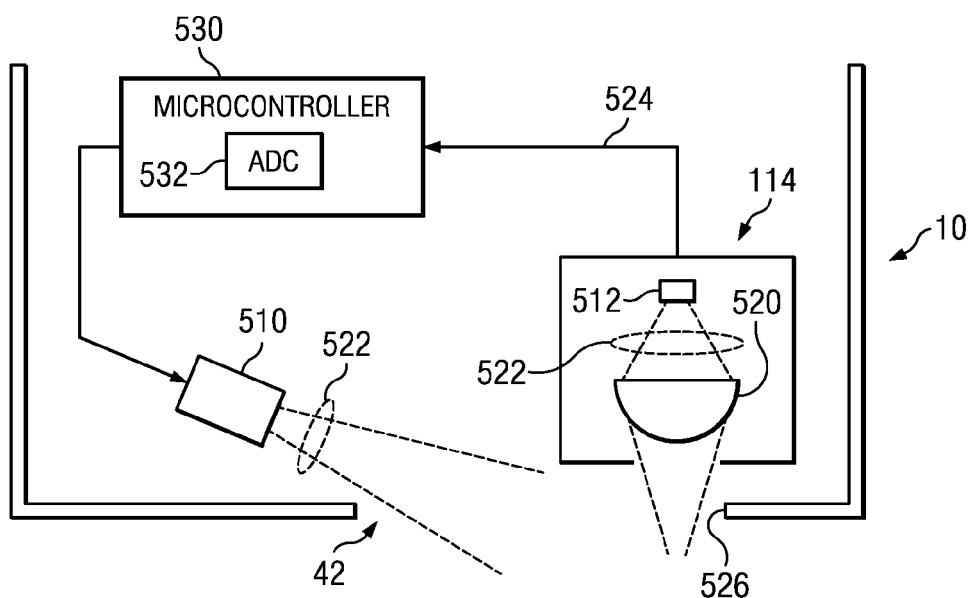
FIGS. 48-49 illustrate an example optical eye safety sensor, according to certain embodiments.

FIG. 48 illustrates an example optical eye safety sensor 114, according to certain embodiments. Optical eye safety sensor 114 may include a light source 510, a light detector 512, detector optics 520, relay optics 522 (in some embodiments), and a microcontroller 530.

Light source 510 may be a light-emitting diode (LED) or any other suitable light source. Light source 510 may be selected for showing fine details in the surface of human skin. Thus, a wavelength may be selected that penetrates a relatively shallow depth into the skin before being reflected. For example, light source 510A may be a blue LED having a wavelength of about 560 nm, or a red LED having a wavelength of about 660 nm, or an infrared LED having a wavelength of about 940 nm. Red or infrared wavelength LEDs are relatively inexpensive and work well in practice. Alternatively, a semiconductor laser could be used.

Light detector 512 may be a photodiode, phototransistor, or other light detector. In some embodiments, a phototransistor has sufficient current gain to provide a directly usable signal, without requiring additional amplification. Light detector optics 520, e.g., a half-ball lens, may be coupled to or carried with light detector 512. Light detector optics 520 may be configured to allow light detector 512 to "view" a target surface location.

Further, in some embodiments, sensor 114 may include relay optics 522 for relaying light from light source 510 and/or relay optics 522 for relaying reflected light to detector 512. Relay optics 522 may be used to relay light for any desired distance, such that one, some, or all of light source 510, detector optics 520, and/or detector 512 may be located at any desired distance from an aperture 526 in housing 24 that may be configured to be positioned on or near the skin surface 32 during use. Also, microcontroller 530 and/or other electronics associated with sensor 114 may be located at any distance from aperture 526 and/or from the other components of sensor 114 (e.g., light source 510, detector 512, detector optics 520, and optional relay optics 522). In some embodiments, locating components of sensor 114 away from aperture 526 may reduce or minimize the space occupied by sensor 114 at treatment tip 42 of device 10, which may allow for a reduced or minimized size of treatment tip 42, which may be desirable or advantageous.

In other embodiments, components of sensor 114 may be located near aperture 526 (e.g., in the treatment tip 42 of device 10), such that relay optics 520 are not included.

Light source 510 may be oriented to illuminate a surface (e.g., skin surface 32) at a very low angle of incidence (e.g., 0 shown in FIG. 49 may be between about 5 and 40 degrees), while detector 512 may be aligned at a normal or near-normal angle of incidence relative to the illuminated surface.

Microcontroller 530 may be configured to drive light source 510 (e.g., an LED) with a direct or modulated current, record a signal 524 from detector 512 using an integrated ADC 532, and analyzes the amplitude of the recorded detector signal 524 to determine if the surface below detector 512 is skin 32 or cornea 500.

The signal 524 from detector 512 may be referred to as a "reflectance feedback signal." The amplitude of the reflectance feedback signal 524 corresponds to the intensity of reflected light from light source 510 received by detector 512: the more light from light source 510 that is reflected into detector 512, the higher the amplitude of reflectance feedback signal 524. As discussed below, due to the configuration of light source 510 and detector 512, skin (which is relatively diffuse) reflects more of light from light source 510 into detector 512 than the cornea (which is relatively specular). Thus, microcontroller 530 may analyze the amplitude of reflectance feedback signal 524 (e.g., using threshold or window comparisons) to determine whether the surface below detector 512 is skin 32 or cornea 500.

Signals from microcontroller 530 indicating whether a treatment window 44 of device is located above skin or the cornea may be used by control systems 18 for controlling one or more controllable operational parameters of device 10.

For example, treatment (e.g., delivery of radiation to a treatment area 40) may be initiated, such as to begin a treatment session, or re-initiated after an interruption during a treatment session if microcontroller 530 detects a "skin presence," e.g., by determining that reflectance feedback signal 524 is above a predefined skin/cornea threshold or within a predefined reflectance window corresponding with skin. In such situation, control systems 18 may enable or power on treatment radiation source 14 (or control other aspects of device 10) to begin radiation delivery to the treatment area 40. The treatment may continue as long as microcontroller 530 continues to detect a skin presence. The treatment may be interrupted upon detection of a "possible cornea presence" or upon other treatment interrupting events.

If microcontroller 530 determines that reflectance feedback signal 524 is below the predefined skin/cornea or outside the reflectance window corresponding with skin, microcontroller 530 may detect a "possible cornea presence" (which is essentially a detection of a non-skin surface, which could be a cornea, other non-diffuse surface, or lack of a target surface, for example). Control systems 18 may disable treatment radiation source 14 (or control other aspects of device 10) in response to a possible cornea presence detected by microcontroller 530, in order to prevent a possible unintended eye exposure (and possible eye damage).

Figure 49:
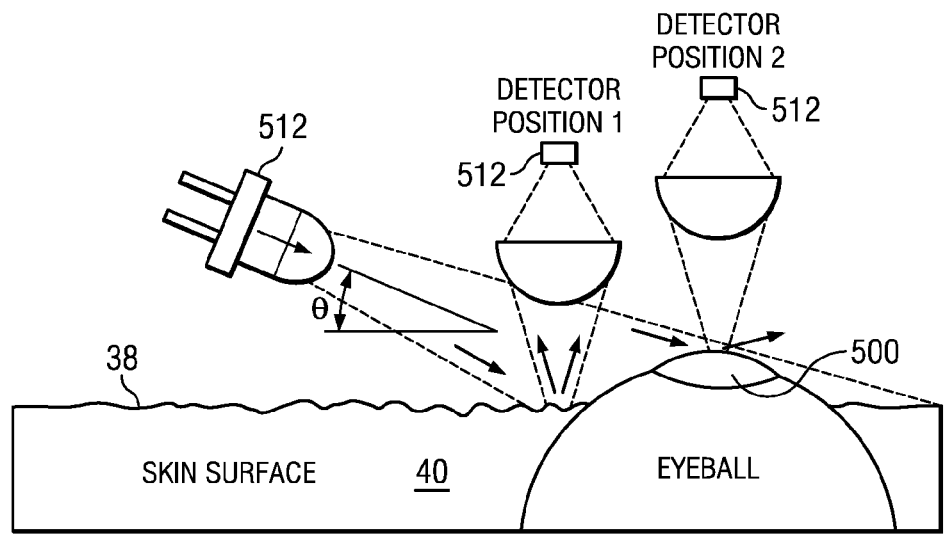
Figure 50A:
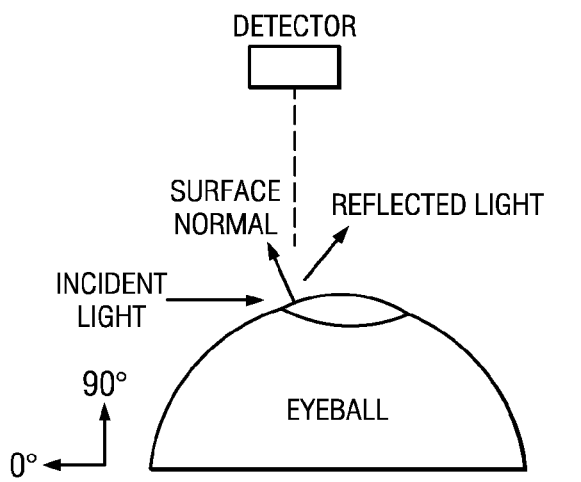
FIGS. 50A and 50B illustrate the local surface normal directions for example corneas of different shapes.
Figure 50B:
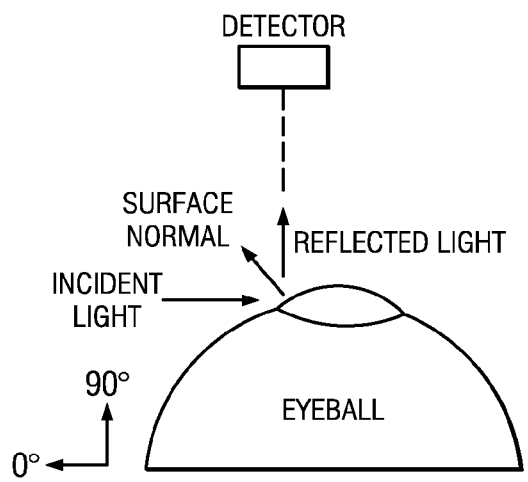

The operation of sensor 114 is described below with reference to FIGS. 49-50B. FIG. 49 illustrates light source 510 and two different positions of detector 512. FIGS. 50A and 50B illustrate the local surface normal directions for example corneas of different shapes.

Detector 512 receives a larger amount of reflected light (and thus generates a larger amplitude of signal 524) from diffuse surface materials, due to light scattering, than from smoother, more specular reflection materials. Skin is relatively diffuse, while the corneal surface is generally smooth and specular, such that the corneal surface has a much lower diffuse component of reflection than the skin. This difference can be used to determine whether detector 512 is positioned over an area of skin 32 or over the cornea 500.

This technique of discriminating between diffuse and specular materials using a single beam source 510 and single detector 512 may assume that the angles between the target surface normal and both the beam source 510 and detector 512 are known at least to an extent. In particular, the angles at which beam source 510 and detector 512 are aligned relative to the target surface may be selected such that the reflectance feedback signal 524 can be reliably used to distinguish reflection off the skin from reflection off the cornea, for a known range of corneal curvatures, as discussed below with respect to FIGS. 50A and 50B.

In general, the local surface normal vector of a surface (e.g., skin or corneal surface) will vary relative to a larger-scale average surface normal, depending on the local curvature of the surface. For example, near the edge of the cornea, the local surface normal will be at least several degrees offset from the normal vector at the center of the cornea, because the cornea is a curved surface.

Assume a light beam source illuminates a surface at an incidence of near-grazing (~0 degrees) and a detector views this surface at near normal incidence (~90 degrees). For less curved surfaces, the local surface normals are relatively close to 90 degrees, as shown in FIG. 50. In an extreme case shown in FIG. 50B, in which curvature provides a local surface normal of 45 degrees, a specular reflection propagates directly into the detector. It may be assumed for the purposes of sensor 114 that the exposed corneal surface forms an angle of less than 45 degrees with the larger surface normal of the face (i.e., skin adjacent the eye), such that a direct specular reflection from beam source to detector does not occur for any practical configuration of sensor 114/device 10 relative to the face. It is also known that for a normal eye, the most extreme angle near the corneal edge is less than 40 degrees. (See, e.g., James D. Doss, "*Method for Calculation of Corneal Profile and Power Distribution*", Arch Ophthalmol, Vol. 99, July 1981). Moreover, this angle quickly decreases to near 20 degrees within 60% of the central cornea region, i.e., the curvature is not large near the cornea center. Therefore, for the central 60% cornea region, the specular reflection from the cornea will not be intercepted by the detector with a large margin.

Thus, assuming light source 510 is arranged at a sufficiently low angle of incidence (e.g., θ shown in FIG. 49 between about 5 and 40 degrees), for all practical cases the cornea will not reflect the light from light source 510 directly into detector 512. Thus, for all practical cases, the cornea will reflect less light from light source 510 into detector 512 than will the skin. Thus, for practical cases, the cornea can be distinguished from skin, assuming the proper signal amplitude thresholds are utilized by microcontroller 530. Thus, to summarize, assuming the proper orientation of light source 510 and detector 512, as well as the proper selection of threshold(s) for comparing the amplitude of reflectance feedback signal 524, sensor 114 is able to reliably discriminate between the skin and the cornea, especially for the central cornea region which may be the most important for vision.

It has been shown experimentally that the scattering coefficient of skin dermis $\mu m_{s\_skin}$ is substantially greater than that of the cornea $\mu m_{s\_cornea}$. In particular, the scattering coefficient of skin dermis $\mu m_{s\_skin} \approx 60$ $cm^{-1}$ for 500-nm wavelength (see Steven L. Jacques, "*Skin Optics*", *Oregon Medical Laser Center News*, January 1998), whereas the scattering coefficient of skin dermis $\mu m_{s\_cornea} \approx 10$ $cm^{-1}$ for 500-nm wavelength (see Dhiraj K. Sardar, "*Optical absorption and scattering of bovine cornea, lens, and retina in the visible region*", *Laser Med. Sci.*, 24(6), November 2009). Based on these respective scattering coefficients, the expected diffused reflectance of the cornea is about 8%, while the expected diffused reflectance for a typical Fitzpatrick Type I to VI skin ranges from 70% to 10% respectively. Thus, for most skin types, the reflectance contrast is large enough discriminating the cornea from the skin, again assuming the proper comparison thresholds or windows are utilized by sensor 114.

Multi-Sensor Eye Safety System

In some embodiments, device 10 includes a multi-sensor control/safety system that includes one or more eye safety sensor 114 and one or more skin contact sensors 104.

Figure 51:
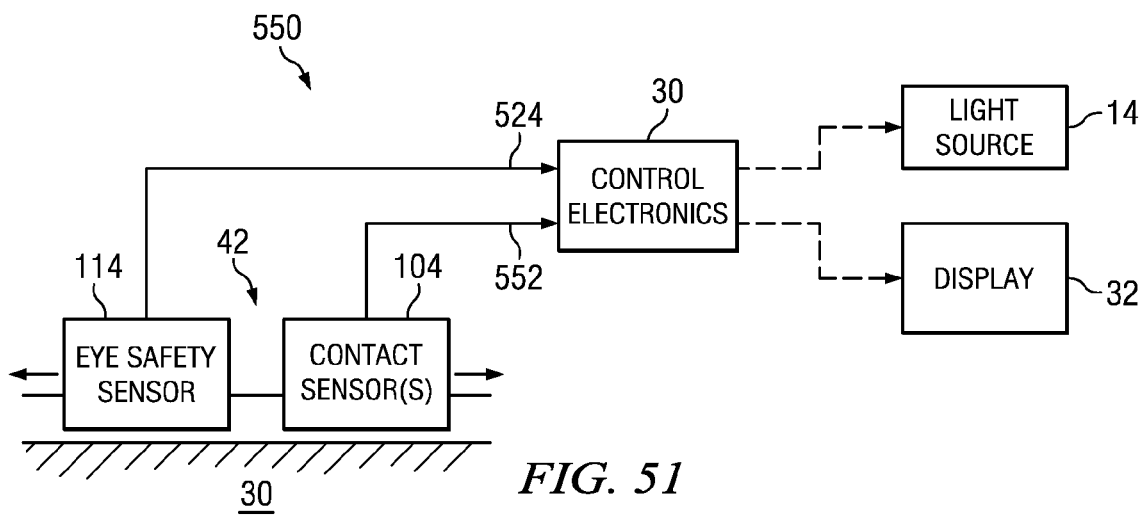
FIG. 51 illustrates an example multi-sensor control/safety system that includes one or more eye safety sensors and one or more skin contact sensors arranged on or near device application end, according to certain embodiments.

FIG. 51 illustrates an example multi-sensor control/safety system 550 that includes one or more eye safety sensor 114 and one or more skin contact sensors 104 arranged on or near device application end 42. System 550 combines the functionality of eye safety sensor 114 and skin contact sensor(s) 104 to provide more reliable and/or redundant eye safety functionality as compared to eye safety sensor 114 or skin contact sensor(s) 104 acting alone.

System 550 may configured to control device 10 (e.g., turn treatment radiation source 14 on/off) based on independent determinations made by eye safety sensor 114 and skin contact sensor(s) 104, in any suitable manner. The independent determinations made by eye safety sensor 114 and skin contact sensor(s) 104 may be based on comparisons of signals detected by such sensors to respective thresholds, referred to herein as "independent determination thresholds."

For example, system 550 may trigger a control signal to turn on treatment radiation source 14 if either (a) eye safety sensor 114 determines a "skin presence" (discussed above), independent of any determinations or signal analysis by contact sensor(s) 104, or (b) all contact sensors 104 determine a contact status with the skin, independent of any determinations or signal analysis by eye safety sensor 114. Thus, system 550 may trigger a control signal to turn off treatment radiation source 14 only if both (a) eye safety sensor 114 determines a "possible cornea presence" (discussed above), independent of any determinations or signal analysis by contact sensor(s) 104, and (b) at least one contact sensor 104 determines a non-contact status with the skin, independent of any determinations or signal analysis by eye safety sensor 114.

Alternatively, system 550 may trigger a control signal to turn on treatment radiation source 14 only if both (a) eye safety sensor 114 determines a skin presence (discussed above), independent of any determinations or signal analysis by contact sensor(s) 104, and (b) all contact sensors 104 determine a contact status with the skin, independent of any determinations or signal analysis by eye safety sensor 114. Thus, system 550 may trigger a control signal to turn off treatment radiation source 14 if either (a) eye safety sensor 114 determines a possible cornea presence, independent of any determinations or signal analysis by contact sensor(s) 104, or (b) any contact sensor 104 determines a non-contact status with the skin, independent of any determinations or signal analysis by eye safety sensor 114.

Alternatively or in addition, system 550 may be configured to control device 10 (e.g., turn treatment radiation source 14 on or off) based on inter-dependent analysis of signals from eye safety sensor 114 and signals from skin contact sensor(s) 104. For example, system 550 may utilize algorithms that analyze signals detected by eye safety sensor 114 (e.g., reflectance feedback signal 524 from detector 512) and signals detected by contact sensor(s) 104 (e.g., signal 552 detected by contact sensor(s) 104) to determine whether to trigger a particular control signal. For example, such algorithms may incorporate thresholds that are lower than the independent determination thresholds discussed above. Such thresholds are referred to herein as "inter-dependent sensor analysis thresholds."

To illustrate by example, system 550 may specify the following independent determination thresholds:

(a) 10 mV eye safety threshold: eye safety sensor 114 determines a possible cornea presence if the amplitude of reflectance feedback signal 524 falls below 10 mV, and (b) 50 pF contact sensor threshold: contact sensor 104 determines a non-contact status if the amplitude of contact sensor signal 552 falls below 50 pF.

Further, system 550 may specify the following inter-dependent sensor analysis thresholds:

(a) 15 mV eye safety threshold for reflectance feedback signal 524, and (b) 70 pF contact sensor threshold for signal 552.

System 550 may utilize an algorithm 154 that incorporates the inter-dependent sensor analysis thresholds (15 mV and 70 pF). For example, an algorithm may specify a control signal to turn off treatment radiation source 14 if both (a) reflectance feedback signal 524 falls below 15 mV and (b) contact sensor signal 552 falls below 70 pF.

As another example of controlling device 10 based on inter-dependent analysis of signals from eye safety sensor 114 and signals from skin contact sensor(s) 552, an algorithm 154 may calculate an index, referred to herein as an "eye safety factor index," or ESF index from reflectance feedback signal 524 and contact sensor signal 552. The algorithm may weight reflectance feedback signal 524 and contact sensor signal 552 in any suitable manner. An example algorithm is provided as equation (1):

$$\text{ESF index} = \text{signal 524 amplitude}*W1 + \text{signal 552 amplitude}*W2 \quad (1)$$

where W1 and W2 represent any suitable constants (including 0).

Another example algorithm is provided as equation (2):

$$\text{ESF index} = (\text{signal 524 amplitude} + C1)*(\text{signal 552 amplitude} + C2) \quad (2)$$

where C1 and C2 represent any suitable constants (including 0).

Any other suitable algorithms may be used for calculating an ESF index based on reflectance feedback signal 524 and contact sensor signal 552.

ESF index may then be compared to a predefined threshold to determine whether to trigger a particular control signal (e.g., to turn off treatment radiation source 14), or compared to multiple different predefined thresholds for triggering different control signals. Such algorithms (using the same or different threshold values) may be used for triggering any suitable control signals, such as control signals for turning on treatment radiation source 14, turning on treatment radiation source 14, changing the current treatment mode, or adjusting any controllable operational parameter of device 10.

Figure 52:
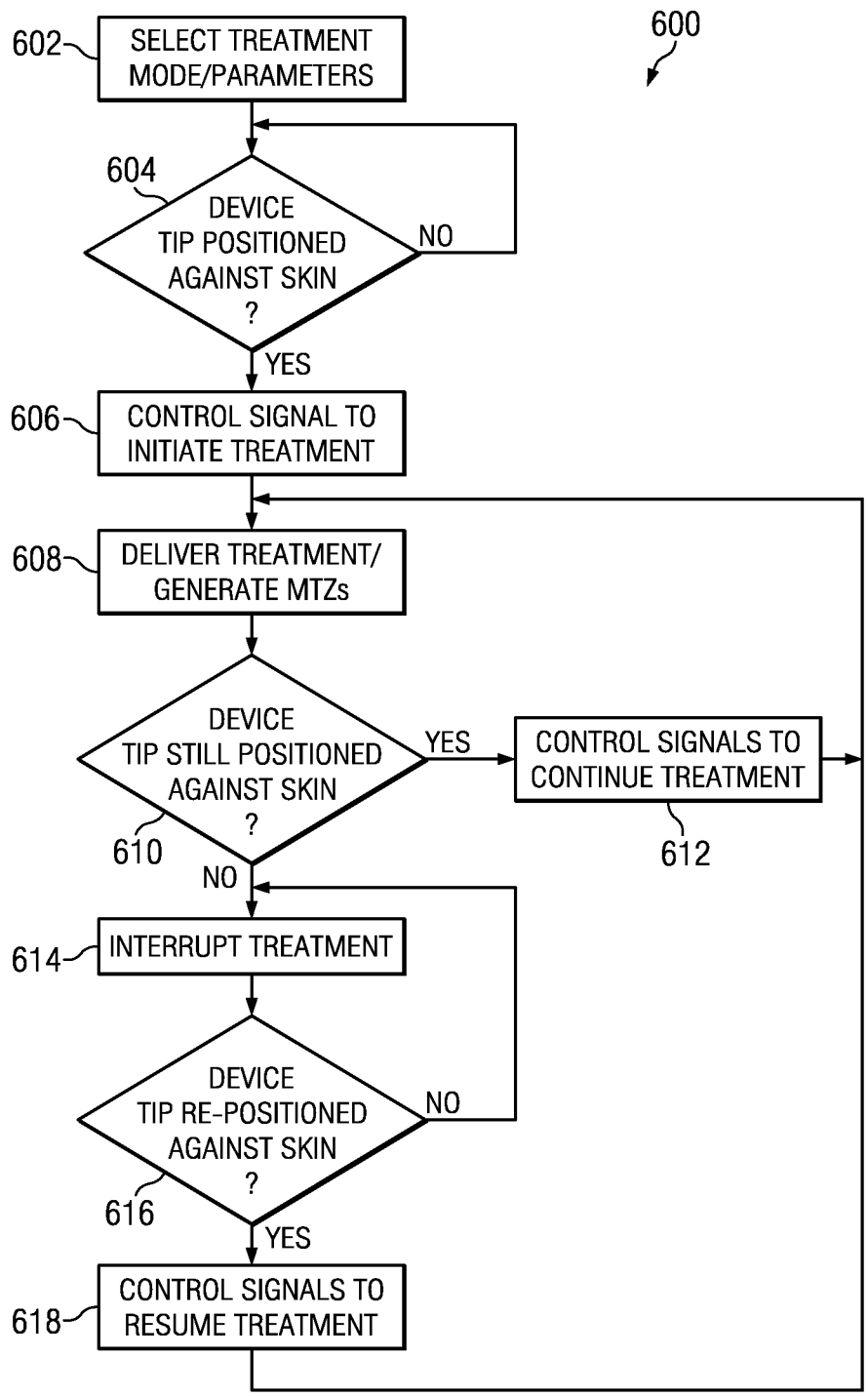
FIG. 52 illustrates an example method for controlling a device using a multi-sensor control/safety system, according to certain embodiments.

FIG. 52 illustrates an example method 600 for controlling device 10 (e.g., controlling treatment radiation source 14) using a multi-sensor control/safety system 550, according to certain embodiments. At step 602, a user prepares for a treatment session by selecting a treatment mode and/or other treatment parameters, and places the application end 42 of device 10 against the skin.

At step 604, system 550 determines whether the application end 42 is correctly positioned against the skin for treatment, e.g., using any of the techniques discussed above or any other suitable technique.

If system 550 determines that the application end 42 is correctly positioned against the skin for treatment, system 550 may generate a control signal for beginning a treatment session automatically or upon a defined user input (e.g., pressing a treatment button), as indicated at step 606. Control systems 18 may also generate feedback to the user indicating that treatment has been initiated or that treatment is ready for initiation upon the defined user input (e.g., pressing a treatment button).

Device 10 may then activate radiation source(s) 14 to deliver beams 60 to the treatment area 40 to generate treatment spots 62, as indicated at step 608. The user may operate device 10 in a gliding mode or a stamping mode, depending on the configuration and/or selected treatment mode of device 10.

During the treatment, system 550 continually or repeatedly determines whether the application end 42 is still correctly positioned against the skin for treatment, as indicated at step 610. As long as system 550 determines that application end 42 is correctly positioned against the skin for treatment, system 550 may continue to generate control signals for continuing the treatment session (i.e., such that control systems 18 continues to provide beams 60 to generated treatment spots 62 in treatment area 40), as indicated at step 612.

However, during the treatment, if system 550 determines that application end 42 is not correctly positioned against the skin for treatment (e.g., if system 550 determines that application end 42 is located over the cornea or moved out of contact with the skin), system 550 may generate a control signal for automatically stopping or interrupting the treatment session, e.g., by turning off or disabling treatment radiation source 14), as indicated at step 614. Control systems 18 may also generate feedback, e.g., audible or visual feedback, to the user indicating the status of device 10. For example, control systems 18 may provide general feedback indicating that the treatment has been stopped or interrupted, or may provide more specific feedback indicating the reason that the treatment has been stopped or interrupted, such as feedback distinguishing between eye detection, non-contact detection, and device malfunction, for example.

System 550 may continue to monitor the positioning of application end 42 at step 616. If system 550 determines that application end 42 has again become correctly positioned against the skin for treatment, system 550 may resume the treatment session, e.g., by generating a control signal to resume treatment (e.g., by turning on treatment radiation source 14), as indicated at step 618, and resuming the generation of treatment spots 62 in the skin, as indicated by the method returning to step 608.

The treatment session may end upon reaching a treatment delimiter (such as discussed above regarding FIG. 48), or after a predefined time, or based on any other parameters defining the treatment session. It should be understood that this example and FIG. 52 can apply to sensors other than contact sensor in a similar manner.

Calibration of Eye Safety Sensor

Figure 53:
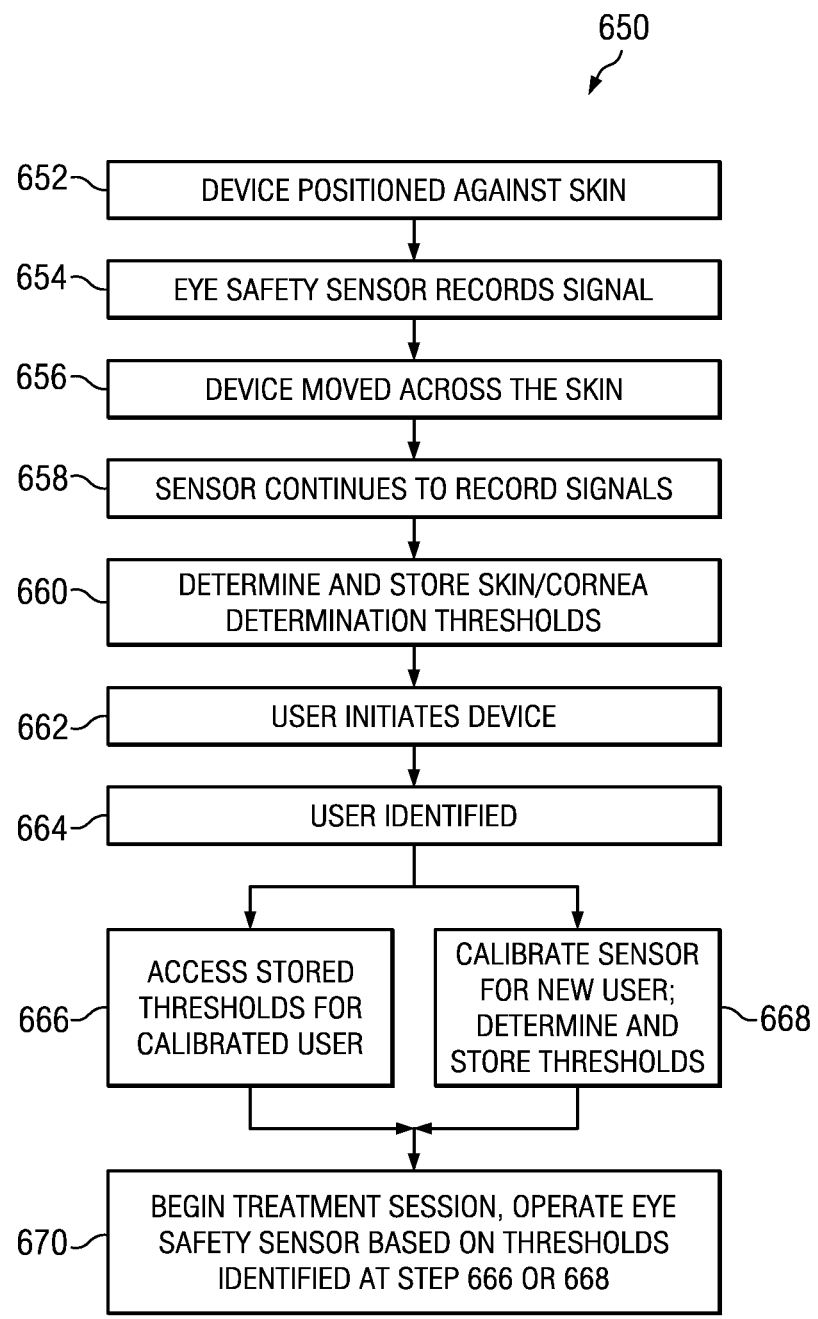
FIG. 53 illustrates an example method for calibrating an eye safety sensor for one or multiple users, according to certain embodiments.

In some embodiments, eye safety sensor 114 can be individually calibrated to the current user of device 10. FIG. 53 illustrates an example method 650 for calibrating eye safety sensor 114 for one or multiple users. A calibration process is performed at steps 652-660. At step 652, a user positions the application end 42 of device 10 against the user's skin, e.g., upon instruction from device 10. Device 10 may instruct the user to position application end 42 against a certain part of the body, e.g., the face or back of the hand. Sensor 114 is activated and records a reflectance/remittance feedback signal 524 at step 654. At step 656, the user may move the application end 42 of device 10 across the skin, e.g., upon instruction from device 10. Sensor 114 may continue to record reflectance feedback signal 524 at various locations of application end 42 on the skin, at step 658.

At step 660, microcontroller 530 may analyze signal 524 recorded at steps 654, 658 to calibrate sensor 114. For example, microcontroller 530 may execute one or more algorithms to determine one or more appropriate threshold values (e.g., threshold voltages) for distinguishing between skin and the cornea, e.g., for determining a "skin presence" or "possible cornea presence," as discussed above. Such threshold values may be stored by sensor 114 or control systems 18.

At step 662, the same user or a different user may initiate device 10 for a treatment session. The user may identify him or herself via a user interface 18, e.g., by scrolling and selecting from a list of names, or entering a new name, at step 664. Device 10 may then determine whether eye safety sensor 114 has been calibrated for that user, and if so, access the skin/cornea determination thresholds stored for that user, at step 666. If the user is a new user or eye safety sensor 114 has not been calibrated for that user, device 10 may calibrate sensor 114 for that user to determine and store skin/cornea determination thresholds for that user, at step 668 (e.g., by leading the user through the calibration process of steps 652-660).

After the skin/cornea determination thresholds for the user have been accessed (or in the case of a new user, determined and stored), the user may select various operational parameters and begin a treatment session using device 10. During the treatment session, at step 670, eye safety sensor 114 may continually or repeatedly monitor the surface under application end 42 using the user-specific thresholds accessed at step 666 or 668.

In other embodiments, device 10 may require eye safety sensor 114 to be recalibrated before each treatment session.

Dual-Function Sensors

In some embodiments, in addition to providing eye safety functionality, eye safety sensor 114 may also be used as a displacement sensor, operating in a similar manner as discussed above regarding single-pixel displacement sensor 100A, 100B, or 100C shown in FIGS. 37-39. For example, the functionality of eye safety sensor 114 and displacement sensor 100A/100B/100C may be integrated into a single sensor 100/114. Thus, a single light source and single detector may be used to provide both the eye safety and displacement monitoring functions described above. The integrated displacement/eye safety sensor 100/114 includes one or more microcontrollers or other processors for providing the functionality of both sensors.

In other embodiments, device 10 may include both eye safety sensor 114 and one or more displacement sensors 100 (e.g., one or more single-pixel displacement sensors 100A/100B/100C and/or one or more multi-pixel displacement sensors 100D), wherein eye safety sensor 114 provides (in addition to its eye safety functionality) device displacement monitoring functionality to supplement or provide a backup to the displacement sensor(s) 100A/100B/100C.

Additional Embodiments and Features

Figure 54:
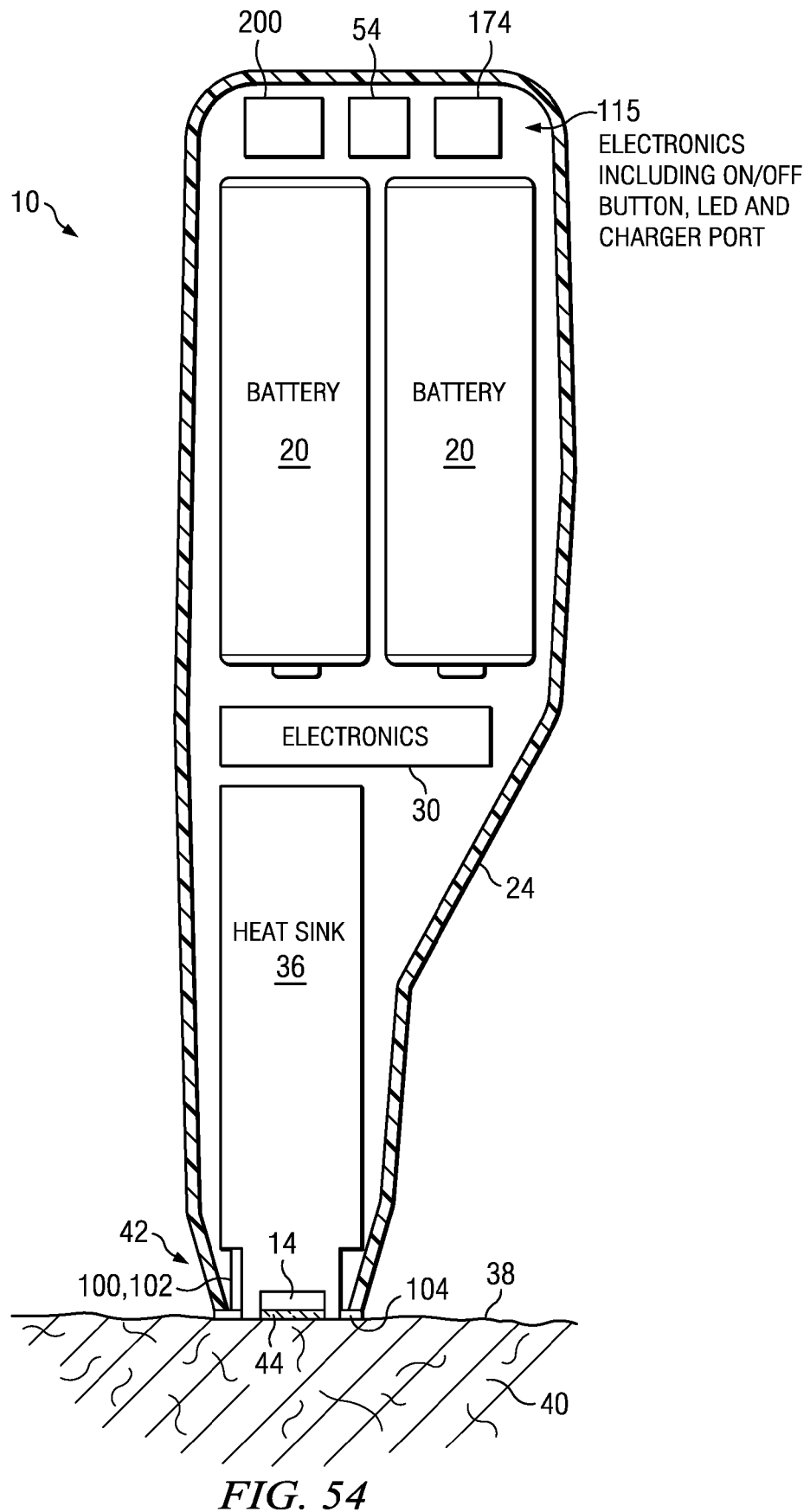
FIG. 54 shows another embodiment of a radiation-based treatment device.
Figure 55:
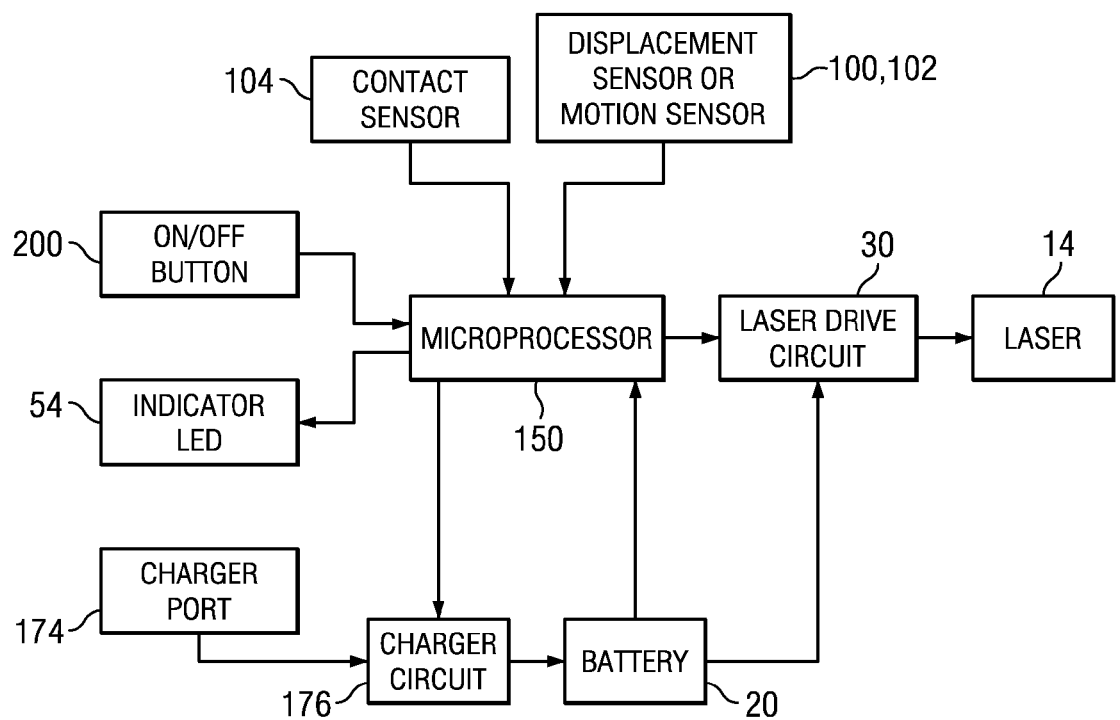
FIG. 55 illustrates an example operational schematic of the example device shown in FIG. 54, according to certain embodiments.

Another example embodiment of device 10 is shown in FIGS. 54 and 55, and discussed below.

FIG. 54 shows an embodiment of device 10 that may be approximately 12 cm long, having a generally rectangular cross-section in the upper portion of approximately 2 cm×4 cm, and a nearly square cross-section in the lower portion of about 2 cm×2 cm. These dimensions and shapes are exemplary only, to give a sense of the scale of the device and its comfort as a hand-held device, and such dimensions and shapes are not intended to be limiting in any manner.

The upper portion of housing 24 may house, for example, two AA-size lithium polymer batteries 20, and user interfaces 28 including an on/off button 200 and operational indicator 54 such as an LED, as well as a charger port 174 for recharging the batteries 20. The middle region of the device may house control electronics 30 for controlling the energizing of a laser 14 (which may include, e.g., between one and four edge emitting laser diodes, which are referred to hereinafter simply as laser 14 for clarity) and responsive to a contact sensor 104 and either a displacement sensor 100 or a motion/speed sensor 102, depending on the particular embodiment. This location of electronics 30 allows for the electronics 30 to be thermally coupled to a heat sink 36, in this case a thermal mass (for example, a cylinder of copper) located in the lower portion of the device.

In an embodiment, to prevent the laser 14 from overheating, the laser may be arranged in direct thermal contact with the thermal mass heat sink 36. During operation, the waste heat from the edge emitting laser diode 14 is conducted into the mass 36. For example, the thermal mass 36 can be machined out of copper in such a way that the laser 14 is pressed into an opening in the copper cylinder, and in some embodiments the mass 36 can serve as one electrical conduit for connecting the laser drive circuit 30 to the edge emitting laser diode 14.

The displacement sensor 102 or motion/speed sensor 102 may be located very close to the treatment tip 42 of the housing 24, generally adjacent to the edge emitting laser diode 14 as shown in FIG. 54. The contact sensor 104 may also be located at or near the device tip 42, and for example may comprise a capacitive sensor partly or wholly surrounding a window 44 through which a laser beam or beams 60 are delivered toward the skin 40, although mechanical sensors are also acceptable in some embodiments. The window 44 may be selected from a group comprising sapphire, quartz, diamond, or other material transparent at the frequency of the edge emitting laser diode and having a good thermal coefficient. In some embodiments, the window 44 is placed in contact with the skin surface 38 during treatment.

Referring next to FIG. 55, an example operational schematic of device 10 of FIG. 54 is shown in block diagram form. At least one microprocessor 150 receives power from batteries 20 or other power supply. In embodiments in which rechargeable batteries are used, a charger circuit 176 and charging port 174 may be provided, with the charging port 174 also receiving control signals from processor 150 to prevent overcharging and detect operational errors.

On on/off button 200 may enable operation of the circuitry, such that when power is applied to the microprocessor 150, an indicator light or LED 54 is illuminated. A contact sensor 104 detects contact with a user's skin, as discussed above, while either a displacement sensor 100 or a motion/speed sensor 102 detects displacement or motion of the device across the skin at a displacement or rate deemed sufficient to prevent multiple firings of laser 14 in too-close proximity to one another, thus preventing overlap of successive treatment spots 64. The contact sensor 104 and displacement sensor 100 or motion/speed sensor 102 may provide input to the processor 150, which allows the processor to energize a laser drive circuit 30 safely and effectively. When permitted by the processor 150, the laser drive circuit 30 energizes edge emitting laser diode 14, which causes a pulsed beam 60 to be emitted through the outlet window 44 described above.

In one embodiment, the non-ablative fractional device 10 may incorporate, for example, a mid-infrared edge emitting laser diode in the wavelength range of 1.4-1.6 microns, such as those available from SemiNex Corporation (Peabody, Mass.). These very small (4 mm×7 mm×8 mm) laser devices produce about 6 watts of laser power. Device 10 may set a pulse duration of about 5 ms, which may produce about 30 mJ of energy per pulse. The laser can operate at a pulse repetition rate of about 20 Hertz, for example. According to these example parameters, the diode voltage may be about 1.7 volts at a current of about 10 amperes, resulting in an efficiency of about 35%. The output wavelength may be, for example, 1.47 microns (SemiNex Part No. C-1470-6-95).

Beam propagation according to such embodiments may be simpler and more reliable than in conventional devices. As described above, the direct laser output of a typical diode laser is highly divergent in the fast axis, with considerably lower divergence in the slow axis. In certain conventional devices, a cylindrical microlens or other optic may be placed in the optical path, very close to the emitter surface (or "facet"), to collimate or reduce the divergence of the beam in the fast axis. Further in the optical path, a second cylindrical lens or other optic may be positioned orthogonal to the first lens, to collimate or reduce the divergence of the beam in the slow axis. This relatively complex arrangement is used in certain conventional devices because it allows the beam to be propagated through various beam-scanning optics. However, in such conventional devices, careful and laborious (and costly) positioning of the lenses or other optics may be necessary to bring the beam to focus on the skin at the output window, wherein the emitter facet is approximately 1 micron by 100 microns, and the exit window has an area of one square centimeter or more.

In contrast, certain embodiments disclosed herein eliminate the microlenses or other optics used in such conventional devices, and instead locate the diode laser emitter facet (i.e., emitter surface) very close to the skin surface (e.g., with only a thin window between the diode laser emitter facet and the skin, and rely on the divergence and propagation characteristics of the unmodified beam 60 to create an appropriately sized treatment spot 62 and MTZ 64 on the skin. For example, a 1-micron by 95-micron beam with divergence of about 28 deg FWHM by about 6 deg FWHM, respectively, may expand to an approximately circular beam of about 120 microns at a distance of 240 microns from the emission facet. Using an approximately 0.14 mm thick window with its input face about 100 microns from the emitter facet, and its output face touching the skin at a distance of about 240 microns from the emitter facet may produce a treatment spot 62 on the skin surface of about 120 microns in diameter. With a device glide speed of about 2 cm/s and a 5-ms pulse duration, the treatment spot 62 becomes an oval of about 120 μm by 220 μm in diameter.

While some embodiments omit lenses of any type (as discussed above), in some embodiments device 10 may include a simple lens for beam shaping while still benefiting from various advantageous aspects discussed above. For example, if a larger treatment spot 62 or MTZ 64 is desired, a diverging lens can be used; or, alternatively, the edge emitting laser diode 14 can be moved slightly further from window 44, for example by an additional 100 microns, allowing a longer propagation path for the beam 60 before it reaches the skin. If a smaller treatment spot 62 or MTZ 64 is desired, a simple converging lens can be used. Utilizing example treatment parameters described more fully below, the percentage of area treated may be between about 1% and about 10%, e.g., about 5% of the skin surface if the treatment spot diameter is about 65 microns, and between about 10% and about 30%, e.g., about 20% of the skin surface if the treatment spot diameter is about 130 microns, when, for example, device 10 is used daily for about one month.

In some embodiments, and for particular operational parameters, the beam may have an elliptical shape of approximately 150 μm by 250 μm at a depth into the skin of about 260

µm, assuming the device is held stationary on the skin. When the device is glided across the skin, this elliptical shape becomes a roughly circular zone of about 250 µm in diameter. This re-shaping of the beam at depth occurs due to the movement of the device across the skin. In some embodiments, the user may be instructed to move device 10 in a generally side-to-side or serpentine manner, e.g., as shown in FIG. 8C, 8D, 8F, or 8G, for example.

The simplicity of certain embodiments disclosed herein may reduce or minimize the electrical load on the battery/batteries 20, which may allow for sufficient charge from a single AA-sized battery. To provide a peak current requirement of, for example, 10 amps, two AA-sized batteries may be used in some embodiments. Operation of an example embodiment of device 10 at, for example, 6 watts of optical output power for 120 seconds may requires a charge of only 34 mAh, whereas a typical single AA-sized lithium polymer battery has a charge of about 600 mAh. For example, an IMR 14500 rechargeable battery available from www.lighthound.com has a continuous discharge current capability of 3 amps, or 6 amps for two batteries in parallel. For an example laser pulse duration of 5 ms (and an example duty cycle of about 10%), this battery pair can readily produce current pulses of 10 amps or more. A very low current battery-charger port 174 may be included at the back end of device 10, as shown in FIG. 54.

Some embodiments of device 10 may include a motion/speed sensor 102 comprising an accelerometer for determining motion of the device 10. However, the operation of the accelerometer in device 10 may differ significantly from those found in the conventional devices. For an effective operation of certain embodiments of device 10, absolute location relative to the prior laser pulse is not important as long as the new location is at a location different from the prior laser pulse. Thus, in such embodiments, as long as a detectable signal from the accelerometer confirms that device 10 is undergoing acceleration, and contact sensor 104 confirms that device 104 is in contact with the skin 40, the next laser pulse can be at any location. One example of a suitable accelerometer is the LIS305DL available from ST Microelectronics (Santa Clara, Calif.), which is a three axis linear accelerometer measuring about 3 mm by 5 mm by 0.9 mm in size and can be readily mounted by any conventional means at or near the tip 42 of device 10 and electrically connected to processor 150. In an alternative embodiment, the motion/speed sensor can be a vibration and tilt sensor such as a SignalQuest SQ-MIN-200. Other embodiments of device 10 include a displacement sensor 100 (e.g., as discussed above in greater detail) instead of a motion/speed sensor 102 or accelerometer.

To reduce or minimize the size and power consumption of device 10, some embodiments use a thermal mass 36 to mitigate temperature rise in the device. The mass 36 can be, for example, solid copper which has a volumetric heat capacity of 3.45 joules per centimeter cubed per degree centigrade. For an example embodiment operating with two lithium AA batteries operating at 3.5 V and an average current of 1 A (e.g., 10 A at 10% duty cycle) for two minutes, the total heat generated is slightly over 400 joules. Certain edge emitting laser diodes can operate safely with a temperature rise of about 20° C. or more; thus the volume of copper required to effect a thermal mass temperature rise of 20° C. is about 6 cubic centimeters. This corresponds to a 14 mm diameter rod about 4 cm in length, or approximately the diameter of an AA battery with slightly shorter length. Alternatively, the mass 36 can comprise a sealed thermally conductive cylinder or other shape container filled with a liquid such as water, or a phase change material such as a wax with a melting point of around 30° C.

In some embodiments, or for some patients, it may be desirable to cool or chill device 10, or at least thermal mass 36, before using device 10. For example, if mass 36 comprises a sealed container filled with water, freezing the water in the container can offer the ability to absorb substantially more energy without any temperature increase during the melting process.

By locating the laser control electronics 30 at the opposite end of the copper cylinder from the laser 14, the waste heat from electronics 30 (included in the above total) is also deposited in the copper mass 36. Once the device thermal mass 36 has reached approximately 40 deg C. (or other predefined temperature), the microprocessor 150 may prevent further operation of device 10 until room temperature is once again established in the thermal mass 36.

In a particular embodiment, device 10 may be designed to produce a 30-mJ pulse in 5 ms, forming a treatment spot 62 of about 120 µm by 220 µm at the skin surface. This energy is sufficient to produce denatured skin to a depth of at least 250 µm, which is generally comparable to certain office-based fractional treatment devices. An embodiment of device 10 configured for non-ablative fractional treatment may be used in the following manner, as an example. The on/off button 200 is pressed to turn the device on. The LED 54 is energized that is visible to the user, indicating that device 10 is ready for a treatment to be performed. The output window 44 of device 10 is then touched to the skin in the area to be treated, and device 10 is moved back and forth across the skin surface 38 at a manual glide speed generally in the range of about 1-2 cm/s, although in some applications the manual glide speed and/or the pulse repetition rate or duty cycle can vary considerably, as discussed further below. When contact with the skin surface 38 is verified by a contact sensor 104, and appropriate displacement or acceleration of tip 42 is sensed by displacement sensor 100 or motion/speed sensor 102 or accelerometer, pulsed laser beams 60 are emitted through the window 44 to the skin, and the LED 54 on device 10 flashes synchronously with the laser emission. If the tip 42 is (a) not moving; (b) failing to achieve sufficient displacement, motion, or acceleration across the skin; (c) moving too slowly or too quickly; (d) moving but undergoing no acceleration for an embodiment with an accelerometer; or (e) not in contact with the skin, device 10 may prevent pulsing of the laser. Condition (d) may occur if device 10 is moved in a straight line for, e.g., 5-10 centimeters at constant speed. If device 10 is moved back and forth across the skin, or varies moderately from a straight line, tip 42 will undergo acceleration at all times, thus enabling pulsing of the laser.

In some embodiments or applications, a manual glide speed of about 2 cm/s or 1 inch/s can be treat an area of about 20-30 cm² in a treatment session of about two minutes. This treatment area may be sufficient for coverage of the two periorbital regions when used as described above. At an example pulse repetition rate of about 10 Hz, roughly 50 MTZs are created in an area of roughly one square centimeter in about five seconds. In a month of once-daily treatments, about 1500 MTZs/cm² are created, which may be generally comparable to certain office-based systems.

After a predefined period of operation, e.g., two minutes, device 10 may automatically turn itself off, and may remain inoperable for some defined time period or until certain condition(s) are present, e.g., until the device heat sink 36 has returned to room temperature or other selected temperature, or until the battery 20 has substantially fully recharged, or both. In one embodiment, a full recharge of battery 20 takes approximately one hour, whereas heat sink 36 may return to room temperature more quickly.

In some alternative embodiments or application, device 10 can be operated at with somewhat faster manual glide speeds and higher pulse repetition rates to allow for greater areal coverage in a particular time period time. For example, for a pulse repetition rate of 20 Hz, operating for a period of two minutes, with a manual glide speed of about 2 cm/s, certain embodiments of device 10 can cover an area of 40-60 cm². When applied twice daily for thirty days, e.g., the total density of MTZs may be greater than or equal to the MTZ density achieved with certain office-based fractional treatment systems in a single monthly treatment, for example.

If greater coverage per unit of time is desired while maintaining a sufficient density of MTZs, the pulse repetition rate of the edge emitting laser diode may be increased in some embodiments, e.g., to approximately 30 Hz rather than 10 or 20 Hz, with a manual glide speed of about 2.5 cm/s, or about 1 inch/s. In such embodiments, approximately 300 MTZs may be deposited in an area of about 6 square centimeters, or about one square inch, for a density of about 50 MTZs/cm², but in about one-third the time compared to a pulse repetition rate of 10 Hz. This may allow treatment of each periorbital region in about 10-15 seconds, and a full face in about five minutes. Appropriate reductions can be made for automatic turn-off time after a cessation of motion; for example, within 30 ms of motion cessation for a 30 Hz device, versus 100 ms for a 10 Hz device. It will be appreciated that the foregoing duty cycles and pulse repetition rates are examples only, and significant variation is permitted in other embodiments.

In at least some embodiments of device 10, eye safety is assured based on contact sensor 104. Mid-infrared lasers are frequently referred to as "eye-safe" lasers, because light in the wavelength region of 1.4-1.6 microns is absorbed in the cornea and cannot pass through the vitreous humor of the eye. However, with sufficient fluence, one or more treatment spots could conceivably be created on the cornea unless appropriate safety measures are incorporated. Certain embodiments of device 10 (e.g., direct exposure embodiments using an edge emitting laser diode as the radiation source 14) utilize a rapidly diverging beam, such that the laser fluence at the cornea surface is insufficient to cause any damage unless the treatment tip 42 of device 10 is placed within approximately 5 mm of the cornea. Nonetheless, to ensure safe operation, certain embodiments include one or more contact sensors 104 at the device tip 42, which is/are connected to processor 150, to enable laser emission only when device tip 42 is in contact with the skin. Thus, for certain embodiments of device 10, the risk of eye injury may be substantially eliminated unless device 10 was placed directly on the eyeball, and then moved along the eyeball surface while maintaining contact. Other embodiments may alternatively, or in addition, include an eye safety sensor 114, e.g., as described above regarding FIGS. 48-51, which may further improve the eye safety aspect of device 10.

In some embodiments, e.g., where device 10 is configured for providing non-ablative fractional treatment, the operation of device 10 may allow for the introduction of topical agents through the stratum corneum and epidermis without providing an easy path by which undesirable bacteria can enter the body. It is well known that the uppermost layers of skin, namely the stratum corneum at the very top and epidermis immediately underneath, provide a strong and important "wall" protecting the underlying dermis and the blood vessels contained therein from the outside world. In particular, these upper layers greatly impede the ability of bacteria to reach the dermis, which if allowed in could potentially infect the entire body through the blood supply.

This same "wall," however, also impedes or prevents various desirable topical agents, such as anesthetics, moisturizers, wrinkle reducers (whether of the neurotoxin type such as Botox, or collagen growth stimulating serums, etc.) and similar agents from reaching the dermis and achieving the desired benefit.

Various known methods exist for mechanically breaching this barrier. For example, rollers with dozens or hundreds of very fine needles have been employed, with the needles of perhaps 200 microns or more in length, to break through to the dermis; and more recently, laser-drilled micro-holes of perhaps 100 microns in diameter and up to a millimeter or more in depth have been successfully created using so-called fractional ablative lasers. However, while the holes created by these prior art techniques facilitate transport of a topical into the dermis, they also provide a ready path for bacteria to invade the body.

In contrast, the creation of microthermal zones of denatured skin using certain embodiments of device 10 may provide a reasonable compromise between increasing transport of a variety of topical agents into the dermis while still providing a barrier to bacteria. The column of denatured skin formed by a microthermal zone 64 has increased permeability to surface-applied agents, and thus allows an increased concentration of an applied topical to reach the dermis. At the same time, the denatured skin of the MTZ 64 may continue to provide a physical barrier to bacteria.

The invention claimed is:

1. A device for providing radiation-based dermatological treatments, the device comprising:
   a device body configured to be handheld by a user;
   a VCSEL laser embodied on a chip supported in the device body, the VCSEL laser including multiple spaced-apart VCSEL beam sources provided on the chip,
   a processor;
   computer instructions stored in a non-transitory computer-readable medium and executable by the processor to pulse the multiple spaced-apart VCSEL beam sources to simultaneously generate multiple discrete laser beams for generating multiple discrete treatment spots on the skin simultaneously, the simultaneously generated multiple discrete treatment spots being spaced apart from each other by areas of non-treated skin, to thereby provide a fractional treatment to the skin, wherein each treatment spot is defined by a contiguous area on the skin surface receiving at least $1/e^2$ times the maximum intensity of a respective beam, and the areas of non-treated skin receive insufficient radiation to qualify as a treatment spot; wherein the multiple spaced-apart VCSEL beam sources are provided by multiple micro-emitters arranged in an array of multiple emitter zones, each emitter zone including a plurality of micro-emitters configured to collectively generate one of the multiple discrete laser beams, such that each emitter zone forms one of the multiple VCSEL beam sources; and
   an application end configured to be manually moved across the surface of the skin during a treatment session.

2. The device of claim 1, wherein the array of multiple emitter zones comprises a one-dimensional array.

3. The device of claim 1, wherein the array of multiple emitter zones comprises a two-dimensional array.

4. The device of claim 1, wherein at least two of the multiple emitter zones are independently addressable or controllable with respect to each other, such that at least one operational parameter of the at least two emitter zones can be independently controlled.

5. The device of claim 1, wherein the device includes, downstream of the VCSEL laser, only an open air interface, a window, or other structure that does not deflect or influence the annular distribution profile of the pulsed beams from the edge-emitting laser beam source to the skin.

6. The device of claim 1, wherein, when the application end is in contact with the skin, the VCSEL laser is separated from the skin surface by only an air gap.

7. The device of claim 1, wherein the computer instructions are executable to pulse each of the VCSEL beam sources at a pulse repetition frequency of between 1 and 50 Hz.

8. The device of claim 1, wherein the computer instructions are executable to pulse each of the VCSEL beam sources at a pulse repetition frequency of between 15 and 25 Hz.

9. The device of claim 1, wherein each of the multiple discrete laser beams is axially symmetric.

10. The device of claim 1, wherein each treatment spot has an instantaneous area of less than $0.4$ $mm^2$.

11. The device of claim 1, wherein each treatment spot has an instantaneous area of less than $0.1$ $mm^2$.

12. The device of claim 1, wherein:
the VCSEL laser has an emitter surface; and
the emitter surface is arranged such that when the application end is in contact with the skin, the emitter surface is spaced from the skin surface by less than 10 mm.

13. The device of claim 1, wherein:
the VCSEL laser has an emitter surface; and
the emitter surface is arranged such that when the application end is in contact with the skin, the emitter surface is spaced from the skin surface by less than 1 mm.

14. The device of claim 1, wherein each of the multiple laser beams is divergent in at least one direction upon incidence with the skin surface.

15. The device of claim 1, wherein the laser radiation emitted from the application end of the device meet the Class 1M or better eye safety classification per the IEC 60825-1.

16. The device of claim 1, wherein the device is configured for operation in a manual glide mode.

17. The device of claim 1, wherein the device is configured for operation in a manual stamping mode.

18. The device of claim 1, wherein the multiple micro-emitters of the VCSEL laser are formed integrally on a common substrate of a monolithic chip.

19. The device of claim 1, further comprising a power source arranged in the handheld body and configured to supply power to the VCSEL laser.

20. A device for providing radiation-based dermatological treatments, the device comprising:
a device body configured to be handheld by a user;
a VCSEL laser embodied on a chip and including multiple micro-emitters arranged in an array of multiple emitter zones provided on the chip, each emitter zone including a plurality of the micro-emitters and defining a collective beam source such that the multiple emitter zones define multiple collective beam sources;
a processor;
computer instructions stored in a non-transitory computer-readable medium and executable by the processor to pulse the multiple emitter zones of the VCSEL laser to generate multiple discrete treatment spots on the skin simultaneously, wherein the plurality of micro-emitters of each emitter zone collectively generate a discrete laser beam for generating one of the discrete treatment spots on the skin, wherein the simultaneously generated multiple discrete treatment spots are spaced apart from each other by areas of non-treated skin, thereby providing a fractional treatment to the skin, wherein each treatment spot is defined by a contiguous area on the skin surface receiving at least $1/e^2$ times the maximum intensity of a respective beam pulse, which maximum intensity is sufficient to cause a lesion in the skin, and the areas of non-treated skin receive insufficient radiation to qualify as a treatment spot;
wherein at least two of the multiple emitter zones are independently controllable with respect to each other, such that at least one operational parameter of the at least two emitter zones can be independently controlled; and
an application end configured to be manually moved across the surface of the skin during a treatment session.

21. The device of claim 20, wherein the array of multiple emitter zones comprises a one-dimensional array.

22. The device of claim 20, wherein the array of multiple emitter zones comprises a two-dimensional array.

23. The device of claim 20, wherein the device includes, downstream of the VCSEL laser, only an open air interface, a window, or other structure that does not deflect or influence the annular distribution profile of the pulsed beams from the edge-emitting laser beam source to the skin.

24. The device of claim 20, wherein the computer instruction are executable to pulse the VCSEL laser such that each of the multiple emitter zones emits a sequence of pulsed beams to the skin to generate an array of treatment spots on the skin, wherein adjacent treatment spots generated on the skin are spaced apart from each other by areas of non-treated skin between the adjacent treatment spots.

25. The device of claim 20, wherein the computer instruction are executable to pulse the multiple emitter zones simultaneously.

26. The device of claim 20, wherein the computer instruction are executable to pulse the at least two emitter zones non-simultaneously.

27. The device of claim 20, wherein the computer instruction are executable to independently power the at least two emitter zones.

28. The device of claim 20, wherein the computer instruction are executable to provide different voltages to the at least two emitter zones at the same time.

29. The device of claim 20, wherein the laser radiation emitted from the application end of the device meet the Class 1M or better eye safety classification per the IEC 60825-1.

30. The device of claim 20, wherein the multiple micro-emitters of the VCSEL laser are formed integrally on a common substrate of a monolithic chip.

31. A device for providing radiation-based dermatological treatments, the device comprising:
a device body configured to be handheld by a user;
a VCSEL laser embodied on a chip supported in the device body, the VCSEL laser including multiple spaced-apart VCSEL beam sources provided on the chip,
hardware circuitry that pulses the multiple spaced-apart VCSEL beam sources to simultaneously generate multiple discrete laser beams for generating multiple discrete treatment spots on the skin simultaneously, the simultaneously generated multiple discrete treatment spots being spaced apart from each other by areas of non-treated skin, to thereby provide a fractional treatment to the skin, wherein each treatment spot is defined by a contiguous area on the skin surface receiving at least $1/e^2$ times the maximum intensity of a respective beam pulse, and the areas of non-treated skin receive insufficient radiation to qualify as a treatment spot;
wherein the multiple spaced-apart VCSEL beam sources are provided by multiple micro-emitters arranged in an array of multiple emitter zones, each emitter zone including at least one of the micro-emitters, the at least one micro-emitter of each emitter zone generating one of the multiple discrete laser beams, such that each emitter zone forms one of the multiple VCSEL beam sources, and an application end configured to be manually moved across the surface of the skin during a treatment session.

32. The device of claim 31, wherein each emitter zone includes a plurality of micro-emitters that collectively generate one of the multiple discrete laser beams.

33. The device of claim 31, wherein at least two of the multiple emitter zones are independently addressable or controllable with respect to each other, such that at least one operational parameter of the at least two emitter zones can be independently controlled.

34. The device of claim 31, wherein the device includes, downstream of the VCSEL laser, only an open air interface, a window, or other structure that does not deflect or influence the angular distribution profile of the pulsed beams from the edge-emitting laser beam source to the skin.

35. The device of claim 31, wherein each treatment spot has an instantaneous area of less than 0.4 mm$^2$.

* * * * *

UNITED STATES PATENT AND TRADEMARK OFFICE
CERTIFICATE OF CORRECTION

Page 1 of 1

PATENT NO. : 9,005,262 B2
APPLICATION NO. : 13/366154
DATED : April 14, 2015
INVENTOR(S) : Harvey I-Heng Liu et al.

It is certified that error appears in the above-identified patent and that said Letters Patent is hereby corrected as shown below:

Title Page
Item (60), Related U.S. Application Data, "This application claims the benefit of U.S. Provisional Application No. 61/439,353 filed on February 3, 2011; U.S. Provisional Application No. 61/444,079 filed on February 17, 2011; U.S. Provisional Application No. 61/469,316 filed on March 30, 2011; U.S. Provisional Application No. 61/533,641 filed on September 12, 2011; U.S. Provisional Application No. 61/533,677 filed on September 12, 2011; U.S. Provisional Application No. 61/533,786 filed on September 12, 2011; U.S. Provisional Application No. 61/545,481 filed on October 10, 2011; U.S. Provisional Application No. 61/563,491 filed on November 23, 2011; U.S. Provisional Application No. 61/594,128 filed on February 2, 2012." ---Change to--- "This application claims the benefit of U.S. Provisional Application No. 61/439,353 filed on February 3, 2011; U.S. Provisional Application No. 61/444,079 filed on February 17, 2011; U.S. Provisional Application No. 61/469,316 filed on March 30, 2011; U.S. Provisional Application No. 61/533,641 filed on September 12, 2011; U.S. Provisional Application No. 61/533,677 filed on September 12, 2011; U.S. Provisional Application No. 61/533,786 filed on September 12, 2011; U.S. Provisional Application No. 61/545,481 filed on October 10, 2011; U.S. Provisional Application No. 61/563,491 filed on November 23, 2011; and U.S. Provisional Application No. 61/594,128 filed on February 2, 2012; Co-Pending U.S. Patent Application No. 13/366,256 filed on February 3, 2012; Co-Pending U.S. Patent Application No. 13/366,177 filed on February 3, 2012, Co-Pending US. Patent Application No. 13/366,202 filed on February 3, 2012; Co-Pending U.S. Patent Application No. 13/366,237 filed on February 3, 2012 and Co-Pending U.S. Patent Application No. 13/366,246 filed on February 3, 2012; all of which applications are herein incorporated by reference in their entirety."

Signed and Sealed this
Eighteenth Day of August, 2015

Michelle K. Lee
*Director of the United States Patent and Trademark Office*